United States Patent
Bruce et al.

(10) Patent No.: US 7,687,637 B2
(45) Date of Patent: Mar. 30, 2010

(54) 5-PHENYLTHIAZOLE DERIVATIVES AND USE AS PI3 KINASE INHIBITORS

(75) Inventors: Ian Bruce, West Sussex (GB); Peter Finan, West Sussex (GB); Catherine Leblanc, West Sussex (GB); Clive McCarthy, Basel (CH); Lewis Whitehead, Marblehead, MA (US); Nicola Press, West Sussex (GB); Graham Charles Bloomfield, West Sussex (GB); Judy Hayler, West Sussex (GB); Louise Kirman, Marblehead, MA (US); Mrinalini Sachin Oza, West Sussex (GB); Lena Shukla, London (GB)

(73) Assignee: Novartis AG, Basel (CH)

( * ) Notice: Subject to any disclaimer, the term of this patent is extended or adjusted under 35 U.S.C. 154(b) by 778 days.

(21) Appl. No.: 10/504,259

(22) PCT Filed: Feb. 27, 2003

(86) PCT No.: PCT/EP03/02036

§ 371 (c)(1),
(2), (4) Date: Jan. 31, 2005

(87) PCT Pub. No.: WO03/072557

PCT Pub. Date: Sep. 4, 2003

(65) Prior Publication Data

US 2005/0119320 A1 Jun. 2, 2005

(30) Foreign Application Priority Data

Feb. 28, 2002 (GB) .................................. 0204765.2
Dec. 19, 2002 (GB) .................................. 0229626.7

(51) Int. Cl.
*A61K 31/426* (2006.01)
*C07D 277/46* (2006.01)

(52) U.S. Cl. ...................................... 548/195; 514/371
(58) Field of Classification Search ................... 548/195
See application file for complete search history.

(56) References Cited

U.S. PATENT DOCUMENTS

| | | | |
|---|---|---|---|
| 3,749,775 A | 7/1973 | Fancher | |
| 4,490,393 A | 12/1984 | Sakano et al. | 424/263 |
| 4,891,375 A | 1/1990 | Lowe, III | 514/252 |
| 5,668,161 A | 9/1997 | Talley et al. | 514/365 |
| 5,856,347 A * | 1/1999 | Hashiguchi et al. | 514/370 |
| 5,877,191 A | 3/1999 | Caldwell et al. | |
| 6,518,277 B1 | 2/2003 | Sadhu et al. | 514/266.1 |
| 2004/0171643 A1 | 9/2004 | De Cointet et al. | |

FOREIGN PATENT DOCUMENTS

| | | |
|---|---|---|
| DE | 44 01 911 | 8/1995 |
| EP | 0 161 442 | 11/1985 |
| EP | 0 928 790 | 7/1999 |
| EP | 0 513 387 | 3/2000 |
| GB | 951 885 | 3/1964 |
| GB | 1131207 | 10/1968 |
| JP | 62-178590 | 8/1987 |
| WO | 96/03392 A1 | 2/1996 |
| WO | 99/32106 A1 | 7/1999 |
| WO | 01/53266 | 7/2001 |
| WO | 01/81346 A2 | 11/2001 |
| WO | 02/10162 | 2/2002 |
| WO | 02/49632 | 6/2002 |
| WO | 03/014095 A1 | 2/2003 |

OTHER PUBLICATIONS

Garreau, CA 48:18307, 1954.*
Fancher, CA 79:122574, 1973.*
Stoyanova et al., "Lipid Kinase and Protein Kinase Activities of G-Protein-Coupled Phosphoinositide 3-Kinase γ: Structure-Activity Analysis and Interactions with Wortmannin", Biochem. J., vol. 324, pp. 489-495 (1997).
Lee et al., "5,5!-Signmatropic, Shift of N-phenyl-N'-(2-thiazolyl)hydrazines and N,N'-bis(2-thiazolyl)hydrazines into 2-amino-5-(p-aminophenyl)thiazoles and 5,5'-bis(2-aminothiazole) Derivaties", Tetrahedron Letters, vol. 41, No. 20, pp. 3883-3886 (2000).
Bizhev et al., "2-Aminothiazole Derivates as New Anesthetics for Fish-Breeding", Farmatslya (Sofia, Bulgaria), vol. 37, No. 5, pp. 14-21 (1987)—Chemical Abstract No. 108:180074.
Nair et al., "Regioselective '4+2! and '2+2! Cycloadditions of 1-axirines to Heterocumulenes. Formulation and Rearrangements of the Cycloadducts", J. Organic Chem., vol. 39, No. 25, pp. 3763-3766 (1974)—Chemical Abstract No. 82:16801.
Ambinter: Exploratory Library, Ambinter, 46 Quai Louis Bleriot, Paris, F-75016, France (2003)—Chemical Abstract Nos. t0309-7995, t0309-7981, t0309-7982, t0309-7980.

* cited by examiner

*Primary Examiner*—Laura L. Stockton
(74) *Attorney, Agent, or Firm*—John Alexander

(57) ABSTRACT

Compounds of formula I

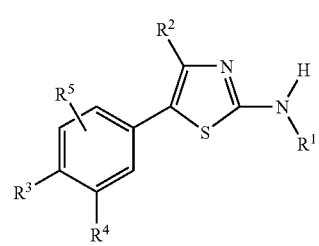

in free or salt form, wherein $R^1$, $R^2$, $R^3$, $R^4$ and $R^5$ have the meanings as indicated in the specification, are useful for treating diseases mediated by phosphatidylinositol 3-kinase. Pharmaceutical compositions that contain the compounds and processes for preparing the compounds are also described.

14 Claims, No Drawings

5-PHENYLTHIAZOLE DERIVATIVES AND USE AS PI3 KINASE INHIBITORS

The present invention relates to organic compounds, their preparation and their use as pharmaceuticals.

In a first aspect, the present invention provides compounds of formula I

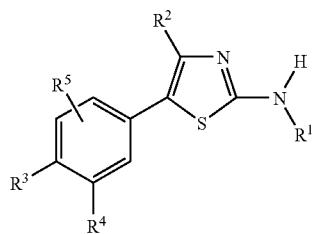

in free or salt form, wherein $R^1$ is hydrogen or aminocarbonyl optionally substituted by nitrile, or $R^1$ is $C_1$-$C_8$-alkylcarbonyl or $C_1$-$C_8$-alkylaminocarbonyl either of which being optionally substituted by halogen, hydroxy, amino, $C_1$-$C_8$-alkylamino, di($C_1$-$C_8$-alkyl)amino, carboxy, $C_1$-$C_8$-alkoxycarbonyl, nitrile, phenyl, $C_1$-$C_8$-haloalkyl, or by $C_1$-$C_8$-alkyl optionally substituted by hydroxy, or $R^1$ is $C_1$-$C_8$-alkylcarbonyl or $C_1$-$C_8$-alkylaminocarbonyl either of which being optionally substituted by $C_3$-$C_8$-cycloalkyl optionally substituted by hydroxy, or $R^1$ is $C_1$-$C_8$-alkylcarbonyl or $C_1$-$C_8$-alkylaminocarbonyl either of which being optionally substituted by $C_1$-$C_8$-alkoxy optionally substituted by hydroxy, or $R^1$ is $C_1$-$C_8$-alkylcarbonyl or $C_1$-$C_8$-alkylaminocarbonyl either of which being optionally substituted by phenyl optionally substituted by hydroxy or $C_1$-$C_8$-alkyl, or $R^1$ is $C_1$-$C_8$-alkylcarbonyl or $C_1$-$C_8$-alkylaminocarbonyl either of which being optionally substituted by a 5- or 6-membered heterocyclic ring having one or more ring hetero atoms selected from the group consisting of oxygen, nitrogen and sulphur, that ring being optionally substituted by hydroxy, $C_1$-$C_8$-alkyl or $C_1$-$C_8$-alkoxy, or $R^1$ is —(C=O)—(NH)$_a$-Het where a is 0 or 1 and Het denotes a 4-, 5- or 6-membered heterocyclic ring having one or more ring hetero atoms selected from the group consisting of oxygen, nitrogen and sulphur, that ring being optionally substituted by hydroxy, $C_1$-$C_8$-alkyl, $C_1$-$C_8$-alkoxy or by a 5- or 6-membered heterocyclic ring having one or more ring hetero atoms selected from the group consisting of oxygen, nitrogen and sulphur, or $R^1$ is —(C=O)—(NH)$_b$-T where b is 0 or 1 and T denotes $C_3$-$C_8$-cycloalkyl or phenyl either of which being optionally substituted by hydroxy, $C_1$-$C_8$-alkyl, $C_1$-$C_8$-alkoxy, or by $C_1$-$C_8$-alkyl substituted by hydroxy, $R^2$ is $C_1$-$C_3$-alkyl or halogen;

one of $R^3$ and $R^4$ is $R^6$ and the other is $R^7$;

$R^5$ is hydrogen or halogen;

$R^6$ is hydrogen, hydroxy, amino, —SOR$^8$, —SO$_2$R$^8$, —SO$_2$NH$_2$, —SO$_2$NR$^9$R$^{10}$, —COR$^8$, —CONHR$^8$, —NHSO$_2$R$^8$, nitrile, carboxy, —OR$^8$ or $C_1$-$C_8$-haloalkyl;

$R^7$ is hydrogen, $R^{11}$, —OR$^{11}$, halo, carboxy, —SO$_2$R$^8$, nitrile or $C_1$-$C_8$-haloalkyl, or, when $R^4$ is $R^7$, $R^7$ can also be —NR$^{12}$R$^{13}$, R$^{14}$ or —OR$^{14}$;

$R^8$ and $R^{11}$ are independently $C_1$-$C_8$-alkyl or $C_3$-$C_8$-cycloalkyl, optionally substituted by halogen, hydroxy, $C_1$-$C_8$-alkoxy, nitrile, amino, $C_1$-$C_8$-alkylamino or di($C_1$-$C_8$-alkyl)amino;

either $R^9$ is $C_1$-$C_8$-alkyl or $C_3$-$C_8$-cycloalkyl, optionally substituted by hydroxy, $C_1$-$C_8$-alkoxy, nitrile, amino, $C_1$-$C_8$-alkylamino, di($C_1$-$C_8$-alkyl)amino or a 5- or 6-membered heterocyclic ring having one or more ring hetero atoms selected from the group consisting of oxygen, nitrogen and sulphur, that ring being optionally substituted by $C_1$-$C_8$-alkyl, and $R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl;

either $R^{12}$ is $C_1$-$C_8$-alkyl or $C_3$-$C_8$-cycloalkyl optionally substituted by hydroxy, amino, $C_1$-$C_8$-alkylamino or di($C_1$-$C_8$-alkyl)amino, and $R^{13}$ is hydrogen or $C_1$-$C_8$-alkyl; or $R^{12}$ and $R^{13}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl; and $R^{14}$ is $C_1$-$C_8$-alkyl optionally substituted by hydroxy or —NR$^{12}$R$^{13}$.

Terms used in the specification have the following meanings:

"Optionally substituted" as used herein means the group referred to can be substituted at one or more positions by any one or any combination of the radicals listed thereafter.

"Aminocarbonyl" as used herein denotes amino attached through the nitrogen atom to a carbonyl group.

"$C_1$-$C_8$-alkyl" denotes straight chain or branched $C_1$-$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$-$C_8$-alkyl is $C_1$-$C_4$-alkyl.

"$C_3$-$C_8$-cycloalkyl" denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably "$C_3$-$C_8$-cycloalkyl" is cyclopropyl, cyclobutyl, cyclopentyl, cyclohexyl, cycloheptyl or cyclooctyl.

"$C_1$-$C_8$-alkoxy" denotes straight chain or branched $C_1$-$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$-$C_8$-alkoxy is $C_1$-$C_4$-alkoxy.

"$C_1$-$C_8$-haloalkyl" denotes $C_1$-$C_8$-alkyl as hereinbefore defined substituted by one or more halogen atoms, preferably one, two or three halogen atoms, preferably fluorine or chlorine atoms. Preferably $C_1$-$C_8$-haloalkyl is $C_1$-$C_4$-alkyl substituted by one, two or three fluorine or chlorine atoms.

"$C_1$-$C_8$-alkylcarbonyl", "$C_1$-$C_8$-alkoxycarbonyl" and "$C_1$-$C_8$-haloalkylcarbonyl" and denote $C_1$-$C_8$-alkyl, $C_1$-$C_8$- alkoxy or $C_1$-$C_8$-haloalkyl respectively as hereinbefore defined attached by a carbon atom to a carbonyl group.

"$C_1$-$C_8$-alkylamino" and "di($C_1$-$C_8$-alkyl)amino" denote amino substituted respectively by one or two $C_1$-$C_8$-alkyl groups as hereinbefore defined, which may be the same or different. Preferably $C_1$-$C_8$-alkylamino and di($C_1$-$C_8$-alkyl)amino are respectively $C_1$-$C_4$-alkylamino and di($C_1$-$C_4$-alkyl)amino.

"$C_3$-$C_8$-cycloalkyl" denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably "$C_3$-$C_8$-cycloalkyl" is cyclopropyl, cyclobutyl, cyclopentyl, cyclohexyl, cycloheptyl or cyclooctyl.

"Halogen" or "halo" may be fluorine, chlorine, bromine or iodine; preferably it is fluorine or chlorine.

"4, 5- or 6-membered heterocyclic ring containing at least one ring heteroatom selected from the group consisting of nitrogen, oxygen and sulphur" as used herein may be, for example, azetidine, furan, pyrrole, pyrrolidine, pyrazole, imidazole, triazole, isotriazole, tetrazole, thiadiazole, isothiazole, oxadiazole, pyridine, oxazole, isoxazole, pyrazine, pyridazine, pyrimidine, piperazine, morpholino, triazine, oxazine or thiazole. Preferred heterocyclic rings include piperazine, morpholino, imidazole, isotriazole, pyrazole, pyridine, furan, oxazole, isoxazole and azetidine.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of the present invention include compounds of formula I in free or salt form, wherein $R^1$ is hydrogen or aminocarbonyl optionally substituted by nitrile, or $R^1$ is $C_1$-$C_8$-alkylcarbonyl or $C_1$-$C_8$-alkylaminocarbonyl either of which being optionally substituted by halogen, hydroxy, di($C_1$-$C_8$-alkyl)amino, carboxy, $C_1$-$C_8$-alkoxycarbonyl, nitrile, phenyl, $C_1$-$C_8$-haloalkyl, or by $C_1$-$C_8$-alkyl optionally substituted by hydroxy, or $R^1$ is $C_1$-$C_8$-alkylaminocarbonyl optionally substituted by $C_3$-$C_8$-cycloalkyl, or $R^1$ is $C_1$-$C_8$-alkylcarbonyl or $C_1$-$C_8$-alkylaminocarbonyl either of which being optionally substituted by $C_1$-$C_8$-alkoxy optionally substituted by hydroxy, or $R^1$ is $C_1$-$C_8$-alkylcarbonyl or $C_1$-$C_8$-alkylaminocarbonyl either of which being optionally substituted by a 5- or 6-membered heterocyclic ring having one or more ring hetero atoms selected from the group consisting of oxygen, nitrogen and sulphur, that ring being optionally substituted by $C_1$-$C_8$-alkyl, or $R^1$ is —(C=O)—(NH)$_a$-Het where a is 0 or 1 and Het denotes a 4-, 5- or 6-membered N-heterocyclic ring having one or more ring hetero atoms selected from the group consisting of oxygen, nitrogen and sulphur, that ring being optionally substituted by hydroxy, $C_1$-$C_8$-alkyl, $C_1$-$C_8$-alkoxy or by a 5- or 6-membered heterocyclic ring having one or more ring hetero atoms selected from the group consisting of oxygen, nitrogen and sulphur, or $R^1$ is —(C=O)—NH-T where T denotes $C_3$-$C_8$-cycloalkyl or phenyl either of which being optionally substituted by hydroxy, $C_1$-$C_8$-alkyl, or by $C_1$-$C_8$-alkyl substituted by hydroxy, $R^2$ is $C_1$-$C_3$-alkyl;

one of $R^3$ and $R^4$ is $R^6$ and the other is $R^7$;

$R_5$ is hydrogen or halogen;

$R^6$ is hydrogen, hydroxy, amino, —$SO_2R^8$, —$SO_2NH_2$, —$SO_2NR^9R^{10}$, —$NHSO_2R^8$, cyano, carboxy, —$OR^8$ or $C_1$-$C_4$-haloalkyl;

$R^7$ is hydrogen, —$OR^{11}$, fluorine, chlorine, bromine, nitrile or $C_1$-$C_4$-haloalkyl, or, when $R^4$ is $R^7$, $R^7$ can also be —$NR^{12}R^{13}$ or —$OR^{14}$;

$R^8$ and $R^{11}$ are independently $C_1$-$C_8$-alkyl;

either $R^9$ is $C_1$-$C_8$-alkyl optionally substituted by hydroxy, $C_3$-$C_8$-cycloalkyl optionally substituted by hydroxy, $C_1$-$C_8$-alkoxy, nitrile, di($C_1$-$C_8$-alkyl)amino or a 5- or 6-membered heterocyclic ring having one or more ring hetero atoms selected from the group consisting of oxygen and nitrogen, that ring being optionally substituted by $C_1$-$C_8$-alkyl, and $R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl;

either $R^{12}$ is $C_1$-$C_8$-alkyl optionally substituted by di($C_1$-$C_8$-alkyl)amino, and $R^{13}$ is hydrogen or $C_1$-$C_8$-alkyl; or $R^{12}$ and $R^{13}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl; and $R^{14}$ is $C_1$-$C_8$-alkyl.

Further preferred compounds of formula I in free or salt form include those wherein $R^1$ is hydrogen or aminocarbonyl optionally substituted by nitrile, or $R^1$ is $C_1$-$C_4$-alkylcarbonyl or $C_1$-$C_4$-alkylaminocarbonyl either of which being optionally substituted by halogen, hydroxy, di($C_1$-$C_4$-alkyl)amino, carboxy, $C_1$-$C_4$-alkoxycarbonyl, nitrile, phenyl, $C_1$-$C_4$-haloalkyl, or by $C_1$-$C_4$-alkyl optionally substituted by hydroxy, or $R^1$ is $C_1$-$C_4$-alkylaminocarbonyl optionally substituted by $C_3$-$C_8$-cycloalkyl, or $R^1$ is $C_1$-$C_4$-alkylcarbonyl or $C_1$-$C_4$-alkylaminocarbonyl either of which being optionally substituted by $C_1$-$C_4$-alkoxy optionally substituted by hydroxy, or $R^1$ is $C_1$-$C_4$-alkylcarbonyl or $C_1$-$C_4$-alkylaminocarbonyl either of which being optionally substituted by a 5- or 6-membered heterocyclic ring having one or more ring hetero atoms selected from the group consisting of oxygen, nitrogen and sulphur, that ring being optionally substituted by $C_1$-$C_4$-alkyl, or $R^1$ is —(C=O)—(NH)$_a$-Het where a is 0 or 1 and Het denotes a 4-, 5- or 6-membered N-heterocyclic ring having one or more ring hetero atoms selected from the group consisting of oxygen, nitrogen and sulphur, that ring being optionally substituted by hydroxy, $C_1$-$C_4$-alkyl, $C_1$-$C_4$-alkoxy or by a 5- or 6-membered heterocyclic ring having one or more ring hetero atoms selected from the group consisting of oxygen, nitrogen and sulphur, or $R^1$ is —(C=O)—NH-T where T denotes $C_3$-$C_8$-cycloalkyl or phenyl either of which being optionally substituted by hydroxy, $C_1$-$C_4$-alkyl, or by $C_1$-$C_4$-alkyl substituted by hydroxy, $R^2$ is $C_1$-$C_3$-alkyl;

one of $R^3$ and $R^4$ is $R^6$ and the other is $R^7$;

$R^5$ is hydrogen or halogen;

$R^6$ is hydrogen, hydroxy, amino, $SO_2R^8$, $SO_2NH_2$, $SO_2NR^9R^{10}$, $NHSO_2R^8$, nitrile, carboxy, $OR^8$ or $C_1$-$C_4$-haloalkyl;

$R^7$ is hydrogen, —$OR^{11}$, fluorine, chlorine, bromine, cyano or $C_1$-$C_4$-haloalkyl, or, when $R^4$ is $R^7$, $R^7$ can also be —$NR^{12}R^{13}$ or —$OR^{14}$;

$R^8$ and $R^{11}$ are independently $C_1$-$C_4$-alkyl;

either $R^9$ is $C_1$-$C_4$-alkyl optionally substituted by hydroxy, $C_3$-$C_8$-cycloalkyl optionally substituted by hydroxy, $C_1$-$C_4$-alkoxy, nitrile, di($C_1$-$C_4$-alkyl)amino or a 5- or 6-membered heterocyclic ring having one or more ring hetero atoms selected from the group consisting of oxygen and nitrogen, that ring being optionally substituted by $C_1$-$C_4$-alkyl, and $R^{10}$ is hydrogen or $C_1$-$C_4$-alkyl; or $R^9$ and $R^{10}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_4$-alkyl;

either $R^{12}$ is $C_1$-$C_4$-alkyl optionally substituted by di($C_1$-$C_4$-alkyl)amino, and $R^{13}$ is hydrogen or $C_1$-$C_4$-alkyl; or $R^{12}$ and $R^{13}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_4$-alkyl; and $R^{14}$ is $C_{1-4}$ alkyl.

In a second aspect, the present invention provides compounds of formula I in free or salt form, wherein $R^1$ is hydrogen, or $R^1$ is aminocarbonyl, $C_1$-$C_8$-alkylcarbonyl or $C_1$-$C_8$-alkylaminocarbonyl either of which being optionally substituted by hydroxy, amino, $C_1$-$C_8$-alkylamino, di($C_1$-$C_8$-alkyl(amino), carboxy, $C_1$-$C_8$-alkyl optionally substituted by hydroxy, halogen, $C_3$-$C_8$-cycloalkyl optionally substituted by hydroxy, $C_1$-$C_8$-alkoxy optionally substituted by hydroxy, $C_1$-$C_8$-alkoxycarbonyl, nitrile, halogen, phenyl optionally substituted by hydroxy or $C_1$-$C_8$-alkyl, or a 5- or 6-membered heterocyclic ring having one or more ring hetero atoms selected from the group consisting of oxygen, nitrogen and sulphur, that ring being optionally substituted by hydroxy, $C_1$-$C_8$-alkyl or $C_1$-$C_8$-alkoxy, or $R^1$ is —(C=O)—(NH)$_a$-Het where a is 0 or 1 and Het denotes a 5- or 6-membered heterocyclic ring having one or more ring hetero atoms selected from the group consisting of oxygen, nitrogen and sulphur, that ring being optionally substituted by hydroxy, $C_1$-$C_8$-alkyl or $C_1$-$C_8$-alkoxy;

$R^2$ is $C_1$-$C_3$-alkyl or halogen;

one of $R^3$ and $R^4$ is $R^6$ and the other is $R^7$;

$R^5$ is hydrogen or halogen;

$R^6$ is hydrogen, hydroxy, amino, —$SOR^8$, —$SO_2R^8$, —$SO_2NH_2$, —$SO_2NR^9R^{10}$, —$COR^8$, —$CONHR^8$, —$NHSO_2R^8$, nitrile, carboxy, —$OR^8$ or $C_1$-$C_8$-haloalkyl;

$R^7$ is hydrogen, $R^{11}$, —$OR^{11}$, halo, carboxy, —$SO_2R^8$, cyano or $C_1$-$C_8$-haloalkyl, or, when $R^4$ is $R^7$, $R^7$ can also be —$NR^{12}R^{13}$, $R^{14}$ or —$OR^{14}$;

$R^8$ and $R^{11}$ are independently $C_1$-$C_8$-alkyl or $C_3$-$C_8$-cycloalkyl, optionally substituted by halogen, hydroxy, $C_1$-$C_8$-alkoxy, nitrile, amino, $C_1$-$C_8$-alkylamino or di($C_1$-$C_8$-alkyl) amino;

either $R^9$ is $C_1$-$C_8$-alkyl or $C_3$-$C_8$-cycloalkyl, optionally substituted by hydroxy, $C_1$-$C_8$-alkoxy, nitrile, amino, $C_1$-$C_8$-alkylamino, di($C_1$-$C_8$-alkyl)amino or a 5- or 6-membered heterocyclic ring having one or more ring hetero atoms selected from the group consisting of oxygen, nitrogen and sulphur, that ring being optionally substituted by $C_1$-$C_8$-alkyl, and $R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl;

either $R^{12}$ is $C_1$-$C_8$-alkyl or $C_3$-$C_8$-cycloalkyl optionally substituted by hydroxy, amino, $C_1$-$C_8$-alkylamino or di($C_1$-$C_8$-alkyl)amino, and $R^{13}$ is hydrogen or $C_1$-$C_8$-alkyl; or $R^{12}$ and $R^{13}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl; and $R^{14}$ is $C_1$-$C_8$-alkyl optionally substituted by hydroxy or —$NR^{12}R^{13}$.

Preferred compounds include compounds of formula I wherein $R^1$ is hydrogen, or $R^1$ is aminocarbonyl, $C_1$-$C_8$-alkylcarbonyl or $C_1$-$C_8$-alkylaminocarbonyl either of which being optionally substituted by hydroxy, di($C_1$-$C_8$-alkylamino), carboxy, $C_1$-$C_8$-alkyl optionally substituted by hydroxy, halogen, $C_3$-$C_8$-cycloalkyl optionally substituted by hydroxy, $C_1$-$C_8$-alkoxy optionally substituted by hydroxy, $C_1$-$C_8$-alkoxycarbonyl, nitrile, halogen, phenyl optionally substituted by hydroxy or $C_1$-$C_8$-alkyl, or a 5- or 6-membered heterocyclic ring having one or more ring hetero atoms selected from the group consisting of oxygen, nitrogen and sulphur, that ring being optionally substituted by $C_1$-$C_8$-alkyl or $C_1$-$C_8$-alkoxy, or $R^1$ is —(C=O)—(NH)$_a$-Het where a is 0 or 1 and Het denotes a 5- or 6-membered N-heterocyclic ring optionally substituted by hydroxy, $C_1$-$C_8$-alkyl or $C_1$-$C_8$-alkoxy;

$R^2$ is $C_1$-$C_3$-alkyl;

one of $R^3$ and $R^4$ is $R^6$ and the other is $R^7$;

$R^5$ is hydrogen or halogen;

$R^6$ is hydrogen, hydroxy, amino, —$SO_2R^8$, —$SO_2NH_2$, —$SO_2NR^9R^{10}$, —$NHSO_2R^8$, cyano, carboxy, —$OR^8$ or $C_1$-$C_4$-haloalkyl;

$R^7$ is hydrogen, —$OR^{11}$, fluorine, chlorine, bromine, cyano or $C_1$-$C_4$-haloalkyl, or, when $R^4$ is $R^7$, $R^7$ can also be —$NR^{12}R^{13}$ or —$OR^{14}$;

$R^8$ and $R^{11}$ are independently $C_1$-$C_8$-alkyl;

either $R^9$ is $C_1$-$C_8$-alkyl optionally substituted by hydroxy, $C_3$-$C_8$-cycloalkyl optionally substituted by hydroxy, $C_1$-$C_8$- alkoxy, nitrile, di($C_1$-$C_8$-alkyl)amino or a 5- or 6-membered heterocyclic ring having one or more ring hetero atoms selected from the group consisting of oxygen and nitrogen, that ring being optionally substituted by $C_1$-$C_8$-alkyl, and $R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl;

either $R^{12}$ is $C_1$-$C_8$-alkyl optionally substituted by di($C_1$-$C_8$-alkyl)amino, and $R^{13}$ is hydrogen or $C_1$-$C_8$-alkyl; or $R^{12}$ and $R^{13}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl; and $R^{14}$ is $C_1$-$C_8$-alkyl.

In a third aspect, the present invention provides compounds of formula I in free or salt form, wherein $R^1$ is hydrogen, or $C_1$-$C_8$-alkylcarbonyl or $C_1$-$C_8$-alkylaminocarbonyl optionally substituted by amino, carboxy, $C_1$-$C_8$-alkoxy, $C_1$-$C_8$-alkoxycarbonyl, nitrile, halogen or a 5 or 6-membered heterocyclic ring having one or more ring hetero atoms selected from the group consisting of oxygen, nitrogen and sulphur, that ring being optionally substituted by $C_1$-$C_8$-alkyl;

$R^2$ is $C_1$-$C_3$-alkyl or halogen;

one of $R^3$ and $R^4$ is $R^6$ and the other is $R^7$;

$R^5$ is hydrogen or halogen;

$R^6$ is hydrogen, hydroxy, amino, $SOR^8$, $SO_2R^8$, $SO_2NH_2$, $SO_2NR^9R^{10}$, $COR^8$, $CONHR^8$, $NHSO_2R^8$, nitrile, carboxy, $OR^8$ or $C_1$-$C_8$-haloalkyl;

$R^7$ is hydrogen, $R^{11}$, $OR^{11}$, halo, cyano, carboxy, $SO_2R^8$, or $C_1$-$C_8$-haloalkyl, or, when $R^4$ is $R^7$, $R^7$ can also be $NR^{12}R^{13}$, $R^{14}$ or $OR^{14}$;

$R^8$ and $R^{11}$ are independently $C_1$-$C_8$-alkyl or $C_3$-$C_8$-cycloalkyl, optionally substituted by halogen, hydroxy, $C_1$-$C_8$-alkoxy, nitrile, amino, $C_1$-$C_8$-alkylamino or di($C_1$-$C_8$-alkyl)amino; either $R^9$ is $C_1$-$C_8$-alkyl or $C_3$-$C_8$-cycloalkyl, optionally substituted by hydroxy, $C_1$-$C_8$-alkoxy, nitrile, amino, $C_1$-$C_8$-alkylamino, di($C_1$-$C_8$-alkyl)amino or a 5 or 6-membered heterocyclic ring having one or more ring hetero atoms selected from the group consisting of oxygen, nitrogen and sulphur, that ring being optionally substituted by $C_1$-$C_8$-alkyl, and $R^{10}$ is hydrogen or $C_1$-$C_8$-alkyl; or $R^9$ and $R^{10}$ together with the nitrogen atom to which they are attached form a 5 or 6-membered heterocyclic ring that contains one or more further hetero atoms selected from the group consisting of oxygen, nitrogen and sulphur, that ring being optionally substituted by $C_1$-$C_8$-alkyl;

either $R^{12}$ is $C_1$-$C_8$-alkyl or $C_3$-$C_8$-cycloalkyl optionally substituted by hydroxy, amino, $C_1$-$C_8$-alkylamino or di($C_1$-$C_8$-alkyl)amino, and $R^{13}$ is hydrogen or $C_1$-$C_8$-alkyl; or $R^{12}$ and $R^{13}$ together with the nitrogen atom to which they are attached form a 5 or 6-membered heterocyclic ring that contains one or more further hetero atoms selected from the group consisting of oxygen, nitrogen and sulphur, that ring being optionally substituted by $C_1$-$C_8$-alkyl; and $R^{14}$ is $C_1$-$C_8$-alkyl optionally substituted by hydroxy or $NR^{12}R^{13}$.

Preferred compounds include compounds of formula I, wherein $R^1$ is hydrogen, $C_1$-$C_8$-alkylcarbonyl, $C_1$-$C_8$-alkylaminocarbonyl optionally substituted by carboxy or $C_1$-$C_8$-alkoxycarbonyl;

$R^2$ is $C_1$-$C_3$-alkyl;

one of $R^3$ and $R^4$ is $R^6$ and the other is $R^7$;

$R^5$ is hydrogen or halogen;

$R^6$ is hydrogen, hydroxy; amino, $SO_2R^8$, $SO_2NH_2$, $SO_2NR^9R^{10}$, $NHSO_2R^8$, cyano, carboxy, $OR^8$ or $C_1$-$C_4$-haloalkyl;

$R^7$ is hydrogen, $OR^{11}$, fluorine, chlorine, bromine, cyano or $C_1$-$C_4$-haloalkyl, or, when $R^4$ is $R^7$, $R^7$ can also be $NR^{12}R^{13}$ or $OR^{14}$;

$R^8$ and $R^{11}$ are independently $C_1$-$C_8$-alkyl;

either $R^9$ is $C_1$-$C_8$-alkyl or $C_3$-$C_8$-cycloalkyl, optionally substituted by hydroxy, $C_1$-$C_8$-alkoxy, nitrile, di($C_1$-$C_8$-alkyl)amino or a 5 or 6-membered heterocyclic ring having one or more ring hetero atoms selected from the group consisting of oxygen and nitrogen, that ring being optionally substituted by $C_1$-$C_8$-alkyl, and $R^{10}$ is hydrogen or $C_1$-$C_8$-alkyl; or $R^9$ and $R^{10}$ together with the nitrogen atom to which they are attached form a 5 or 6-membered heterocyclic ring that contains one or more further hetero atoms selected from the group consisting of oxygen and nitrogen, that ring being optionally substituted by $C_1$-$C_8$-alkyl;

either $R^{12}$ is $C_1$-$C_8$-alkyl optionally substituted by di($C_1$-$C_8$-alkyl)amino, and $R^{13}$ is hydrogen or $C_1$-$C_8$-alkyl; or $R^{12}$ and $R^{13}$ together with the nitrogen atom to which they are attached form a 5 or 6-membered heterocyclic ring that contains one or more further hetero atoms selected from the group consisting of oxygen and nitrogen, that ring being optionally substituted by $C_1$-$C_8$-alkyl; and $R^{14}$ is $C_1$-$C_8$-alkyl.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

Specific preferred compounds of formula I are described hereinafter in the Examples.

The invention provides, in another aspect, a process for preparing a compound of formula I in free or salt form which comprises the steps of:

(i) (A) for the preparation of compounds of formula I where $R^1$ is $C_1$-$C_8$-alkylcarbonyl, $C_1$-$C_8$-alkylaminocarbonyl optionally substituted by amino, carboxy, $C_1$-$C_8$-alkoxy, $C_1$-$C_8$-alkoxycarbonyl, nitrile or halogen, or a 5 or 6-membered heterocyclic ring having one or more ring hetero atoms selected from the group consisting of oxygen, nitrogen and sulphur, that ring being optionally substituted by $C_1$-$C_8$-alkyl, reacting a compound of formula II

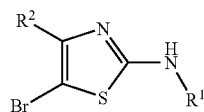

II wherein $R^1$ and $R^2$ are as hereinbefore defined, with a compound of formula III

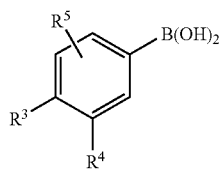

III wherein $R^3$, $R^4$ and $R^5$ are as hereinbefore defined, in the presence of a transition metal catalyst, preferably palladium;

(B) for the preparation of compounds of formula I where $R^3$ or $R^4$ is —$SO_2NH_2$ or —$SO_2NR^9R^{10}$, reacting a compound of formula IV

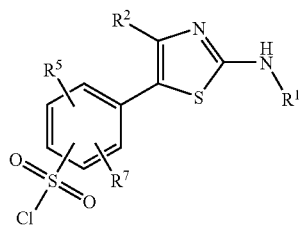

IV wherein $R^1$, $R^2$, $R^5$ and $R^7$ are as hereinbefore defined and the —$SO_2Cl$ group is meta or para to the thiazole ring, with ammonia or a compound of formula $R^9R^{10}NH$;

(C) for the preparation of compounds of formula I where $R^3$ or $R^4$ is $NHSO_2R^8$, reacting a compound of formula I where one or $R^3$ and $R^4$ is $NH_2$ with a sulfonyl chloride of formula $R^8SO_2Cl$;

(D) for the preparation of compounds of formula I where $R^4$ is $NR^{12}R^{13}$, reacting a compound of formula I where $R^4$ is halogen and $R^3$ is $SO_2R^8$ with a compound of formula V

V where $R^{12}$ and $R^{13}$ are as hereinbefore defined;

(E) for the preparation of compounds of formula I where $R^1$ is optionally substituted $C_1$-$C_8$-alkylaminocarbonyl, reacting a compound of formula I where $R^1$ is hydrogen with a compound of formula VI

VI $R^{15}$—N=C=O, wherein $R^{15}$ is $C_1$-$C_8$-alkyl optionally substituted by carboxy or $C_1$-$C_8$-alkoxycarbonyl;

(F) for the preparation of compounds of formula I where one of $R^3$ and $R^4$ is amino and the other is hydrogen or halogen and at least one of $R^3$, $R^4$ and $R^5$ is halogen, halogenating a compound of formula I where $R^3$ or $R^4$ is amino and the other is hydrogen;

(G) reacting a compound of formula VII

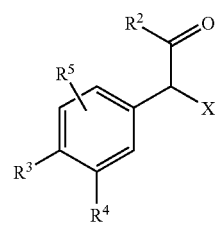

VII wherein $R^2$, $R^3$, $R^4$ and $R^5$ are as hereinbefore defined and X is halogen, with a compound of formula VIII

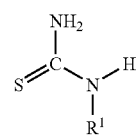

VIII wherein $R^1$ is as hereinbefore defined;

(H) for the preparation of compounds of formula I where $R^3$ or $R^4$ is —$SO_2R^8$ and $R^8$ is methyl, reacting a compound of formula IV wherein $R^1$, $R^2$, $R^5$ and $R^7$ are as hereinbefore defined and the —$SO_2Cl$ group is meta or para to the thiazolyl ring, with an alkali metal sulphite and an alkali metal bicarbonate, followed by reaction with bromoacetic acid or an alkyl halide, e.g. iodomethane at elevated temperature;

(I) for the preparation of compounds of formula I where $R^1$ is $C_1$-$C_8$-alkylamino-carbonyl optionally substituted by a 5- or 6-membered heterocyclic ring having one or more ring hetero atoms selected from the group consisting of oxygen, nitrogen and sulphur, that ring being optionally substituted by $C_1$-$C_8$-alkyl or $C_1$-$C_8$-alkoxy, or where $R^1$ is —(C=O)—(NH)$_a$-Het where a is 0 and Het denotes a 4-, 5- or 6-membered heterocyclic ring having one or more ring hetero atoms selected from the group consisting of oxygen, nitrogen and sulphur, that ring being optionally substituted by hydroxy, $C_1$-$C_8$-alkyl, $C_1$-$C_8$-alkoxy or by a 5- or 6-membered heterocyclic ring having one or more ring hetero atoms selected from the group consisting of oxygen, nitrogen and sulphur, or where $R^1$ is —(C=O)—(NH)$_b$-T where b is 0 and T denotes $C_3$-$C_8$-cycloalkyl or phenyl either of which being optionally substituted by hydroxy, $C_1$-$C_8$-alkyl, $C_1$-$C_8$-alkoxy, or by $C_1$-$C_8$-alkyl substituted by hydroxy, reacting a compound of formula I where $R^1$ is hydrogen with a compound of formula IX

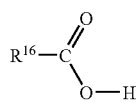

IX where $R^{16}$ is $C_1$-$C_8$-alkyl substituted by a 5- or 6-membered heterocyclic ring having one or more ring hetero atoms selected from the group consisting of oxygen, nitrogen and sulphur, that ring being optionally substituted by $C_1$-$C_8$-alkyl or $C_1$-$C_8$-alkoxy, or $R^{16}$ is a 4-, 5- or 6-membered heterocyclic ring having one or more ring hetero atoms selected from the group consisting of oxygen, nitrogen and sulphur, that ring being optionally substituted by hydroxy, $C_1$-$C_8$-alkyl, $C_1$-$C_8$-alkoxy or by a 5- or 6-membered heterocyclic ring having one or more ring hetero atoms selected from the group consisting of oxygen, nitrogen and sulphur, or $R^{16}$ is $C_3$-$C_8$-cycloalkyl or phenyl either of which being optionally substituted by hydroxy, $C_1$-$C_8$-alkyl, $C_1$-$C_8$-alkoxy, or by $C_1$-$C_8$-alkyl substituted by hydroxy;

(J) for the preparation of compounds of formula I where $R^1$ is $C_1$-$C_8$-alkylaminocarbonyl optionally substituted by halogen, hydroxy, amino, $C_1$-$C_8$-alkylamino, di($C_1$-$C_8$-alkyl)amino, carboxy, $C_1$-$C_8$-alkoxycarbonyl, nitrile, phenyl, $C_1$-$C_8$-haloalkyl, or by $C_1$-$C_8$-alkyl optionally substituted by hydroxy, or $R^1$ is $C_1$-$C_8$-alkylaminocarbonyl optionally substituted by $C_3$-$C_8$-cycloalkyl optionally substituted by hydroxy, or $R^1$ is $C_1$-$C_8$-alkylaminocarbonyl optionally substituted by $C_1$-$C_8$-alkoxy optionally substituted by hydroxy, or $R^1$ is $C_1$-$C_8$-alkylaminocarbonyl optionally substituted by phenyl optionally substituted by hydroxy or $C_1$-$C_8$-alkyl, or $R^1$ is $C_1$-$C_8$-alkylaminocarbonyl optionally substituted by a 5- or 6-membered heterocyclic ring having one or more ring hetero atoms selected from the group consisting of oxygen, nitrogen and sulphur, that ring being optionally substituted by hydroxy, $C_1$-$C_8$-alkyl or $C_1$-$C_8$-alkoxy, or $R^1$ is —(C=O)—(NH)$_a$-Het where a is 1 and Het denotes a 4-, 5- or 6-membered heterocyclic ring having one or more ring hetero atoms selected from the group consisting of oxygen, nitrogen and sulphur, that ring being optionally substituted by hydroxy, $C_1$-$C_8$-alkyl, $C_1$-$C_8$-alkoxy or by a 5- or 6-membered heterocyclic ring having one or more ring hetero atoms selected from the group consisting of oxygen, nitrogen and sulphur, or $R^1$ is —(C=O)—(NH)$_b$-T where b is 1 and T denotes $C_3$-$C_8$-cycloalkyl or phenyl either of which being optionally substituted by hydroxy, $C_1$-$C_8$-alkyl, $C_1$-$C_8$-alkoxy, or by $C_1$-$C_8$-alkyl substituted by hydroxy, reacting a compound of formula X

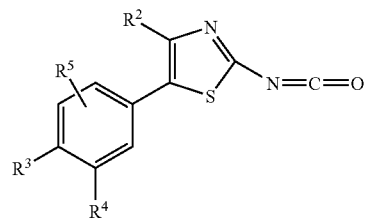

X wherein $R^2$, $R^3$, $R^4$ and $R^5$ are as hereinbefore defined, with a compound of formula XI

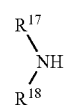

XI where $R^{17}$ and $R^{18}$ are selected from hydrogen, hydroxy, amino, $C_1$-$C_8$-alkylamino, di($C_1$-$C_8$-alkyl(amino), carboxy, $C_1$-$C_8$-alkyl optionally substituted by hydroxy, halogen, $C_3$-$C_8$-cycloalkyl optionally substituted by hydroxy, $C_1$-$C_8$-alkoxy optionally substituted by hydroxy, $C_1$-$C_8$-alkoxycarbonyl, nitrile, halogen, phenyl optionally substituted by hydroxy or $C_1$-$C_8$-alkyl, and a 5- or 6-membered heterocyclic ring having one or more ring hetero atoms selected from the group consisting of oxygen, nitrogen and sulphur, that ring being optionally substituted by hydroxy, $C_1$-$C_8$-alkyl or $C_1$-$C_8$-alkoxy, or when $R^1$ is —(C=O)—(NH)$_a$-Het, $R^{17}$ is hydrogen and $R^{18}$ is a 4-, 5- or 6-membered heterocyclic ring having one or more ring hetero atoms selected from the group consisting of oxygen, nitrogen and sulphur, that ring being optionally substituted by hydroxy, $C_1$-$C_8$-alkyl, $C_1$-$C_8$-alkoxy or by a 5- or 6-membered heterocyclic ring having one or more ring hetero atoms selected from the group consisting of oxygen, nitrogen and sulphur, or when $R^1$ is —(C=O)—(NH)$_b$—T $R^{17}$ is hydrogen and $R_{18}$ is $C_3$-$C_8$-cycloalkyl or phenyl either of which being optionally substituted by hydroxy, $C_1$-$C_8$-alkyl, $C_1$-$C_8$-alkoxy, or by $C_1$-$C_8$-alkyl substituted by hydroxy; or (K) the preparation of compounds of formula I where $R^1$ is hydrogen, hydrolysing a compound of formula I where $R^1$ is $C_1$-$C_8$-alkylcarbonyl; and (ii) recovering the resultant compound of formula I in free or salt form.

Process variant (A) may be carried out using known Suzuki reaction procedures, or analogously, e.g. as hereinafter described in the Examples. It may be carried out in an organic solvent such as dimethoxyethane (DME) usually in the presence of aqueous alkali metal carbonate. The reaction temperature may be from room temperature to 100° C., but conveniently 80° C. The palladium catalyst may be, for example, a bis(triarylphosphine) palladium halide.

Process variant (B) may be carried out using known procedures for preparation of sulphonamides from sulfonyl chlorides, or analogously, e.g. as hereinafter described in the Examples. It may be carried out in an aqueous solvent or an organic solvent, e.g. an ether such as dioxane, usually in the presence of an alkali metal carbonate. The reaction temperature may be from 0° C. to 100° C., but conveniently room temperature.

Process variant (C) may be carried out using known procedures for reaction of amines with sulfonyl chlorides, or analogously, e.g. as hereinafter described in the Examples. It may be carried out in an organic solvent, e.g. dimethylformamide (DMF), usually in the presence of an alkali metal carbonate. The reaction temperature may be from 0° C. to 100° C., but conveniently room temperature.

Process variant (D) may be carried out using known procedures for reaction of aryl halides, ortho to an electron withdrawing group, with primary or secondary amines, or analogously, e.g. as hereinafter described in the Examples. It may be carried out either neat or in an organic solvent, e.g. dimethylsulphoxide. The reaction temperature may be from 100° C. to 170° C. but conveniently about 120° C. to 140° C.

Process variant (E) may be carried out using known procedures for reaction of amines with acylating agents or isocyanates, or analogously, e.g. as hereinafter described in the Examples. It may be carried out in an organic solvent, e.g. dimethylformamide. The reaction temperature may be from 0° C. to 100° C., but conveniently room temperature.

Process variant (F) may be carried out using known procedures for halogenating anilines, or analogously, e.g. as hereinafter described in the Examples. Chlorination may be carried out using hydrogen peroxide, acetic acid and hydrochloric acid, for example as described in S. Mukhopadhyay, K. H. Chandnani and S. B. Chandalia, Organic Process Research & Development, 1999, 3, 196-200. The reaction temperature may be from 0° C. to 50° C., but conveniently room temperature. Mono-bromination may be carried out by reaction with N-bromosuccinimide (NBS) in an organic solvent, preferably dimethylsulphoxide. But mono- or di-bromination may be carried out by reaction with bromine in an organic solvent, e.g. an ether such as dioxane. In both cases the reaction the reaction temperature may be from 0° C. to 50° C., but conveniently room temperature.

Process variant (G) may be carried out using known procedures for preparing aminothiazoles, or analogously, e.g. as hereinafter described in the Examples. The halogen X is preferably bromine. The reaction may be carried out in an organic solvent, e.g. an alcohol such as ethanol. The reaction temperature may be from room temperature to the reflux temperature of the solvent, but conveniently from about 50° C. to 60° C.

Process variant (H) may be carried out using the procedure known in R. W. Brown, Journal of Organic Chemistry, 1991, 56, 4974 for converting sulfonyl halides to sulfones, or analogously, e.g. as hereinafter described in the Examples. It may be carried out with the alkali metal sulphite, e.g. sodium sulphite, and the alkali metal bicarbonate, e.g. sodium bicarbonate in water at a temperature from 20° C. to 100° C., but conveniently at about 75° C. The reaction with bromoacetic acid may be carried out at temperature from 50° C. to 150° C., but conveniently at about 100° C. An alkyl halide, e.g. iodomethane may be used in place of bromoacetic acid Process variant (I) may be carried out using known procedures for reacting amines with carboxylic acids, or analogously, e.g. as hereinafter described in the Examples. The reaction may be carried out in an organic solvent, e.g. dichloromethane, in the presence of a coupling agent, e.g. HATU, and a base, e.g. triethylamine. The reaction temperature may be from 0° C. to 50° C., but conveniently room temperature.

Process variant (J) may be carried out using known procedures for reacting isocyanates with amines, or analogously, e.g. as hereinafter described in the Examples. The reaction may be carried out in an organic solvent, e.g. dioxane or DMF. The reaction temperature may be an elevated temperature, for example from 50° C. to 100° C., but preferably about 80° C.

Process variant (K) may be carried out using known procedures for converting alkylcarbonylamines to amines, or analogously, e.g. as hereinafter described in the Examples. The reaction may be carried out in an organic solvent, e.g. ethanol, in the presence of a base, preferably a strong base such as sodium hydroxide. The reaction temperature may be an elevated temperature, for example from 50° C. to 100° C., but preferably about 90° C.

The compounds of formula I in free or salt form can be recovered from reaction mixtures and purified in a conventional manner. Isomer mixtures can be separated into individual isomers, e.g. enantiomers, in a conventional manner, e.g. by fractional crystallisation.

Compounds of formula II may be prepared by the method known in Garreau, Bull. Soc. Chim. Fr, 1954,1048, or analogously, e.g. as hereinafter described in the Examples.

Compounds of formula III are commercially available.

Compounds of formula IV may be prepared by reacting a compound of formula XII

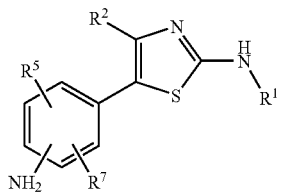

XII wherein $R^1$, $R^2$, $R^5$ and $R^7$ are as hereinbefore defined, with nitrous acid to give a diazo compound which is then reacted with sulphur dioxide in the presence of copper chloride, for example by the method described in E. E. Gilbert, Synthesis 1969, 1-10, to give the corresponding sulfonyl chloride of formula IV.

Compounds of formula IV may also be prepared by reacting a compound of formula XIII

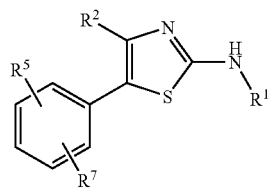

XIII wherein $R^1$, $R^2$, $R^5$ are as hereinbefore defined and $R^7$ is halogen or $OR^{11}$ with chlorosulfonic acid, or analogously, e.g. as described in the Examples.

Compounds of formula V are either available commercially or may be prepared by known methods.

Compounds of formula VI are either available commercially or may be prepared by known methods.

Compounds of formula VII may be prepared by reacting a compound of formula XIV

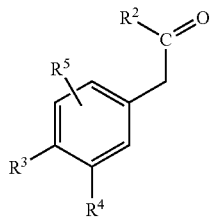

XIV wherein $R^2$, $R^3$, $R^4$ and $R^5$ are as hereinbefore defined, with an halogenating agent, for example bromine, or analogously, e.g. as described in the Examples.

Compounds of formula VIII are commercially available or may be prepared by known methods.

Compounds of formula IX are commercially available or may be prepared by known methods.

Compounds of formula X may be prepared by reacting a compound of formula I wherein $R^1$ is hydrogen with phosgene or analogously, e.g. as described in the Examples.

Compounds of formula XI are commercially available or may be prepared by known methods.

Compounds of formula XII may be prepared by reduction of compounds of formula XV

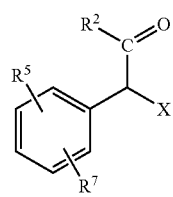

XV wherein $R^1$, $R^2$, $R^5$ and $R^7$ are as hereinbefore defined, using standard techniques known for the reduction of aromatic nitro compounds to anilines, for example catalytic hydrogenation using a transition metal catalyst, preferably palladium on carbon, in an organic solvent, e.g. ethyl acetate, under an atmosphere of hydrogen.

Compounds of formula XIII may be prepared by reacting the corresponding ketone of formula XVI

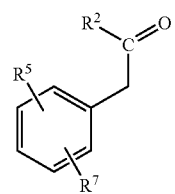

XVI wherein $R^2$, $R^3$, $R^4$ and $R^5$ are as hereinbefore defined and X is halogen, with a compound of formula VIII wherein $R^1$ is as hereinbefore defined, or analogously, e.g. as described in the Examples.

Compounds of formula XIV where either $R^3$ or $R^4$ is independently $SO_2NH_2$ or $SO_2NR^9R^{10}$ may be prepared by reacting a compound of formula XII where $R^1$ and $R^2$ are as hereinbefore defined and one of $R^1$ or $R^7$ is hydrogen, the other being halogen or $OR^{11}$, with chlorosulfonic acid followed by treatment with an amine or ammonia, or analogously, e.g. as described in the Examples.

Compounds of formula XIV may also be obtained from commercially available compounds of formula XVII

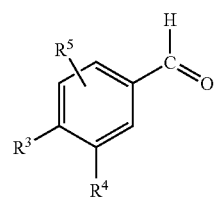

XVII by known methods, for example as described in R. V. Heinzelman, Organic Synthesis 1963, IV, 573.

Compounds of formula XV may be prepared as described in process variant (G) or by known procedures, for example as described in J. Liebscher, E. Mitzner, Synthesis, 1985, 4, 414-417.

Compounds of formula XVI may be prepared by reacting a compound of formula XVIII

XVIII wherein $R^2$, $R^5$, and $R^7$ are as hereinbefore defined, with an halogenating agent, for example bromine, or analogously, e.g. as described in the Examples.

Compounds of formula XVII where $R^3$ is $SO_2CH_3$ are available from commercial sources or may be prepared from compounds of formula XVI where $R^3$ is halogen, for example by the method described in A. Ulman and E. Urankar, J. Org. Chem., 1989, 54, p 4691-4692.

Compounds of formula XVIII are commercially available or may be prepared by known methods.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I and their pharmaceutically acceptable salts, hereinafter referred to alternatively as agents of the invention, are useful as pharmaceuticals. In particular, they exhibit inhibition of phosphatidylinositol 3-kinase (Pi3 kinase) enzymes, especially the gamma isoform (p110γ), which are responsible for generating phosphorylated signalling products. The inhibitory properties of compounds of formula I may be demonstrated in the following test procedures:

Baculovirus expressing different fragments of PI3Kγ fused to GST have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. *Biochem. J.,* 324:489. Residues 38-1102 of human PI3Kγ are subcloned into the BamH1 and EcoR1 sites of the transfer vector pAcG2T (Pharmingen) to create a GST-PI3Kγ lacking the first 37 residues of PI3Kγ. To express the recombinant protein, Sf9 (*Spodoptera frugiperda* 9) insect cells are routinely maintained at densities between $3\times10^5$ and $3\times10^6$ cells/ml in serum containing TNMFH medium (Sigma). Sf9 cells, at a density of $2\times10^6$ are infected with human GST-PI3KγΔ34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells ($1\times10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay was established that measures the transfer of the terminal phosphate of adenosine triphosphate to phosphatidylinositol. The kinase reaction is performed in a white 96 well microtitre plate as a Scintillation Proximity Assay. Each well contains 10 μl test compound in 5% dimethylsulphoxide and 20 μl assay mix (40 mM Tris, 200 mM NaCl, 2 mM ethyleneglycol-aminoethyl-tetraacetic acid (EGTA), 15 μg/ml phosphatidylinositol, 12.5 μM adenosine triphosphate (ATP), 25 mM $MgCl_2$, 0.1 μCi [$^{33}$P]ATP). The reaction is started by the addition of 20 μl of enzyme mix (40 mM Tris, 200 mM NaCl, 2 mM EGTA containing recombinant GST-p110γ). The plate is incubated at room temperature for 60 minutes and the reaction terminated by the adding 150 μl of WGA-bead stop solution (40 mM Tris, 200 mM NaCl, 2 mM EGTA, 1.3 mM ethylene diamine tetraacetic acid (EDTA), 2.6 μM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 μl of 5% dimethylsulphoxide (DMSO) and non-specific activity is determined by adding 10 μl 50 mM EDTA in place of the test compound.

Compounds of the Examples hereinbelow have $IC_{50}$ values below 0.6 μM in the aforementioned assay. For example the compounds of Examples 8, 48, 80, 138, 156, 165 and 178 have $IC_{50}$ values of 0.009, 0.018, 0.013, 0.005, 0.002, 0.019 and 0.040 respectively.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the Pi3 kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy). Other diseases or conditions which may be treated with agents of the invention include septic shock, rheumatoid arthritis, osteoarthritis, proliferative diseases such as cancer, athersclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49-57; Renzi et al, Am. Rev. Respir. Dis. (1993) 148:932-939; Tsuyuki et al., J. Clin. Invest. (1995) 96:2924-2931; and Cernadas et al (1999) Am. J. Respir. Cell Mol. Biol. 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]-sulfonyl]ethyl]-amino]ethyl]-2(3H)-benzothiazolone and pharmaceutically acceptable salts thereof (the hydrochloride being Viozan®—AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), Arofylline (Almirall Prodesfarma) and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially a compound of formula

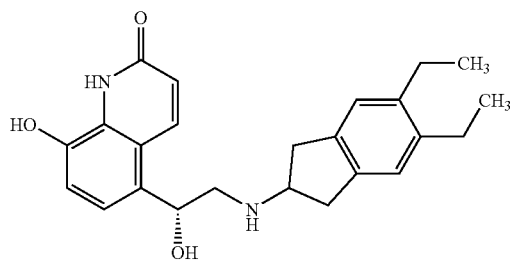

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), and WO 00/66559 (particularly claim 9).

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

EXAMPLES

Compounds of formula I which are also of formula XIX

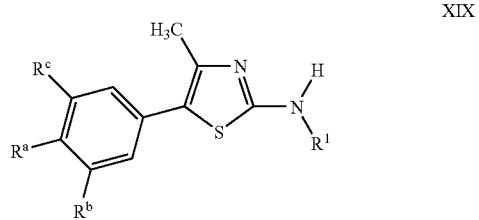

XIX are shown in the Table 1 below, the method of preparation being described thereafter. The table also shows mass spectrometry (MH$^+$) data. The examples are in free form.

TABLE 1

| | Compounds of the invention | | | | |
|---|---|---|---|---|---|
| Ex. | $R^a$ | $R^b$ | $R^c$ | $R^1$ | m/s MH+ |
| 1 | NHSO$_2$CH$_3$ | H | H | ![acetyl CH3 C=O] | 326.1 |
| 2 | NHSO$_2$C$_4$H$_9$ | H | H | ![acetyl CH3 C=O] | 368.1 |
| 3 | ![SO2NH2 group] | H | H | ![acetyl CH3 C=O] | 312.1 |

TABLE 1-continued
Compounds of the invention
| Ex. | R$^a$ | R$^b$ | R$^c$ | R$^1$ | m/s MH+ |
|---|---|---|---|---|---|
| 4 | NH$_2$ | Cl | H | 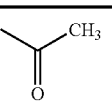 | 282.0 |
| 5 |  | Cl | H |  | 345.9 |
| 6 |  | Cl | Cl |  | 380.0 |
| 7 |  | Br | H |  | 390.1 |
| 8 |  | Br | Br |  | 467.8 |
| 9 |  | Br | Br |  | 466.7 (M − H$^+$) |
| 10 | 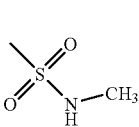 | H | H |  | 326.1 |
| 11 | 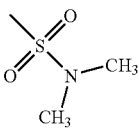 | H | H |  | 340.1 |
| 12 | 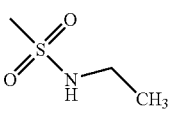 | H | H |  | 340.0 |
| 13 | 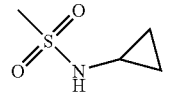 | H | H |  | 352.1 |
| 14 | 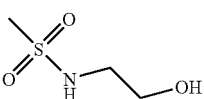 | H | H |  | 356.1 |
| 15 | 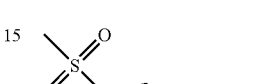 | H | H |  | 365 |
| 16 | 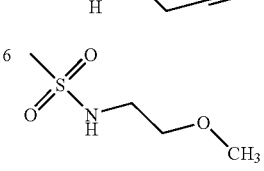 | H | H |  | 370 |

TABLE 1-continued

Compounds of the invention

| Ex. | $R^a$ | $R^b$ | $R^c$ | $R^1$ | m/s MH+ |
|---|---|---|---|---|---|
| 17 | $SO_2CH_3$ | H | H | $COCH_3$ | 311 |
| 18 | $COCH_3$ | H | H | $COCH_3$ | 275.1 |
| 19 | $CF_3$ | H | H | $COCH_3$ | 301 |
| 20 | OH | H | H | $COCH_3$ | 249.1 |
| 21 | $OCH_3$ | $OCH_3$ | H | $COCH_3$ | 293.1 |
| 22 | H | CN | H | $COCH_3$ | 258 |
| 23 | H | $CF_3$ | H | $COCH_3$ | 301 |
| 24 | $SO_2N(CH_3)_2$ | H | H | $CH_3C(O)NHCH_2CH_2C(O)OCH_2CH_3$ | 441.4 |
| 25 | $SO_2N(CH_3)_2$ | H | H | $CH_3C(O)NHCH_2C(O)OCH_2CH_3$ | 427.3 |
| 26 | $SO_2NH_2$ | Cl | Cl | H | 337.8 |
| 27 | $SO_2NH_2$ | Cl | Cl | $CH_3C(O)NHCH_2CH_3$ | 408.9 |
| 28 | $OCH_3$ | $SO_2NH_2$ | H | $CH_3C(O)NHCH_2CH_3$ | 370.9 |

TABLE 1-continued

Compounds of the invention

| Ex. | R$^a$ | R$^b$ | R$^c$ | R$^1$ | m/s MH+ |
|---|---|---|---|---|---|
| 29 | OCH$_3$ | methanesulfonamido-ethanol (S(=O)$_2$-NH-CH$_2$-CH$_2$-OH) | H | -NH-C(=O)-CH$_2$-CH$_3$ | 414.9 |
| 30 | OCH$_3$ | sulfamoyl (S(=O)$_2$-NH$_2$) | H | -C(=O)-CH$_3$ | 341.9 |
| 31 | OCH$_3$ | S(=O)$_2$-NH-CH$_2$-CH$_2$-N(CH$_3$)$_2$ | H | -C(=O)-CH$_3$ | 413.0 |
| 32 | OCH$_3$ | S(=O)$_2$-NH-CH$_2$-CH$_2$-O-CH$_3$ | H | -C(=O)-CH$_3$ | 400.0 |
| 33 | OCH$_3$ | S(=O)$_2$-N(4-methylpiperazinyl) | H | -C(=O)-CH$_3$ | 425.0 |
| 34 | OCH$_3$ | S(=O)$_2$-NH-CH$_2$-CH$_2$-CH$_2$-N(CH$_3$)$_2$ | H | -C(=O)-CH$_3$ | 427.0 |
| 35 | OCH$_3$ | S(=O)$_2$-N(CH$_3$)-CH$_2$-CH$_2$-N(CH$_3$)$_2$ | H | -C(=O)-CH$_3$ | 427.0 |

TABLE 1-continued

Compounds of the invention

| Ex. | R$^a$ | R$^b$ | R$^c$ | R$^1$ | m/s MH+ |
|---|---|---|---|---|---|
| 36 | OCH$_3$ | methanesulfonamido-propyl-morpholine | H | acetyl | 469.0 |
| 37 | OCH$_3$ | methanesulfonamido-propyl-(4-methylpiperazine) | H | acetyl | 482.1 |
| 38 | OCH$_3$ | methanesulfonamido-ethyl-pyrrolidine | H | acetyl | 439.0 |
| 39 | OCH$_3$ | methanesulfonamido-propyl-OCH$_3$ | H | acetyl | 414.0 |
| 40 | OCH$_3$ | methanesulfonamido-ethanol | H | acetyl | 386.0 |
| 41 | OCH$_3$ | dimethylsulfone | H | acetyl | 341.0 |
| 42 | OCH$_3$ | methylsulfonyl-ethanol | H | acetyl | 371.0 |

TABLE 1-continued

Compounds of the invention

| Ex. | R$^a$ | R$^b$ | R$^c$ | R$^1$ | m/s MH+ |
|---|---|---|---|---|---|
| 43 | OCH$_3$ | CH$_3$-S(O)$_2$-CH$_2$CH$_2$CH$_2$-OH | H | C(O)CH$_3$ | 385.1 |
| 44 | OCH$_3$ | CH$_3$-S(O)$_2$-CH$_2$-CN | H | C(O)CH$_3$ | 366.0 |
| 45 | H | CH$_3$-S(O)$_2$-CH$_3$ | H | C(O)CH$_3$ | 310.97 |
| 46 | H | CH$_3$-S(O)$_2$-CH$_2$-CN | H | C(O)CH$_3$ | 335.97 |
| 47 | F | CH$_3$-S(O)$_2$-CH$_3$ | H | C(O)CH$_3$ | 328.97 |
| 48 | Cl | CH$_3$-S(O)$_2$-CH$_3$ | H | C(O)CH$_3$ | 344.94 |
| 49 | H | CH$_3$-S(O)$_2$-NH$_2$ | H | C(O)CH$_3$ | 312.0 |
| 50 | H | CH$_3$-S(O)$_2$-N(piperazinyl)-N-CH$_3$ | H | C(O)CH$_3$ | 395.0 |
| 51 | H | CH$_3$-S(O)$_2$-NH-CH$_2$CH$_2$CH$_2$-N(CH$_3$)$_2$ | H | C(O)CH$_3$ | 397.0 |

TABLE 1-continued

Compounds of the invention

| Ex. | R$^a$ | R$^b$ | R$^c$ | R$^1$ | m/s MH+ |
|---|---|---|---|---|---|
| 52 | H | methylsulfonamido-propyl-morpholine | H | acetyl (COCH$_3$) | 439.0 |
| 53 | H | methylsulfonamido-propyl-OCH$_3$ | H | acetyl (COCH$_3$) | 384.0 |
| 54 | H | methylsulfonamido-ethyl-OH | H | acetyl (COCH$_3$) | 356.0 |
| 55 | H | methylsulfonamido-propyl-N(CH$_3$)$_2$ | H | C(O)NHCH$_2$CH$_3$ | 426.1 |
| 56 | F | SO$_2$NH$_2$ | H | acetyl (COCH$_3$) | 329.97 |
| 57 | Cl | SO$_2$NH$_2$ | H | acetyl (COCH$_3$) | 346.0 |
| 58 | SO$_2$CH$_3$ | H | H | H | 268.9 |
| 59 | SO$_2$CH$_3$ | H | H | C(O)NHCH$_2$CH$_3$ | 340.0 |

TABLE 1-continued

Compounds of the invention

| Ex. | R$^a$ | R$^b$ | R$^c$ | R$^1$ | m/s MH+ |
|---|---|---|---|---|---|
| 60 | CH$_3$SO$_2$ | H | H | -C(O)CH$_3$-NH-CH$_2$-C(O)-O-CH$_2$CH$_3$ (N-acetylglycine ethyl ester) | 398.0 |
| 61 | CH$_3$SO$_2$ | H | H | -C(O)CH$_3$-NH-CH$_2$-C(O)OH (N-acetylglycine) | 370.0 |
| 62 | CH$_3$SO$_2$ | H | H | -C(O)CH$_3$-NH-CH$_2$CH$_2$-C(O)OH | 384.0 |
| 63 | CH$_3$SO$_2$ | Br | H | -C(O)CH$_3$ | 388.8 |
| 64 | CH$_3$SO$_2$ | F | H | -C(O)CH$_3$ | 329.02 |
| 65 | CH$_3$SO$_2$ | CF$_3$ | H | -C(O)CH$_3$ | 378.5 |
| 66 | CH$_3$SO$_2$ | Cl | H | -C(O)CH$_3$ | 344.7 |
| 67 | CH$_3$SO$_2$ | 4-methylpiperazin-1-yl | H | -C(O)CH$_3$ | 409.14 |
| 68 | CH$_3$SO$_2$ | -N(CH$_3$)CH$_2$CH$_2$N(CH$_3$)$_2$ | H | -C(O)CH$_3$ | 411.11 |

TABLE 1-continued

Compounds of the invention

| Ex. | R$^a$ | R$^b$ | R$^c$ | R$^1$ | m/s MH+ |
|---|---|---|---|---|---|
| 69 | methanesulfonyl (CH₃SO₂–) | –NH–CH₂CH₂CH₂–N(CH₃)₂ | H | acetyl (–C(O)CH₃) | 411.14 |
| 70 | methanesulfonyl (CH₃SO₂–) | –NH–CH₂CH₂–N(CH₃)(CH₂CH₃) | H | acetyl (–C(O)CH₃) | 425.02 |
| 71 | methanesulfonyl (CH₃SO₂–) | –N(CH₃)–CH₂CH₂–N(CH₃)(CH₂CH₃) | H | acetyl (–C(O)CH₃) | 439.15 |
| 72 | methanesulfonyl (CH₃SO₂–) | F | H | H | 286.99 |
| 73 | methanesulfonyl (CH₃SO₂–) | F | H | –C(O)NH–CH₂CH₃ | 358.04 |
| 74 | –C(O)OH | H | H | acetyl (–C(O)CH₃) | 277.0 |
| 75 | –C(O)NH–CH₂CH₂OH | H | H | acetyl (–C(O)CH₃) | 320.1 |
| 76 | –C(O)NH–CH₂CH₂–CN | H | H | acetyl (–C(O)CH₃) | 329.1 |

Preparation of Specific Examples

Abbreviations used are as follows: DCM is dichloromethane, DIPEA is diisopropylethylamine DME is dimethoxyethane, HATU is O-(7-azabenzotriazol-1-yl)-N,N,-N',N'-tetramethyl-uronium hexafluorophophate, NBS is N-bromosuccinimide and THF is tetrahydrofuran.

Example 1

N-[5-(4-Methanesulfonylamino-phenyl)-4-methyl-thiazol-2-yl]-acetamide

1a N[5-(4-Amino-phenyl)-4-methyl-thiazol-2-yl]-acetamide

N-[4-Methyl-5-(4-nitro-phenyl)-thiazol-2-yl]-acetamide (J. Liebscher, E. Mitzner, Synthesis, 1985, (4), p 414) (10.0 g, 3.6 mmol) is dissolved in ethyl acetate/THF (5/1, 600 ml) and stirred at room temperature under an atmosphere of argon. The solution is then treated with 10% palladium on carbon (10 g). The reaction mixture is purged three times with nitrogen and placed under an atmosphere of hydrogen overnight. The mixture is then filtered through Celite™ filter material and the catalyst is washed with tetrahydrofuran (600 ml). The solvent is removed in vacuo to leave N-[5-(4-amino-phenyl)-4-methyl-thiazol-2-yl]-acetamide as an off-white solid.

1b) N-[5-(4-Methanesulfonylamino-phenyl)-4-methyl-thiazol-2-yl]-acetamide

N-[5-(4-Amino-phenyl)-4-methyl-thiazol-2-yl]-acetamide (0.05 g, 0.20 mmol) is dissolved in dimethylformamide (1 ml) and treated by a solution of methylsulfonyl chloride (0.0232 g, 0.20 mmol) in dry dimethylformamide (1 ml) followed by 2M aqueous sodium carbonate solution (0.20 ml, 0.40 mmol). The reaction mixture is stirred at room temperature for 18 hours. The solvent is removed in vacuo and the residue is purified by chromatography to give the title compound. MH+ (ESMS): 326.1

Example 2

N-[5-[4-(Butane-1-sulfonlamino)-phenyl]-4-methyl-thiazol-2-yl]-acetamide

This is prepared as described in example 1b by replacing methylsulfonyl chloride with n-butylsulfonyl chloride. MH+ (ESMS): 368.1

Example 3

N-[4-Methyl-5-(4-sulfamoyl-phenyl)-thiazol-2-yl]-acetamide 3a) 4-(2-Acetylamino-4-methyl-thiazol-5-yl)-benzenesulfonyl chloride N-[5-(4-Amino-phenyl)-4-methyl-thiazol-2-yl]-acetamide (Example 1a) (7.9 g, 31.9 mmol) in suspension in glacial acetic acid (250 ml) is treated with a 32% aqueous HCl solution (40 ml). The resulting solution is then cooled approximately to 10° C. and treated dropwise with a solution of sodium nitrite (2.2 g, 31.9 mmol) in water (2 ml). After 10 minutes the reaction mixture is added to a stirred solution of $SO_2$/AcOH/$CuCl_2$/$H_2O$ (200 ml) (the preparation of the reagent is described below). The reaction mixture is allowed to warm to room temperature and is stirred overnight.

The reaction mixture is then poured into water (1000 ml) and extracted with ethyl acetate (3×300 ml). The combined organic layers are washed with water (2×250 ml) followed by brine (200 ml) and dried over $MgSO_4$. After filtration the solvent is removed in vacuo to give 4-(2-acetylamino-4-methyl-thiazol-5-yl)-benzenesulfonyl chloride. MH+ (TOF, MS $ES_+$): 248.1

Preparation of the Reagent $SO_2$/AcOH/$CuCl_2$/$H_2O$

According to the reported procedure (E. E. Gilbert, Synthesis 1969, 1-10, p 6), glacial acetic acid (100 ml) vigorously stirred at room temperature is treated by bubbling $SO_2$ gas. Once a saturated solution is achieved (approximately 10 g per 100 ml), the solution is treated with copper (II) chloride (4 g) in water (5 ml). The resulting mixture is allowed to settle to give a green solution.

3b) N-[4-Methyl-5-(4-sulfamoyl-phenyl)-thiazol-2-yl]-acetamide 4-(2-Acetylamino-4-methyl-thiazol-5-yl)-benzenesulfonyl chloride (3a) (3.8 g, 11.5 mmol) is dissolved in dioxane (50 ml) with stirring. Sodium carbonate (2.45 g, 23 mmol) is added followed by a solution of ammonia in dioxane (50 ml, 0.75 M). After stirring for 2 hours at room temperature diethyl ether (120 ml) is added and the solid precipitate is removed by filtration. The solid is stirred in tetrahydrofuran (200 ml) and the mixture is then filtered through Celite™ filter material to remove inorganic material. Removal of the solvent affords N-[4-methyl-5-(4-sulfamoyl-phenyl)-thiazol-2-yl]-acetamide.

Example 4

N-[5-(4-Amino-3-chloro-phenyl)-4-methyl-thiazol-2-yl]-acetamide

Following a general procedure for chlorination of anilines (S. Mukhopadhyay, K. H. Chandnani, S. B. Chandalia, Organic Process Research & Development, 1999 3, p 196) hydrogen peroxide (27% solution in water, 5.1 ml, 40 mmol) is added dropwise over 30 minutes to N-[5-(4-amino-phenyl)-4-methyl-thiazol-2-yl]-acetamide 1a (5.0 g, 20 mmol) stirred in acetic acid (30 ml) and concentrated hydrochloric acid (6.7 ml) at room temperature. When the addition is complete the mixture is poured onto ice water and the pH adjusted to alkaline by addition of 4M aqueous sodium hydroxide solution. The mixture is then extracted with ethyl acetate, followed by dichloromethane. The combined organic extracts are dried ($MgSO_4$) and the product mixture is absorbed on silica. Chromatography on silica eluting with hexane—ethyl acetate (1:1) affords three fractions: The first fraction is identified as N-[5-(4-amino-3,5-dichloro-phenyl)-4-methyl-thiazol-2-yl]-acetamide (Example 4a). MH+ (TOF, MS ES+) 316.1, 318.1, 320.1. The second fraction is identified as the title compound, N-[5-(4-amino-3-chloro-phenyl)-4-methyl-thiazol-2-yl]-acetamide (Example 4b). MH+ (AP+): 282, 284 (3:1). The third fraction is unreacted starting material (Example 1a).

Examples 5 to 8

These products are obtained in a two step sequence from the corresponding anilines (4a, 4b, 7a, 8a) following analogous conditions to those described for the conversion of N-[5-(4-amino-phenyl)-4-methyl-thiazol-2-yl]-acetamide (Example 1a) to the corresponding sulfonamide (Example 3b).

Example 5

N-[5-(3-Chloro-4-sulfamoyl-phenyl)-4-methyl-thiazol-2-yl]-acetamide

Using N-[5-(4-amino-3-chloro-phenyl)-4-methyl-thiazol-2-yl]-acetamide (Example 4b) affords the title compound as an orange solid. MH+ (TOF, MS ES+) 345.9, 347.9

Example 6

N-[5-(3,5-Dichloro-4-sulfamoyl-phenyl)-4-methyl-thiazol-2-yl]-acetamide

Using N-[5-(4-amino-3,5-dichloro-phenyl)-4-methyl-thiazol-2-yl]-acetamide (Example 4a) affords the product as a white crystalline solid. MH+ (TOF, MS ES+) 380.0, 382.0, 384.0

Example 7

N-[5-(3-Bromo-4-sulfamoyl-phenyl)-4-methyl-thiazol-2-yl]-acetamide

7a) N-[5-(4-Amino-3-bromo-phenyl)-4-methyl-thiazol-2-yl]-acetamide

NBS (2.52 g, 14.7 mmol) is added to a stirred solution of N-[5-(4-amino-phenyl)-4-methyl-thiazol-2-yl]-acetamide (Example 1a) (3.5 g, 14.7 mmol) in dry dimethylsulphoxide (50 ml) at 10° C. After 10 minutes the solution is diluted with water (200 ml) and the resulting precipitate is removed by filtration. Crystallisation from ethyl acetate—methanol affords the title compound. MH+ (TOF, MS ES+): 325.9, 328.9

7b) N-[5-(3-Bromo-4-sulfamoyl-phenyl)-4-methyl-thiazol-2-yl]-acetamide

The title compound is obtained from N-[5-(4-amino-3-bromo-phenyl)-4-methyl-thiazol-2-yl]-acetamide (Example 7a) to give a cream solid. MH+ (TOF, MS ES+) 390.1, 391.1,

Example 8

N-[5-(3,5-Dibromo-4-sulfamoyl-phenyl)-4-methyl-thiazol-2-yl]-acetamide

8a) N-[5-(4-Amino-3,5-dibromo-phenyl)-4-methyl-thiazol-2-yl]-acetamide

Bromine (0.083 ml, 1.6 mmol) is added dropwise over 10 minutes to a stirred solution of N-[5-(4-amino-phenyl)-4-methyl-thiazol-2-yl]-acetamide (Example 1a) (0.20 g, 0.81 mmol) in 1,4-dioxane (5 ml). When the addition is complete the mixture is diluted with saturated sodium hydrogen carbonate solution (30 ml) and extracted with dichloromethane (2×30 ml). The combined organic extracts are dried (MgSO$_4$), filtered, and the solvent removed to give a dark solid. Crystallisation from methanol—dichloromethane yields the tide compound. MH+ (TOF, MS ES+): 403.7, 405.6, 407.6

8b) N-[5-(3,5-Dibromo-4-sulfamoyl-phenyl)-4-methyl-thiazol-2-yl]-acetamide

Using N-[5-(4-amino-3,5-dibromo-phenyl)-4-methyl-thiazol-2-yl]-acetamide (8a) affords the title compound. MH+ (TOF, MS ES+): 467.8, 469.8, 471.8

Example 9

4-(2-Acetylamino-4-methyl-thiazol-5-yl)-2,6-dibromo-benzenesulfonic acid

This compound is obtained as a minor component in the preparation of example 5 from N-[5-(4-amino-3-bromo-phenyl)-4-methyl-thiazol-2-yl]-acetamide; The crude product mixture obtained in the preparation of example 8 is filtered through Celite™ filter material washing with tetrahydrofuran to give N-[5-(3,5-dibromo-4-sulfamoyl-phenyl)-4-methyl-thiazol-2-yl]-acetamide (8). Washing the Celite™ filter material with ethanol then affords the title compound. M-H+(AP−) 466.7, 468.6, 470.6

Example 10

N-[4-Methyl-5-(4-methylsulfamoyl-phenyl)-thiazol-2-yl]-acetamide 4-(2-Acetylamino-4-methyl-thiazol-5-yl)-benzenesulfonyl chloride (Example 3a) (0.05 g, 0.15 mmol) is dissolved in dioxane (1 ml). The solution is treated with 2M aqueous sodium carbonate (0.15 ml, 0.24 mmol) followed by the addition of a 33% solution of methylamine in ethanol (0.08 ml, 0.6 mmol). The reaction mixture is stirred overnight. The solvent is removed in vacuo and the residue is purified by prep LC-MS i.e. liquid chromatography mass spectrometry to give N-[4-Methyl-5-(4-methylsulfamoyl-phenyl)-thiazol-2-yl]-acetamide. MH+ (ESMS): 326.1

Examples 11 to 16

These compounds, namely N-[5-(4-dimethylsulfamoyl-phenyl)-4-methyl-thiazol-2-yl]-acetamide (Mp 279-281° C.), N-[5-(4-ethylsulfamoyl-phenyl)-4-methyl-thiazol-2-yl]-acetamide, N-[5-(4-cyclopropylsulfamoyl-phenyl)-4-methyl-thiazol-2-yl]-acetamide, N-{5-[4-(2-hydroxy-ethylsulfamoyl)-phenyl]-4-methyl-thiazol-2-yl}-acetamide, N-{5-[4-(2-cyano-ethylsulfamoyl)-phenyl]-4-methyl-thiazol-2-yl}-acetamide and N-{5-[4-(2-methoxy-ethylsulfamoyl)-phenyl]-4-methyl-thiazol-2-yl}-acetamide respectively, are prepared in an analogous manner to Example 10 by reaction of the appropriate amine with 4-(2-acetylamino-4-methyl-thiazol-5-yl)-benzenesulfonyl chloride (3a).

Example 17

N-[5-(4-Methanesulfonyl-phenyl)-4-methyl-thiazol-2-yl]-acetamide

17a) N-(4-Methyl-thiazol-2-yl)-acetamide

2-Amino-4-methylthiazole (10.0 g, 87.6 mmol) is dissolved in dry pyridine (75 ml) at room temperature. This solution is then treated dropwise with acetyl chloride (6.3 ml, 87.6 mmol). After 2 hours, the reaction mixture is poured into water (1000 ml), and extracted with ethyl acetate (3×250 ml). The combined organic layers are washed with water (2×200 ml), brine (200 ml), dried over MgSO$_4$, filtered and concentrated in vacuo. The residue is dissolved in toluene (200 ml) followed by the removal of the solvent in vacuo. The solid thus obtained is dried in vacuo to give the title compound.

17b) N-(5-Bromo-4-methyl-thiazol-2-yl)-acetamide

N-(4-Methyl-thiazol-2-yl)-acetamide (Example 17a) (4.0 g, 25.6 mmol) is dissolved in glacial acetic acid (100 ml) at room temperature. This solution is then treated portionwise with N-bromosuccinimide (4.6 g, 25.6 mmol). After 48 hours the reaction mixture is poured into water (1000 ml) and extracted with ethyl acetate (3×250 ml). The combined organic layers are washed with water (200 ml), brine (200 ml), dried over MgSO$_4$, filtered and concentrated in vacuo. The residue is dissolved in toluene (100 ml) followed by the removal of the solvent in vacuo. This is repeated twice more and the resulting solid is dried in vacuo at 40° C. to give N-(5-bromo-4-methyl-thiazol-2-yl)-acetamide.

17c) N-[5-(4-Methanesulfonyl-phenyl)-4-methyl-thiazol-2-yl]-acetamide

N-(5-Bromo-4-methyl-thiazol-2-yl)-acetamide (Example 17b) (0.1 g, 0.43 mmol) is dissolved in DME (2 ml) at room temperature. This solution is treated with [(4-methylsulfonyl)phenyl] boronic acid (0.172 g, 0.86 mmol), followed by 2M aqueous Na$_2$CO$_3$ (0.63 ml, 1.29 mmol) and bis(triphenylphosphine)palladium(II)chloride (0.03 g, 0.043 mmol). The mixture is then heated at 80° C. for 4 hours. The solvent is removed in vacuo and the residue is purified by preparative LCMS to give N-[5-(4-methanesulfonyl-phenyl)-4-methyl-thiazol-2-yl]-acetamide. MH$^+$ (ESMS): 311.0, Mp 251-253° C.

Examples 18 to 23

These compounds, namely N-[5-(4-acetyl-phenyl)-4-methyl-thiazol-2-yl]-acetamide, N-[4-methyl-5-(4-trifluoromethyl-phenyl)-thiazol-2-yl]-acetamide, N-[5-(4-hydroxy-phenyl)-4-methyl-thiazol-2-yl]-acetamide, N-[5-(3,4-dimethoxy-phenyl)-4-methyl-thiazol-2-yl]-acetamide, N-[5-(3-cyano-phenyl)-4-methyl-thiazol-2-yl]-acetamide and N-[4-methyl-5-(3-trifluoromethyl-phenyl)-thiazol-2-yl]-acetamide respectively, are prepared in an analogous manner from the appropriate boronic acid following the procedure described for Example 17.

Example 24

{3-[5-(4-Dimethylsulfamoyl-phenyl)-4-methyl-thiazol-2-yl]-ureido}-acetic acid: ethyl ester

24a) 4-(2-Amino-4-methyl-thiazol-5-yl)-N,N-dimethyl-benzenesulfonamide

Concentrated hydrochloric acid (15 ml) is added to a stirred suspension of N-[5-(4-dimethylsulfamoyl-phenyl)-4-methyl-thiazol-2-yl]-acetamide (example 11) (6.26 g, 18.5 mmol) in ethanol (120 ml). The reaction is heated at 85° C. until no starting material remains (4 hours). The reaction is allowed to cool and the solvent removed to give the hydrochloride salt as a yellow solid. Aqueous sodium hydroxide (4M) is added and the mixture is stirred vigorously for 30 minutes before extracting with chloroform followed by ethyl acetate. The combined organic extracts are dried (MgSO$_4$), filtered and the solvent is removed to give the title compound. MH$^+$ (TOF, MS, ES$_+$): 427.3

24b) {3-[5-(4-Dimethylsulfamoyl-phenyl)-4-methyl-thiazol-2-yl]-ureido}-acetic acid ethyl ester 4-(2-Amino-4-methyl-thiazol-5-yl)-N,N-dimethyl-benzenesulfonamide (Example 24a) (0.083 g, 0.28 mmol) and ethyl isocyanatoacetate (0.05 ml, 0.34 mmol) are stirred in dimethylformamide at 100° C. for 3 hours. The mixture is then partitioned between 1M aqueous hydrochloric acid and ethyl acetate. The organic extract is washed with brine, dried over MgSO$_4$ and the solvent removed in vacuo. Purification by preparative HPLC affords the title compound. MH$^+$ (TOF, MS, ES$_+$): 441.4

Example 25

3-{3-[5-(4-Dimethylsulfamoyl-phenyl)-4-methyl-thiazol-2-yl]-ureido}-propionic acid ethyl ester Using 4-(2-amino-4-methyl-thiazol-5-yl)-N,N-dimethyl-benzenesulfonamide (Example 24a) (0.083 g, 0.28 mmol) and replacing ethyl isocyanatoacetate with ethyl 3-isocyanatopropion-ate (0.05 ml, 0.34 mmol) in the above reaction affords the title compound.

Example 26

4-(2-Amino-4-methyl-thiazol-5-yl)-2,6-dichloro-benzenesulfonamide

A solution of N-[5-(3,5-dichloro-4-sulfamoyl-phenyl)-4-methyl-thiazol-2-yl]-acetamide (Example 6) (0.70 g, 1.84 mmol) in aqueous hydrochloric acid (5M, 10 ml) and ethanol (20 ml) is heated at reflux for 90 minutes. When cool, the mixture is concentrated to remove ethanol and the aqueous solution is brought to pH 9 by addition of aqueous sodium hydroxide (4M). The product is extracted with n-butanol (50 ml) and the organic extract is dried over MgSO$_4$. Removal of the solvent followed by chromatography on silica (eluting with ethyl acetate—hexane, 2:1 increasing to 4:1) affords the title compd. MH$^+$ (MS, AP$^+$): 337.8, 339.5

Example 27

2,6-Dichloro-4-[2-(3-ethyl-ureido)-4-methyl-thiazol-5-yl]-benzenesulfonamide

Ethyl isocyanate (0.015 ml, 0.19 mmol) is added to a stirred solution of 4-(2-amino-4-methyl-thiazol-5-yl)-2,6-dichloro-benzenesulfonamide (Example 26) (0.043 g, 0.127 mmol) in dry dimethylformamide (1.0 ml) under argon. After heating at 85° C. for 3 hours more ethyl isocyanate (0.015 ml, 0.19 mmol) is added and heating continued for a further hour. The reaction is concentrated in vacuo and the product is purified by chromatography on silica eluting with ethyl acetate—hexane (1:1 increasing to 4:1) to give the title compound. MH$^+$ (TOF, MS, ES$^+$): 408.9, 410.9, 412.8

Example 28

5-[2-(3-Ethyl-ureido)-4-methyl-thiazol-5-yl]-2-methoxy-benzenesulfonamide

28a) N-[5-(4-Methoxy-phenyl)-4-methyl-thiazol-2-yl]-acetamide 4-methoxyphenylacetone (10 g, 60.9 mmol), N-acetylthiourea (7.2 g, 60.9 mmol) and iodine (15.46 g, 60.9 mmol) in pyridine (50 ml) are stirred at 70° C. for 16 hours. The mixture is concentrated and the residue is purified by chromatography on silica with iso-hexane-ethyl acetate (1:1) to give the titled compound.

28b) 5-(4-Methoxy-phenyl)-4-methyl-thiazol-2-ylamine

A solution of concentrated hydrochloric acid HCl (20 ml) in water (30 ml) is added to N-[5-(4-Methoxy-phenyl)-4-methyl-thiazol-2-yl]-acetamide (Example 28a) (2 g, 7.63 mmol) in ethanol. After 5 hours at reflux, the reaction is poured into water (600 ml) and the pH is adjusted to 9/10 with 2.5 M NaOH. The aqueous layer is then extracted with ethyl acetate (3×200 ml). The combined organic layers are dried over $MgSO_4$, filtered and concentrated to afford 5-(4-Methoxy-phenyl)-4-methyl-thiazol-2-ylamine.

28c) 1-Ethyl-3-[5-(4-methoxy-phenyl)-4-methyl-thiazol-2-yl]urea

Ethyl isocyanate (1.2 ml, 14.18 mmol) is added to 5-(4-methoxy-phenyl)-4-methyl-thiazol-2-ylamine (Example 28b) (1.56 g, 7.09 mmol) in dioxane (100 ml). After 5 hours at 85° C. the reaction mixture is concentrated to yield 1-ethyl-3-[5-(4-methoxy-phenyl)-4-methyl-thiazol-2-yl]urea as a brown solid.

28d) 5-[2-(3-Ethyl-ureido)-4-methyl-thiazol-5-yl]-2-methoxy-benzenesulfonylchloride A suspension of 1-ethyl-3-[5-(4-methoxy-phenyl)-4-methyl-thiazol-2-yl]urea (Example 28c) (1.0 g, 3.44 mmol) in dichloromethane (15 ml) is added portionwise to chlorosulfonic acid (25 ml, excess) cooled at −10° C. The temperature is kept below 0° C. throughout the addition. The reaction mixture is left to warm up to room temperature. After 3 hours, the reaction mixture is poured carefully onto ice (2 litres). Once ice is melted, the aqueous layer is extracted with dichloromethane (DCM) (3×200 ml). The combined organic layers are washed with brine, dried over $MgSO_4$, filtered and concentrated to afford 5-[2-(3-ethyl-ureido)-4-methyl-thiazol-5-yl]-2-methoxy benzenesulfonylchloride.

28e) 5-[2-(3-Ethyl-ureido)-4-methyl-thiazol-5-yl]-2-methoxy-benzenesulfonamide To a stirred solution of 5-[2-(3-ethyl-ureido)-4-methyl-thiazol-5-yl]-2-methoxy benzenesulfonylchloride (Example 28d) (0.2 g, 0.514 mmol) in dioxane (10 ml) is added 2 M $Na_2CO_3$ (0.515 ml) followed by 0.5 M $NH_3$ in dioxane (2.06 ml). After 2 hours at room temperature, the reaction mixture is poured into water (200 ml) then extracted with ethyl acetate (3×50 ml). The combined organic layers are dried over $MgSO_4$, filtered and concentrated to afford 5-[2-(3-ethyl-ureido)-4-methyl-thiazol-5-yl]-2-methoxy-benzenesulfonamide as a yellow powder.

Example 29

5-[2-(3-Ethyl-ureido)-4-methyl-thiazol-5-yl]-.N.-(2-hydroxy-ethyl)-2-methoxy-benzenesulfonamide To 5-[2-(3-Ethyl-ureido)-4-methyl-thiazol-5-yl]-2-methoxy benzenesulfonylchloride (Example 28d) (0.2 g, 0.514 mmol) in dioxane (10 ml) is added 2M $Na_2CO_3$ (0.515 ml) followed by ethanolamine (0.031 ml, 0.514 mmol). After 2 hours at room temperature, the reaction mixture is poured into water (150 ml)/ethylacetate (50 ml) and sonicated. The layers are separated then the aqueous layer is extracted with ethyl acetate (3×50 ml). The combined organic layers are dried over MgSO4, filtered and concentrated to afford a sticky oil which is dissolved in a minimum amount of DCM/methanol and dried at reduced pressure to afford 5-[2-(3-ethyl-ureido)-4-methyl-thiazol-5-yl]-N-(2-hydroxy-ethyl)-2-methoxy-benzenesulfonamide as a yellow foam.

Example 30

N-[5-(4-Methoxy-3-sulfamoyl-phenyl)-4-methyl-thiazol-2-yl]-acetamide

30a) 2-Methoxy-5-(2-oxo-propyl)-benzenesulfonamide 4-methoxyphenylacetone (5 g, 30 mmol) is added dropwise to chlorosulfonic acid (14.25 ml, 0.21 mol) at below 0° C. and the mixture is stirred at room temperature for 2 hours. The mixture is poured into crushed ice and extracted with ethyl acetate. The ethyl acetate layer is washed with water and dried over $Na_2SO_4$. After removal of the solvent, the residue is dissolved in tetrahydrofuran (50 ml) and concentrated ammonia (8 ml) is added dropwise. The mixture is stirred at room temperature overnight and concentrated. To the residue is added water, the precipitates are collected by filtration and recrystallised from methanol to give the titled compound.

30b) 5-(1-Bromo-2-oxo-propyl)-2-methoxy-benzenesulfonamide

2-Methoxy-5-(2-oxo-propyl)-benzenesulfonamide (Example 30a) (0.5 g, 2.05 mmol) in dry THF (15 ml) is added dropwise to a solution of 2-carboxyethyltriphenylphosphonium perbromide (1.24 g, 2.15 mmol) in dry THF (10 ml). The mixture is stirred at room temperature for 3 hours, filtered and then concentrated. The residue is purified by chromatography on silica with hexane-ethyl acetate (1:1) to give the titled compound.

30c) N-[5-(4-Methoxy-3-sulfamoyl-phenyl)-4-methyl-thiazol-2-yl]-acetamide 5-(1-Bromo-2-oxo-propyl)-2-methoxy-benzenesulfonamide (Example 30b) (0.2 g, 0.64 mmol) and N-acetylthiourea (0.075 g, 0.64 mmol) in ethanol (3 ml) are stirred at 70° C. for 4 hours. The mixture is concentrated and the residue is recrystallised from ethanol to give an off-white solid. $MH^+$ (ESMS): Mp 341.9° C.

Example 31

N-{5-[3-(2-Dimethylamino-ethylsulfamoyl)-4-methoxy-phenyl]-4-methyl-thiazol-2-yl}-acetamide

31a) N-[5-(4-Methoxy-phenyl)-4-methyl-thiazol-2-yl]-acetamide 4-methoxyphenylacetone (10 g, 60.9 mmol), N-acetylthiourea (7.2 g, 60.9 mmol), iodine (15.46 g, 60.9 mmol) in pyridine (50 ml) are stirred at 70° C. for 16 hours. The mixture is concentrated and the residue is purified by chromatography on silica with hexane-ethyl acetate (1:1) to give the titled compound.

31b) N-{5-[3-(2-Dimethylamino-ethylsulfamoyl)-4-methoxy-phenyl]-4-methyl-thiazol-2-yl}-acetamide To N-[5-(4-Methoxy-phenyl)-4-methyl-thiazol-2-yl]-acetamide (Example 28a) (0.0947 g, 0.361 mmol) is added at 0° C. chlorosulfonic acid (3 ml) followed by dichloromethane (1 ml). The reaction mixture is stirred below 0° C. for 2 hours then poured into crushed ice and extracted with dichloromethane (3×5 ml). The organic layers are combined and dried over $MgSO_4$. The solvent is removed to give 5-(2-acetylamino-4-methyl-thiazol-5-yl)-2-methoxy-benzenesulfonyl chloride, which is dissolved into dioxane (2 ml). To this solution is added N,N-dimethyl-ethylenediamine (0.0636 g, 0.72 mmol) and 2M $Na_2CO_3$ (0.5 ml). The reaction mixture is stirred at room temperature for 2 hours. The mixture is concentrated and the residue is taken into water (2 ml) and extracted with dichloromethane (3×5 ml). The combined organic layers are dried over $MgSO_4$. After filtration the solvent is removed in vacuo to give the titled compound which is dried overnight in vacuum oven at 25° C. $MH^+$ (ESMS): Mp 413.0° C.

Examples 32 to 40

These compounds namely N-{5-[4-methoxy-3-(2-methoxy-ethylsulfamoyl)-phenyl]-4-methyl-thiazol-2-yl}-acetamide, N-{5-[4-methoxy-3-(4-methyl-piperazine-1-sulfonyl)-phenyl]-4-methyl-thiazol-2-yl}-acetamide, N-{5-[3-(3-dimethylamino-propylsulfamoyl)-4-methoxy-phenyl]-4-methyl-thiazol-2-yl}-acetamide, N-(5-{3-[(2-dimethylamino-ethyl)-methyl-sulfamoyl]-4-methoxy-phenyl}-4-methyl-thiazol-2-yl)-acetamide, N-{5-[4-methoxy-3-(3-morpholin-4-yl-propylsulfamoyl)-phenyl]-4-methyl-thiazol-2-yl}-acetamide, N-{5-(4-methoxy-3-[3-(4-methyl-piperazin-1-yl)-propylsulfamoyl]-phenyl}-4-methyl-thiazol-2-yl)-acetamide, N-{5-[4-methoxy-3-(2-pyrrolidin-1-yl-ethylsulfamoyl)-phenyl]-4-methyl-thiazol-2-yl}-acetamide, N-{5-[4-methoxy-3-(3-methoxy-propylsulfamoyl)-phenyl]-4-methyl-thiazol-2-yl}-acetamide and N-{5-[3-(2-hydroxy-ethylsulfamoyl)-4-methoxy-phenyl]-4-methyl-thiazol-2-yl}-acetamide respectively, are prepared by replacing N,N-dimethylethylenediamine with the appropriate amine in the above procedure described for the preparation of N-{5-[3-(2-dimethylamino-ethylsulfamoyl)-4-methoxy-phenyl]-4-methyl-thiazol-2-yl}-acetamide (Example 31b) to afford the title compounds.

Example 41

N-[5-(3-Methanesulfonyl-4-methoxy-phenyl)-4-methyl-thiazol-2]-acetamide

41a) 5-(2-Acetylamino-4-methyl-thiazol-5-yl)-2-methoxy-benzenesulfonyl chloride To chlorosulfonic acid (25 ml, excess), cooled at −10° C., is added portionwise a suspension of N-[5-(4-methoxy-phenyl)-4-methyl-thiazol-2-yl]-acetamide (Example 31a) (1.0 g, 3.8 mmol) in DCM (10 ml). The temperature is kept below 0° C. throughout the addition. The reaction mixture is left to warm up to room temperature. After 2 hours, the reaction mixture is poured carefully onto ice (500 ml). Once the ice is melted, the aqueous layer is extracted with DCM (3×200 ml). The combined organic layers are washed with brine (150 ml), dried over $MgSO_4$, filtered and concentrated to afford 5-(2-acetylamino-4-methyl-thiazol-5-yl)-2-methoxybenzene-sulfonyl chloride.

41b) N-[5-(3-Methanesulfonyl-4-methoxy-phenyl)-4-methyl-thiazol-2-yl]-acetamide To a stirred solution of sodium sulfite (1.05 g, 8.31 mmol) and sodium hydrogen carbonate (0.71 g, 8.31 mmol) in water (10 ml) at 70° C. is added a solution of 5-(2-acetylamino-4-methyl-thiazol-5-yl)-2-methoxy-benzenesulfonyl chloride (Example 41a) (1.5 g, 4.16 mmol) in 1,4-dioxane (20 ml). After 30 minutes, the reaction mixture is concentrated to yield the sodium sulfinate intermediate as an off-white solid. To the sulfinate intermediate (0.5 g, 1.43 mmol) in DMF (10 ml) is added iodomethane (0.09 ml, 1.43 mmol). After 2 hours at 40° C., the reaction mixture is poured into water (250 ml) and extracted with ethyl acetate (3×50 ml). The combined organic layers are dried over $MgSO_4$, filtered and concentrated to afford N-[5-(3-methanesulfonyl-4-methoxy-phenyl)-4-methyl-thiazol-2-yl]-acetamide.

Examples 42 to 44

These compounds, namely N-{5-[3-(2-hydroxy-ethanesulfonyl)-4-methoxy-phenyl]-4-methyl-thiazol-2-yl}-acetamide, N-{5-[3-(3-hydroxy-propane-1-sulfonyl)-4-methoxy-phenyl]-4-methyl-thiazol-2-yl}-acetamide, and N-[5-(3-Cyanomethanesulfonyl-4-methoxy-phenyl)-4-methyl-thiazol-2-yl]-acetamide respectively, are synthesised following the same procedure as 41, replacing methyl iodide in the above procedure with the appropriate alkyl iodide

Example 45

N-[5-(3-Methanesulfonyl-phenyl)-4-methyl-thiazol-2-yl]-acetamide

N-[4-Methyl-5-(3-nitro-phenyl)-thiazol-2-yl]-acetamide (Example 49b) is converted into the aniline using the procedure described in Example 1a and this material is converted into the title compound following the procedure described in Example 41b.

Example 46

N-[5-(3-Cyanomethanesulfonyl-phenyl)-4-methyl-thiazol-2-yl]-acetamide

N-[4-Methyl-5-(3-nitro-phenyl)-thiazol-2-yl]-acetamide (49b) is converted into the aniline using the procedure described in Example 1a and this material is converted into the title compound following the procedure described in Example 41b, replacing methyl iodide in this procedure with iodoacetonitrile.

Example 47

N-[5-(4-Fluoro-3-methanesulfonyl-phenyl)-4-methyl-thiazol-2-yl]-acetamide

47a) 2-Fluoro-5-(2-oxo-propyl)-benzenesulfonyl chloride

To chlorosulfonic acid (25 ml, excess) cooled at −10° C. is added dropwise 4-fluorophenyl acetone (1.0 g, 6.57 mmol). The temperature is kept below 0° C. throughout the addition. The reaction mixture is then left to warm up to room temperature overnight. The reaction mixture is poured carefully onto ice (1500 ml). Once ice is melted, the aqueous layer is extracted with DCM (3×250 ml). The combined organic lay-

47b) 1-(4-Fluoro-3-methanesulfonyl-phenyl)-propan-2-one

To a stirred solution of sodium sulfite (0.5 g, 3.99 mmol) and sodium hydrogen carbonate (0.34 g, 3.99 mmol) in water (10 ml) at 70° C. is added a solution of 2-fluoro-5-(2-oxo-propyl)-benzenesulfonyl chloride (Example 47a) (0.5 g, 1.99 mmol) in 1,4-dioxane (20 ml). After 1 hour, the reaction mixture is concentrated to yield the sulfinate intermediate. To the sulfinate intermediate (0.47 g, 1.97 mmol) in DMF (20 ml) is added iodomethane (0.12 ml, 1.97 mmol). After 1 hour at 40° C., the reaction mixture is poured into water (400 ml) and extracted with ethyl acetate (3×100 ml). The combined organic layers are dried over $MgSO_4$, filtered and concentrated. The residue is left overnight in the vacuum oven to afford the titled compound as a viscous oil.

47c) 1-Bromo-1-(4-Fluoro-3-methanesulfonyl-phenyl)-propan-2-one

To 1-(4-fluoro-3-methanesulfonyl-phenyl)-propan-2-one (Example 47b) (0.23 g, 1 mmol) in dry THF (5 ml) is added under inert atmosphere and dropwise a solution of 2-carboxethyltriphenylphosphonium tribromide (0.6 g, 1.05 mmol). After 2.5 hours at room temperature the reaction mixture is filtered then concentrated to give a viscous orange oil which is purified by chromatography eluting with isohexane-ethyl acetate (4:1 then 2:1) to give the titled compound.

47d) N-[5-(4-Fluoro-3-methanesulfonyl-phenyl)-4-methyl-thiazol-2-yl]-acetamide A mixture of 1-bromo-1-(4-fluoro-3-methanesulfonyl-phenyl)-propan-2-one (Example 47c) (0.17 g, 0.55 mmol) and N-acetylthiourea (0.065 g, 0.55 mmol) in ethanol is heated at 70° C. for 3 hours then at room temperature over two days. The reaction mixture is poured into water (200 ml) and extracted with ethyl acetate (3×50 ml). The combined organic layers are dried over $MgSO_4$, filtered and concentrated to afford a viscous solid. This solid in a minimum amount of ethyl acetate is sonicated to give a suspension which is then heated until all solid has dissolved then left to cool to room temperature overnight. The white crystalline solid is filtered off to afford the titled compound.

Example 48

N-[5-(4-Chloro-3-methanesulfonyl-phenyl)-4-methyl-thiazol-2-yl]-acetamide

The title compound is prepared following the same route as N-[5-(4-Fluoro-3-methanesulfonyl-phenyl)-4-methyl-thiazol-2-yl]-acetamide (Example 47) by replacing 4-fluorophenyl acetone with 4-chlorophenyl acetone.

Example 49

N-[4-Methyl-5-(3-sulfamoyl-phenyl)-thiazol-2-yl]-acetamide

49a) 1-Bromo-1-(3-nitro-phenyl)-propan-2-one

A stirred solution of 3-nitrophenylacetone (0.5 g, 13.9 mmol) in THF (10 ml) at room temperature is treated with polymer supported pyridine hydrobromide perbromide (1.4 g, 2 mmol $Br_3^-/g$). The reaction mixture is stirred overnight, then filtered and concentrated in vacuo. The residue is purified by chromatography on silica with iso-hexane-ethyl acetate (6:1) to give the titled compound.

49b) N-[4-Methyl-5-(3-nitro-phenyl)-thiazol-2-yl]-acetamide

A mixture of 1-bromo-1-(3-nitro-phenyl)-propan-2-one (Example 49a) (0.5 g, 1.94 mmol) and N-acetylthiourea (0.23 g, 1.94 mmol) in ethanol (10 ml) is stirred at 70° C. for 2 hours. After cooling the reaction to room temperature, the precipitated product is removed by filtration and dried under vacuum to give the titled compound (0.28 g).

49c) N-[4-Methyl-5-(3-sulfamoyl-phenyl)-thiazol-2-yl]-acetamide

N-[4-Methyl-5-(3-nitro-phenyl)-thiazol-2-yl]-acetamide (Example 49b) is converted into the aniline using the procedure described in Example 1a and this material is converted into the corresponding sulfonamide following the procedure described in Example 3.

Examples 50 to 54

These compounds, namely N-{4-methyl-5-[3-(4-methyl-piperazine-1-sulfonyl)-phenyl]-thiazol-2-yl}-acetamide, N-{5-[3-(3-dimethylamino-propylsulfamoyl)-phenyl]-4-methyl-thiazol-2-yl}-acetamide, N-{4-methyl-5-[3-(3-morpholin-4-yl-propylsulfamoyl)-phenyl]-thiazol-2-yl}-acetamide, N-{5-[3-(3-methoxy-propylsulfamoyl)-phenyl]-4-methyl-thiazol-2-yl}-acetamide and N-{5-[3-(2-hydroxy-ethylsulfamoyl)-phenyl]-4-methyl-thiazol-2-yl}-acetamide respectively, are prepared as described for Example 49 by replacing ammonia in the final reaction with the appropriate amine.

Example 55

N-(3-Dimethylamino-propyl)-3-[2-(3-ethyl-ureido)-4-methyl-thiazol-5-yl]benzenesulfonamide The title compound was prepared from Example 51 using hydrolysis conditions described in example 26 followed by reaction with ethyl isocyanate as described in Example 27.

Example 56

N-[5-(4-Fluoro-3-sulfamoyl-phenyl)-4-methyl-thiazol-2-yl]-acetamide

The title compound is prepared from 4-fluorophenyl acetone via 2-fluoro-5-(2-oxo-propyl)-benzenesulfonyl chloride (Example 47a) following an identical sequence of reactions used for the synthesis of N-[5-(4-methoxy-3-sulfamoyl-phenyl)-4-methyl-thiazol-2-yl]-acetamide (Example 30) from 4-methoxyphenyl acetone.

Example 57

N-[5-(4-Chloro-3-sulfamoyl-phenyl)-4-methyl-thiazol-2-yl]-acetamide

Replacing 4-fluorophenyl acetone with 4-chlorophenyl acetone in the above procedure (Example 56) affords the title compound.

Example 58

5-(4-Methanesulfonyl-phenyl)-4-methyl-thiazol-2-ylamine 4-(2-Acetylamino-4-methyl-thiazol-5-yl)-benzenesulfonyl chloride (Example 3a) (0.5 g, 1.5 mmol) in dioxane (2 ml) is added dropwise to a stirred solution of sodium sulfite (0.378 g, 3.0 mmol) and sodium hydrogen carbonate (0.252 g, 3.0 mmol) in water at 75° C. After 1 hour at 75° C., bromoacetic acid (0.417 g, 3.0 mmol) is added and heating continued for 1 hour at 100° C. Sodium hydroxide (0.24 g, 6.0 mmol) in water (0.25 ml) is then added and the mixture is heated with stirring at 91° C. for 16 hours. The reaction mixture is allowed to cool, diluted with water (100 ml) and extracted with dichloromethane (3×75 ml). The combined organic extracts are washed with brine (75 ml), dried (MgSO$_4$), filtered, and the solvent removed to give the title compound. MH$^+$ 268.9.

Example 59

1-Ethyl-3-[5-(4-methanesulfonyl-phenyl)-4-methyl-thiazol-2-yl]-urea

Ethyl isocyanate (0.09 ml, 1.1 mmol) is added to a stirred solution of 5-(4-methanesulfonyl-phenyl)-4-methyl-thiazol-2-ylamine (Example 58) (0.10 g, 0.37 mmol) in dimethylformamide (1.0 ml). The mixture is heated at 85° C. for 90 minutes followed by removal of the solvent. The residue is crystallised from ethyl acetate—methanol to afford the title compound. MH$^+$ 340.0.

Ex. 60

{3-[5-(4-Methanesulfonyl-phenyl)-4-methyl-thiazol-2-yl]-ureido}-acetic acid ethyl ester Replacing ethyl isocyanate in Example 59 with ethyl isocyanoacetate affords the title compound as a white solid. MH$^+$ 398

Example 61

{3-[5-(4-Methanesulfonyl-phenyl)-4-methyl-thiazol-2-yl]-ureido}-acetic acid Aqueous sodium hydroxide (2M, 0.5 ml) is added to a stirred solution of {3-[5-(4-methanesulfonyl-phenyl)-4-methyl-thiazol-2-yl]-ureido}-acetic acid ethyl ester (Example 60) (0.14 g, 0.00035 mmol) in methanol (2 ml). After stirring at room temperature for 18 hours the solvent is removed and dilute HCl is added. The resulting yellow solid is removed by filtration and recrystallised from ethanol to afford the title compound. MH$^+$ 370.0

Example 62

3-{3-[5-(4-Methanesulfonyl-phenyl)-4-methyl-thiazol-2-yl]-ureido}-propionic acid Replacing ethyl isocyanate in Example 59 with ethyl 3-isocyanatopropionate affords {3-[5-(4-methanesulfonyl-phenyl)-4-methyl-thiazol-2-yl]-ureido}-propionic acid ethyl ester as a white solid. This is treated with aqueous sodium hydroxide for 18 hours as described in Example 61 to afford the title compound as a white solid. MH$^+$ 384.0

Example 63

N-[5-(3-Bromo-4-methanesulfonyl-phenyl)-4-methyl-thiazol-2-yl]-acetamide

N-[5-(4-amino-3-bromo-phenyl)-4-methyl-thiazol-2-yl]-acetamide (Example 7a) (1.0 g, 3.07 mmol) is converted into the corresponding sulfonyl chloride by the procedure described for the conversion of aniline (Example 1a) to sulfonyl chloride (Example 3a). A sample of this crude sulfonyl chloride (1.0 g, 2.4 mmol) is dissolved in dioxane (5 ml) and the resulting solution is added to a stirred solution of sodium sulfite (0.615 g, 4.9 mmol) and sodium hydrogen carbonate (0.41 g, 4.9 mmol) in water (5 ml) at 75° C. After 1 hour at 75° C. bromoacetic acid (0.679 g, 4.9 mmol) is added. The reaction is stirred for an additional 6 hours at 75° C. When cool the mixture is diluted with water (200 ml) and extracted with dichloromethane (3×100 ml). The combined organic extracts are washed with brine (100 ml, dried (MgSO$_4$) and the solvent removed. Purification by chromatography on silica (EtOAc) affords the title compound.

Example 64

N-[5-(3-Fluoro-4-methanesulfonyl-phenyl)-4-methyl-thiazol-2-yl]-acetamide

64a) 3-Fluoro-4-methanesulfonyl-benzaldehyde

Methane sulfinic acid sodium salt (20.1 g, 200 mmol) is added to a stirred solution of 3,4-difluorobenzaldehyde (22.5 g, 158 mmol) in dry DMSO (200 ml) at 75° C. After 2 hours the reaction is poured onto ice-water (200 ml). The precipitate is filtered, washed with water and dissolved in chloroform (400 ml). The organic extract is washed with water (2×200 ml), dried over MgSO$_4$, filtered, and the solvent is removed to give the title compd as a white solid.

64b) 2-Fluoro-1-methanesulfonyl-4-(2-nitro-propenyl)-benzene

A stirred mixture of 3-fluoro-4-methanesulfonyl-benzaldehyde (Example 64a) (24 g, 0.119 mol), nitroethane (70 ml, 0.97 mol) and ammonium acetate (2.75 g, 35 mmol) is heated at reflux under argon for 24 hours. The mixture is concentrated to give an oil which is dissolved in chloroform (200 ml) and washed with water (2×200 ml), followed by brine (100 ml). The organic extract is dried (MgSO$_4$), filtered and the solvent removed to give the product as an orange oil. This was used immediately in the next step.

64c) 1-(3-Fluoro-4-methanesulfonyl-phenyl)-propan-2-one

Iron powder (25 g, 0.45 mol) is added to a stirred mixture of freshly prepared 2-fluoro-1-methanesulfonyl-4-(2-nitropropenyl)-benzene (Example 64b) (29 g, 0.112 mol) in THF (50 ml). Water (110 ml) is added and the mixture is heated to 60° C. Concentrated hydrochloric acid (50 ml) is added slowly over 1 h at 60-90° C. The reaction is then stirred at 100° C. for 20 hours then diluted with cold water (500 ml) and filtered through Celite™ filter material washing with chloroform (500 ml). The organic extract is washed with water (200 ml) followed by brine (200 ml). After drying (MgSO$_4$) the mixture is absorbed on silica and purified by chromatography, eluting with hexane—ethyl acetate (1:1) to give the title compound.

64d) N-[5-(3-Fluoro-4-methanesulfonyl-phenyl)-4-methyl-thiazol-2-yl]-acetamide 1-(3-Fluoro-4-methanesulfonyl-phenyl)-propan-2-one (Example 64c) (1.0 g, 4.34 mmol) is dissolved in dioxane (35 ml) and the solution is cooled to 10° C. at which point the mixture is semi frozen. Bromine (0.067 ml, 1.2 mmol, 0.3 eq.) is added slowly and the mixture is stirred for an additional 15 min in a semi frozen state. The mixture is then allowed to warm to room temperature and the solvent is removed to give a brown oil containing starting material and 1-bromo-1-(3-fluoro-4-methanesulfonyl-phenyl)-propan-2-one. This material is dissolved in ethanol (30 ml) and N-acetylthiourea (0.369 g, 3.1 mmol) is added in one portion. The mixture is stirred at 60° C. for 30 minutes then allowed to cool whereupon the product crystallised. Filtration affords the title compound as a white solid.

Example 65

N-[5-(4-Methanesulfonyl-3-trifluoromethyl-phenyl)-4-methyl-thiazol-2-yl]-acetamide The title compound is prepared by an analogous procedure to N-[5-(3-fluoro-4-methane-sulfonyl-phenyl)-4-methyl-thiazol-2-yl]-acetamide (Example 64) by replacing 3,4-difluoro-benzaldehyde with 3-fluoro-4-trifluoromethylbenzaldehyde.

Example 66

N-[5-(3-Chloro-4-methanesulfonyl-phenyl)-4-methyl-thiazol-2-yl]-acetamide

The title compound is prepared by an analogous procedure to N-[5-(3-fluoro-4-methanesulfonyl-phenyl)-4-methyl-thiazol-2-yl]-acetamide (Example 64) by replacing 3,4-difluorobenzaldehyde with 3,4-dichlorobenzaldehyde.

Example 67

N-{5-[4-Methanesulfonyl-3-(4-methyl-piperazin-1-yl)-phenyl]-4-methyl-thiazol-2-yl}-acetamide A stirred mixture of N-[5-(3-Fluoro-4-methanesulfonyl-phenyl)-4-methyl-thiazol-2-yl]-acetamide (Example 64) (0.05 g, 0.15 mmol) and 1-methylpiperazine (0.1 ml, 0.9 mmol) in dry DMSO (1 ml) is heated under argon at 115° C. for 1 hour. The solvent is removed and water (30 ml) is added. The product is extracted with ethyl acetate (2×30 ml) and the combined organic extracts are washed with brine (20 ml) and dried (MgSO$_4$). Removal of the solvent and trituration with diethyl ether affords the title compound as a yellow solid.

Examples 68 to 71

These compounds, namely N-(5-{3-[(2-dimethylamino-ethyl)-methyl-amino]-4-methane-sulfonyl-phenyl}-4-methyl-thiazol-2-yl)-acetamide, N-{5-[3-(3-dimethylamino-propylamino)-4-methanesulfonyl-phenyl]-4-methyl-thiazol-2-yl}-acetamide, N-{5-[3-(2-diethylamino-ethyl-amino)-4-methanesulfonyl-phenyl]-4-methyl-thiazol-2-yl}-acetamide and N-(5-{3-[(2-diethyl-amino-ethyl)-methyl-amino]-4-methanesulfonyl-phenyl}-4-methyl-thiazol-2-yl)-acetamide respectively, are prepared by the same procedure as Example 67, replacing 1-methylpiperazine in this example with the appropriate amine.

Example 72

5-(3-Fluoro-4-methanesulfonyl-phenyl)-4-methyl-thiazol-2-ylamine

This material is prepared from N-[5-(3-Fluoro-4-methanesulfonyl-phenyl)-4-methyl-thiazol-2-yl]-acetamide (Example 64) using hydrolysis conditions described in Example 26.

Example 73

1-Ethyl-3-[5-(3-fluoro-4-methanesulfonyl-phenyl)-4-methyl-thiazol-2-yl]-urea A mixture of 5-(3-fluoro-4-methanesulfonyl-phenyl)-4-methyl-thiazol-2-ylamine (0.40 g, 1.4 mmol) and ethyl isocyanate (0.121 ml, 1.5 mmol) in dry DMF (3 ml) is heated at 85° C. for 1 hour. The solvent is removed and the product is purified by chromatography on silica eluting with hexane—ethyl acetate (1:1) to give the title compound.

Example 74

4-(2-Acetylamino-4-methyl-thiazol-5-yl)-benzoic acid

74a) 3-(1-Bromo-2-oxo-propyl)-benzoic acid

A stirred solution of 4-(2-oxopropyl)benzoic acid (1.0 g, 5.6 mmol) in THF (30 ml) at room temperature is treated with polymer supported pyridine hydrobromide perbromide (2.8 g, 2 mmol Br$_3^-$/g). After 3 hours at room temperature, the reaction mixture is filtered through Celite™ filter material and the solvent removed under vacuum to give the titled compound.

74b) 4-(2-Acetylamino-4-methyl-thiazol-5-yl)-benzoic acid

A mixture of 3-(1-bromo-2-oxo-propyl)-benzoic acid (1.4 g, 5.4 mmol) and N-acetylthiourea (0.64 g, 5.4 mmol) in ethanol is stirred at 70° C. for 2 hours. The reaction mixture is cooled to room temperature. The precipitated product is removed by and dried under vacuum to give the titled compound.

Example 75

4-(2-Acetylamino-4-methyl-thiazol-5-yl)-N-(2-hydroxy-ethyl)-benzamide

To 4-(2-acetylamino-4-methyl-thiazol-5-yl)-benzoic acid (Example 74b) (0.1 g, 0.36 mmol) in DMF (1 ml) is added HATU (0.14 g, 0.36 mmol) followed by DIPEA (0.07 ml, 0.36 mmol) and ethanolamine (0.022 ml, 0.36 mmol). After 5 hours, the reaction mixture is filtered and the precipitated product is washed with ethanol and dried under vacuum to give the titled compound.

Example 76

4-(2-Acetylamino-4-methyl-thiazol-5-yl)-N-(2-cyano-ethyl)-benzamide

The title compound is prepared following the procedure outlined in Example 75 by replacing ethanolamine with 3-aminopropionitrile.

Agents of the invention also include compounds of formula XIX where R$^a$, R$^b$, R$^c$ and R$^1$ are as shown in the Table 2 below, the method of preparation being described thereafter. The table also shows mass spectrometry (MH$^+$) data. The examples are in free form.

TABLE 2

Compounds of the invention

| Ex. | $R^a$ | $R^b$ | $R^c$ | $R^1$ | ms MH+ |
|---|---|---|---|---|---|
| 77 | -S(O)₂CH₃ | -N(CH₃)CH₂CH₂N(CH₃)CH₃ | H | -C(O)NH-CH₂CH₃ | 440.1 |
| 78 | -S(O)₂CH₃ | H | H | -C(O)CH₂-(1-tetrazolyl) | 378.9 |
| 79 | -S(O)₂CH₃ | H | H | -C(O)CH₂-(3-pyridyl) | 388.0 |
| 80 | -S(O)₂CH₃ | 1-imidazolyl | H | -S(O)₂CH₃ | 377.0 |
| 81 | -S(O)₂CH₃ | 1-(1,2,4-triazolyl) | H | -C(O)CH₃ | 378.0 |
| 82 | -S(O)₂CH₃ | H | H | -C(O)CH₂-(4-pyridyl) | 388.0 |
| 83 | Cl | -S(O)₂CH₃ | H | H | 303.0 |
| 84 | -S(O)₂CH₃ | 4-methyl-1-imidazolyl | H | -C(O)CH₃ | 391.0 |
| 85 | -S(O)₂CH₃ | 2-methyl-1-imidazolyl | H | -C(O)CH₃ | 391.0 |
| 86 | -S(O)₂CH₃ | 2-ethyl-1-imidazolyl | H | -C(O)CH₃ | 405.1 |
| 87 | -S(O)₂CH₃ | 4-methyl-1-pyrazolyl | H | -C(O)CH₃ | 391.1 |

TABLE 2-continued

Compounds of the invention

| Ex. | R$^a$ | R$^b$ | R$^c$ | R$^1$ | ms MH+ |
|---|---|---|---|---|---|
| 88 | S(=O)$_2$CH$_3$ | F | H | -C(=O)NH-CH$_2$CH$_2$-OH | 374.0 |
| 89 | S(=O)$_2$CH$_3$ | F | H | -C(=O)NH-CH$_2$CH$_2$-C≡N | 383.0 |
| 90 | S(=O)$_2$CH$_3$ | S(=O)$_2$CH$_3$ | H | -C(=O)CH$_3$ | 389.0 |
| 91 | S(=O)$_2$CH$_3$ | F | H | -C(=O)NH-CH$_2$CH$_2$CH$_2$-OH | 388.0 |
| 92 | S(=O)$_2$CH$_3$ | F | H | -C(=O)NH-CH$_2$-(2-pyridyl) | 421.0 |
| 93 | S(=O)$_2$CH$_3$ | F | H | -C(=O)NH-CH$_2$CH$_2$-(2-pyridyl) | 435.0 |
| 94 | S(=O)$_2$CH$_3$ | F | H | -C(=O)NH-CH$_2$CH$_2$-(3-pyridyl) | 435.0 |
| 95 | S(=O)$_2$CH$_3$ | F | F | -C(=O)CH$_3$ | 347.1 |
| 96 | S(=O)$_2$CH$_3$ | F | H | -C(=O)NH-CH$_2$CH$_2$CH$_2$CH$_2$-OH | 402.0 |
| 97 | Cl | S(=O)$_2$CH$_3$ | H | -C(=O)NH-CH$_2$CH$_2$CH$_3$ | 388.0 |
| 98 | H | S(=O)$_2$NH-CH$_2$CH$_2$-OH | H | -C(=O)NH-CH$_2$CH$_3$ | 385.0 |

TABLE 2-continued

Compounds of the invention

| Ex. | R$^a$ | R$^b$ | R$^c$ | R$^1$ | ms MH+ |
|---|---|---|---|---|---|
| 99 | Cl | -S(=O)$_2$CH$_3$ | H | -C(=O)NH-CH$_2$-(2-furyl) | 426.0 |
| 100 | Cl | -S(=O)$_2$CH$_3$ | H | -C(=O)NH-CH$_2$CH$_2$-CN | 399.0 |
| 101 | Cl | -S(=O)$_2$CH$_3$ | H | -C(=O)NH-(1,3-dimethylpyrazol-5-yl) | 440.0 |
| 102 | H | Cl | Cl | -C(=O)CH$_3$ | 301.5 |
| 103 | -S(=O)$_2$CH$_3$ | 1-methyl-2-propyl-imidazol-yl | H | -C(=O)CH$_3$ | 419.8 |
| 104 | -S(=O)$_2$CH$_3$ | 1-methyl-2-isopropyl-imidazol-yl | H | -C(=O)CH$_3$ | 419.8 |
| 105 | Cl | -S(=O)$_2$CH$_3$ | H | -C(=O)NH-CH$_2$-(2-pyridyl) | 437.8 |
| 106 | Cl | -S(=O)$_2$CH$_3$ | H | -C(=O)NH-CH(CH$_3$)$_2$ | 388.6 |
| 107 | Cl | -S(=O)$_2$CH$_3$ | H | -C(=O)NH-CH$_2$CH$_2$CH$_2$CH$_3$ | 402.7 |
| 108 | Cl | -S(=O)$_2$CH$_3$ | H | -C(=O)NH-cyclobutyl | 400.7 |
| 109 | Cl | -S(=O)$_2$CH$_3$ | H | -C(=O)-azetidin-1-yl | 386.7 |

TABLE 2-continued

Compounds of the invention

| Ex. | $R^a$ | $R^b$ | $R^c$ | $R^1$ | ms MH+ |
|---|---|---|---|---|---|
| 110 | Cl | S(=O)(=O)CH₃ | H | -C(=O)-NH-CH₂-(4-pyridyl) | 437.7 |
| 111 | Cl | S(=O)(=O)CH₃ | H | -C(=O)-NH-CH₂-(3-pyridyl) | 437.8 |
| 112 | Cl | S(=O)(=O)CH₃ | H | -C(=O)-NH-(CH₂)₃-imidazol-1-yl | 454.9 |
| 113 | Cl | S(=O)(=O)CH₃ | H | -C(=O)-pyrrolidin-1-yl | 400.7 |
| 114 | Cl | S(=O)(=O)CH₃ | H | -C(=O)-NH-CH₂-cyclopropyl | 399.9 |
| 115 | Cl | S(=O)(=O)CH₃ | H | -C(=O)-NH-CH₂CH₂-(1-methylpyrrolidin-2-yl) | 456.9 |
| 116 | Cl | S(=O)(=O)CH₃ | H | -C(=O)-NH-CH₂-(3-furyl) | 425.9 |
| 117 | Cl | S(=O)(=O)CH₃ | H | -C(=O)-NH-CH₂CH₂-OH | 389.9 |
| 118 | Cl | S(=O)(=O)CH₃ | H | -C(=O)-NH-(CH₂)₃-OH | 403.9 |
| 119 | Cl | S(=O)(=O)CH₃ | H | -C(=O)-NH-CH(CH₂OH)(CH₂CH₃) | 417.9 |

TABLE 2-continued

Compounds of the invention

| Ex. | $R^a$ | $R^b$ | $R^c$ | $R^1$ | ms MH+ |
|---|---|---|---|---|---|
| 120 | Cl | S(=O)₂CH₃ | H | acetamido-trans-4-hydroxycyclohexyl | 443.9 |
| 121 | Cl | S(=O)₂CH₃ | H | (S)-N-(1-hydroxypropan-2-yl)acetamide | 403.9 |
| 122 | Cl | S(=O)₂CH₃ | H | (R)-N-(1-hydroxypropan-2-yl)acetamide | 403.9 |
| 123 | Cl | S(=O)₂CH₃ | H | N-(2-(2-hydroxyethoxy)ethyl)acetamide | 433.9 |
| 124 | Cl | S(=O)₂CH₃ | H | N-(3-(diethylamino)propyl)acetamide | 459.0 |
| 125 | Cl | S(=O)₂CH₃ | H | N-(pyridin-3-yl)acetamide | 422.9 |
| 126 | Cl | S(=O)₂CH₃ | H | N-(pyridin-4-yl)acetamide | 422.9 |
| 127 | Cl | S(=O)₂CH₃ | H | N-(1-methyl-1H-pyrazol-5-yl)acetamide | 425.9 |
| 128 | Cl | S(=O)₂CH₃ | H | N-(1,3,5-trimethyl-1H-pyrazol-4-yl)acetamide | 453.9 |

TABLE 2-continued
Compounds of the invention
| Ex. | $R^a$ | $R^b$ | $R^c$ | $R^1$ | ms MH+ |
|---|---|---|---|---|---|
| 129 | Cl |  | H | 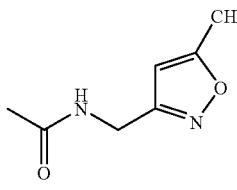 | 440.9 |
| 130 | Cl |  | H | 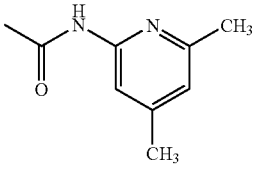 | 450.9 |
| 131 | Cl |  | H | 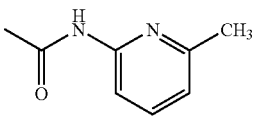 | 436.9 |
| 132 | Cl |  | H | 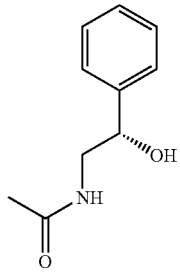 | 465.9 |
| 133 | Cl |  | H | 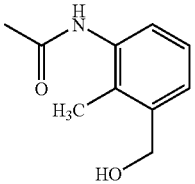 | 465.9 |
| 134 | Cl |  | H | 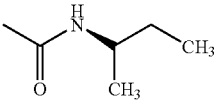 | 401.9 |
| 135 | Cl |  | H | 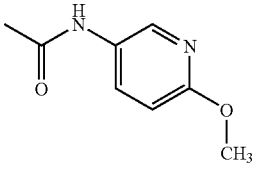 | 452.9 |
| 136 | Cl |  | H | 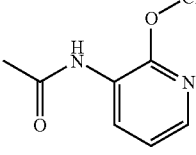 | 452.9 |

TABLE 2-continued
Compounds of the invention
| Ex. | R$^a$ | R$^b$ | R$^c$ | R$^1$ | ms MH+ |
|---|---|---|---|---|---|
| 137 | Cl |  | H | 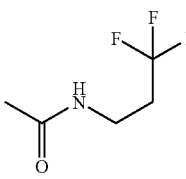 | 441.9 |
| 138 | Cl |  | H |  | 345.8 |
| 139 | Cl |  | H | 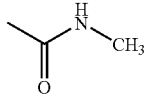 | 359.9 |
| 140 | Cl |  | H | 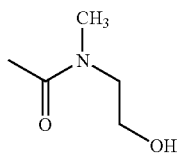 | 403.97 |
| 141 | Cl |  | H | 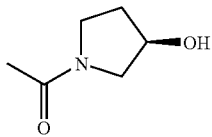 | 415.97 |
| 142 | Cl |  | H | 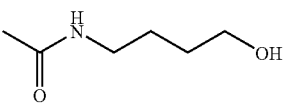 | 417.94 |
| 143 | Cl |  | H | 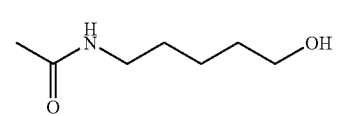 | 431.99 |
| 144 | Cl |  | H | 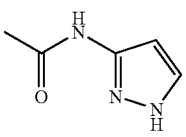 | 411.9 |
| 145 | Cl |  | H | 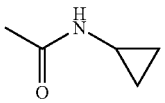 | 386.95 |
| 146 | Cl |  | H | 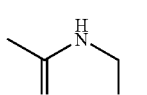 | 373.9 |
| 147 | Cl |  | H | 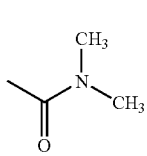 | 373.9 |

TABLE 2-continued

Compounds of the invention

| Ex. | R$^a$ | R$^b$ | R$^c$ | R$^1$ | ms MH+ |
|---|---|---|---|---|---|
| 148 | methanesulfonyl (S(=O)$_2$CH$_3$) | 1-imidazolyl | H | H | 334.9 |
| 149 | methanesulfonyl | 1-methyl-2-propyl-imidazolyl | H | H | 377.0 |
| 150 | methanesulfonyl | 1-imidazolyl | H | -C(=O)NH-CH$_2$CH$_2$-CN | 430.9 |
| 151 | methanesulfonyl | 1-imidazolyl | H | -C(=O)NH-CH$_2$CH$_2$CH$_2$-OH | 435.9 |
| 152 | methanesulfonyl | 1-imidazolyl | H | -C(=O)NH-(CH$_2$)$_4$-OH | 449.9 |
| 153 | methanesulfonyl | 1-imidazolyl | H | -C(=O)NH-CN | 402.9 |
| 154 | methanesulfonyl | 1-imidazolyl | H | -C(=O)N(CH$_3$)-CH$_2$CH$_2$-CN | 444.96 |
| 155 | methanesulfonyl | 1-imidazolyl | H | -C(=O)N(CH$_2$CH$_3$)-CH$_2$CH$_2$-CN | 458.98 |
| 156 | Cl | -S(=O)$_2$-NH-CH$_2$CH$_2$-OH | H | -C(=O)CH$_3$ | 389.9 |

Preparation of Specific Examples

Abbreviations used are as follows: DCM is dichloromethane, DIPEA is diisopropylethylamine DME is dimethoxyethane, HATU is O-(7-azabenzotriazol-1-yl)-N,N,-N', N'-tetramethyl-uronium hexafluorophosphate, NBS is N-bromosuccinimide and THF is tetrahydrofuran.

Example 77

1-(5-{3-[(2-Dimethylamino-ethyl)-methyl-amino]-4-methanesulfonyl-phenyl}-4-methyl-thiazol-2-yl)-3-ethyl-urea A stirred mixture of 1-Ethyl-3-[5-(3-fluoro-4-methanesulfonyl-phenyl)-4-methyl-thiazol-2-yl]-urea (Example 73) (0.05 g, 0.14 mmol) and N,N,N'-Trimethylethylenediamine (0.25 ml, 2.1 mmol) in dry DMSO (0.5 ml) is heated under argon at 120° C. for 2 hours. The solvent is in vacuo removed and the product is purified by chromatography on silica eluting with ethanol-triethylamine (98:1) to give the titled compound. MH$^+$: 440.1051

Example 78

N-[5-(4-Methanesulfonyl-phenyl)-4-methyl-thiazol-2-yl]-2-tetrazol-1-yl-acetamide 5-(4-Methanesulfonyl-phenyl)-4-methyl-thiazol-2-ylamine (Example 58) (0.08 g, 0.3 mmol) is added to a solution of HATU (0.113 g, 0.3 mmol) and 1-tetrazole acetic acid (0.039 g, 0.31 mmol) in DCM. Triethylamine (0.104 ml, 0.75 mmol) is then added and the reaction mixture is left to stir at room temperature overnight. The product is purified by chromatography on silica eluting with methanol—DCM (96:4) to give the titled compound.

Example 79

N-[5-(4-Methanesulfonyl-phenyl)-4-methyl-thiazol-2-yl]-2-pyridin-3-yl-acetamide

This is prepared as described in Example 78 by replacing 1-tetrazole acetic acid with 3-pyridineacetic acid.

Example 82

N-[5-(4-Methanesulfonyl-phenyl)-4-methyl-thiazol-2-yl]-2-pyridin-4-yl-acetamide

This is prepared as described in Example 78 by replacing 1-tetrazole acetic acid with 4-pyridineacetic acid.

Example 80

N-[5-(3-Imidazol-1-yl-4-methanesulfonyl-phenyl)-4-methyl-thiazol-2-yl]-acetamide A stirred mixture of N-[5-(3-Fluoro-4-methanesulfonyl-phenyl)-4-methyl-thiazol-2-yl]-acetamide (Example 64) (0.1 g, 0.30 mmol), imidazole (0.069 g, 0.90 mmol) and caesium carbonate (0.198 g, 0.60 mmol) in dry DMSO is heated under argon at 140° C. for 2 hours. The solvent is removed and water (30 ml) is added. The product is extracted with ethyl acetate (2×30 ml) and the combined organic extracts are washed with brine (20 ml) and dried (MgSO$_4$). Removal of the solvent and trituration with methanol affords the titled compound as an orange solid. MH$^+$: 377.9721

Examples 81, 84 to 87, 103 and 104

The compounds, namely N-[5-(4-methanesulfonyl-3-[1,2,4]triazol-1-yl-phenyl)-4-methyl-thiazol-2-yl]-acetamide, N-{5-[4-methanesulfonyl-3-(4-methyl-imidazol-1-yl)-phenyl]-4-methyl-thiazol-2-yl}-acetamide, N-{5-[4-methanesulfonyl-3-(2-methyl-imidazol-1-yl)-phenyl]-4-methyl-thiazol-2-yl]-acetamide, N-{5-[3-(2-ethyl-imidazol-1-yl)-4-methanesulfonyl-phenyl]-4-methyl-thiazol-2-yl}-acetamide, N-{5-[4-methanesulfonyl-3-(4-methyl-pyrazol-1-yl)-phenyl]-4-methyl-thiazol-2-yl}-acetamide, N-{5-[4-methanesulfonyl-3-(2-propyl-imidazol-1-yl)-phenyl]-4-methyl-thiazol-2-yl}-acetamide and N-{5-[3-(2-isopropyl-imidazol-1-yl)-4-methanesulfonyl-phenyl]-4-methyl-thiazol-2-yl}-acetamide respectively, are prepared by the same procedure as Example 80 replacing 1-methylpiperazine in this example with the appropriate 5-membered ring nitrogen heterocycle.

Example 83

5-(4-Chloro-3-methanesulfonyl-phenyl)-4-methyl-thiazol-2-ylamine

This compound is made via an analogous procedure to N-[5-(4-Chloro-3-methanesulfonyl-phenyl)-4-methyl-thiazol-2-yl]-acetamide (Ex. 48) by replacing N-acetylthiourea with thiourea.

Example 88

1-[5-(3-Fluoro-4-methanesulfonyl-phenyl)-4-methyl-thiazol-2-yl]-3-(2-hydroxy-ethyl)-urea 88a) 5-(3-fluoro-4-methanesulfonyl-phenyl)-2-isocyanato-4-methyl-thiazole 5-(3-Fluoro-4-methanesulfonyl-phenyl)-4-methyl-thiazol-2-ylamine (Example 72) (1.74 mmol, 0.5 g) is added to acetonitrile (15 ml) and treated with phosgene (20% solution in toluene, 6.99 mmol, 3.7 ml). The reaction mixture is heated to reflux (85° C.) for 30 minutes. After cooling to room temperature the solvent is removed in vacuo to leave 5-(3-fluoro-4-methanesulfonyl-phenyl)-2-isocyanato-4-methyl-thiazole as an orange solid.

88b) 1-[5-(3-Fluoro-4-methanesulfonyl-phenyl)-4-methyl-thiazol-2-yl]-3-(2-hydroxy-ethyl)-urea 5-(3-fluoro-4-methanesulfonyl-phenyl)-2-isocyanato-4-methyl-thiazole (88a)(0.58 mmol, 0.183 g) is dissolved in dioxane (5 ml) and treated with 2-aminoethanol (0.64 mmol, 0.039 ml) under argon. The reaction mixture is stirred and heated to 80° C. for 1 hour. The solvent is then removed and the residue dissolved in EtOAc and washed with water (2×20 ml) followed by brine (20 ml) and dried over MgSO$_4$. After filtration, the solvent is removed in vacuo and the residue purified by chromatography on silica eluting with ethyl acetate—methanol (9:1) to give the title compound.

Examples 89, 91 to 94 and 96

These compounds, namely 1-(2-cyano-ethyl)-3-[5-(3-fluoro-4-methanesulfonyl-phenyl)-4-methyl-thiazol-2-yl]-urea, 1-[5-(3-fluoro-4-methanesulfonyl-phenyl)-4-methyl-thiazol-2-yl]-3-(3-hydroxy-propyl)-urea, 1-[5-(3-fluoro-4-methanesulfonyl-phenyl)-4-methyl-thiazol-2-yl]-3-pyridin- 2-ylmethyl-urea, 1-[5-(3-fluoro-4-methanesulfonyl-phenyl)-4-methyl-thiazol-2-yl]-3-pyridin-2-yl-ethyl)-urea, 1-[5-(3-Fluoro-4-methanesulfonyl-phenyl)-4-methyl-thiazol-2-yl]-3-(2-pyridin-3-yl-ethyl)-urea and 1-[5-(3-Fluoro-4-methanesulfonyl-phenyl)-4-methyl-thiazol-2-yl]-3-(4-hydroxy-butyl)-urea respectively are prepared by the same procedure as Example 88 replacing 2-aminoethanol (part 88b) in this example with the appropriate amine.

Examples 97, 99 to 101 and 105 to 116

The compounds namely, 1-[5-(4-chloro-3-methanesulfonyl-phenyl)-4-methyl-thiazol-2-yl]-3-propyl-urea, 1-[5-(4-chloro-3-methanesulfonyl-phenyl)-4-methyl-thiazol-2-yl]-3-furan-2-ylmethyl-urea, 1-[5-(4-chloro-3-methanesulfonyl-phenyl)-4-methyl-thiazol-2-yl]-3-(2-cyano-ethyl)-urea, 1-[5-(4-chloro-3-methanesulfonyl-phenyl)-4-methyl-thiazol-2-yl]-3-(2,5-dimethyl-2H-pyrazol-3-yl)-urea, 1-[5-(4-chloro-3-methanesulfonyl-phenyl)-4-methyl-thiazol-2-yl]-3-pyridin-2-ylmethyl-urea, 1-[5-(4-chloro-3-methanesulfonyl-phenyl)-4-methyl-thiazol-2-yl]-3-isopropyl-urea, 1-butyl-3-[5-(4-chloro-3-methanesulfonyl-phenyl)-4-methyl-thiazol-2-yl]-urea, 1-[5-(4-chloro-3-methanesulfonyl-phenyl)-4-methyl-thiazol-2-yl]-3-cyclobutyl-urea, azetidine-1-carboxylic acid [5-(4-chloro-3-methanesulfonyl-phenyl)-4-methyl-thiazol-2-yl]-amide, 1-[5-(4-chloro-3-methanesulfonyl-phenyl)-4-methyl-thiazol-2-yl]-3-pyridin-4-ylmethyl-urea, 1-[5-(4-chloro-3-methanesulfonyl-phenyl)-4-methyl-thiazol-2-yl]-3-pyridin-3-ylmethyl-urea, 1-[5-(4-chloro-3-methanesulfonyl-phenyl)-4-methyl-thiazol-2-yl]-3-(3-imidazol-1-yl-propyl)-urea, pyrrolidine-1-carboxylic acid [5-(4-chloro-3-methanesulfonyl-phenyl)-4-methyl-thiazol-2-yl]-amide, 1-[5-(4-chloro-3-methanesulfonyl-phenyl)-4-methyl-thiazol-2-yl]-3-cycopropylmethyl-urea, 1-[5-(4-chloro-3-methanesulfonyl-phenyl)-4-methyl-thiazol-2-yl]-3-[2-(1-methyl-pyrrolidin-2-yl)-ethyl]-urea, 1-[5-(4-chloro-3-methanesulfonyl-phenyl)-4-methyl-thiazol-2-yl]-3-furan-3-ylmethyl-urea respectively are prepared by the same procedure as Example 88 replacing 5-(3-fluoro-4-methanesulfonyl-phenyl)-4-methyl-thiazol-2-ylamine (Example 72) with 5-(4-chloro-3-methanesulfonyl-phenyl)-4-methyl-thiazol-2-ylamine (Example 83) and by replacing 2-aminoethanol (part 88b) with the appropriate amine.

Examples 117 to 147

The compounds namely, 1-[5-(4-chloro-3-methanesulfonyl-phenyl)-4-methyl-thiazol-2-yl]-3-(2-hydroxy-ethyl)-urea, 1-[5-(4-chloro-3-methanesulfonyl-phenyl)-4-methyl-thiazol-2-yl]-3-(3-hydroxy-propyl)-urea, 1-[5-(4-chloro-3-methanesulfonyl-phenyl)-4-methyl-thiazol-2-yl]-3-((S)-1-hydroxymethyl-propyl)-urea, 1-[5-(4-chloro-3-methanesulfonyl-phenyl)-4-methyl-thiazol-2-yl]-3-(4-hydroxy-cyclohexyl)-urea, 1-[5-(4-chloro-3-methanesulfonyl-phenyl)-4-methyl-thiazol-2-yl]-3-((R)-2-hydroxy-1-methyl-ethyl)-urea, 1-[5-(4-chloro-3-methanesulfonyl-phenyl)-4-methyl-thiazol-2-yl]-3-((S)-2-hydroxy-1-methyl-ethyl)-urea, 1-[5-(4-chloro-3-methanesulfonyl-phenyl)-4-methyl-thiazol-2-yl]-3-[2-(2-hydroxy-ethoxy)-ethyl]-urea, 1-[5-(4-chloro-3-methane-sulfonyl-phenyl)-4-methyl-thiazol-2-yl]-3-(3-diethylamino-propyl)-urea, 1-[5-(4-chloro-3-methanesulfonyl-phenyl)-4-methyl-thiazol-2-yl]-3-pyridin-3-yl-urea, 1-[5-(4-chloro-3-methane-sulfonyl-phenyl)-4-methyl-thiazol-2-yl]-3-pyridin-4-yl-urea, 1-[5-(4-chloro-3-methanesulfonyl-phenyl)-4-methyl-thiazol-2-yl]-3-(2-methyl-2H-pyrazol-3-yl)-urea, 1-[5-(4-chloro-3-methane-sulfonyl-phenyl)-4-methyl-thiazol-2-yl]-3-(1,3,5-trimethyl-1H-pyrazol-4-yl)-urea, 1-[5-(4-chloro-3-methanesulfonyl-phenyl)-4-methyl-thiazol-2-yl]-3-(5-methyl-isoxazol-3-ylmethyl)-urea, 1-[5-(4-chloro-3-methanesulfonyl-phenyl)-4-methyl-thiazol-2-yl]-3-(4,6-dimethyl-pyridin-2-yl)-urea, 1-[5-(4-chloro-3-methanesulfonyl-phenyl)-4-methyl-thiazol-2-yl]-3-(6-methyl-pyridin-2-yl)-urea, 1-[5-(4-chloro-3-methanesulfonyl-phenyl)-4-methyl-thiazol-2-yl]-3-((S)-2-hydroxy-2-phenyl-ethyl)-urea, 1-[5-(4-chloro-3-methanesulfonyl-phenyl)-4-methyl-thiazol-2-yl]-3-(3-hydroxymethyl-2-methyl-phenyl)-urea, 1-((R)-sec-butyl)-3-[5-(4-chloro-3-methane-sulfonyl-phenyl)-4-methyl-thiazol-2-yl]-urea, 1-[5-(4-chloro-3-methanesulfonyl-phenyl)-4-methyl-thiazol-2-yl]-3-(6-methoxy-pyridin-3-yl)-urea, 1-[5-(4-chloro-3-methane-sulfonyl-phenyl)-4-methyl-thiazol-2-yl]-3-(2-methoxy-pyridin-3-yl)-urea, 1-[5-(4-chloro-3-methane-sulfonyl-phenyl)-4-methyl-thiazol-2-yl]-3-(3,3,3-trifluoro-propyl)-urea, [5-(4-chloro-3-methanesulfonyl-phenyl)-4-methyl-thiazol-2-yl]-urea, 1-[5-(4-chloro-3-methanesulfonyl-phenyl)-4-methyl-thiazol-2-yl]-3-methyl-urea, 3-[5-(4-chloro-3-methanesulfonyl-phenyl)-4-methyl-thiazol-2-yl]-1-(2-hydroxy-ethyl)-1-methyl-urea, (R)-3-hydroxy-pyrrolidine-1-carboxylic acid [5-(4-chloro-3-methanesulfonyl-phenyl)-4-methyl-thiazol-2-yl]-amide, 1-[5-(4-chloro-3-methanesulfonyl-phenyl)-4-methyl-thiazol-2-yl]-3-(4-hydroxy-butyl)-urea, 1-[5-(4-chloro-3-methanesulfonyl-phenyl)-4-methyl-thiazol-2-yl]-3-(5-hydroxy-pentyl)-urea, 1-[5-(4-chloro-3-methanesulfonyl-phenyl)-4-methyl-thiazol-2-yl]-3-(1H-pyrazol-3-yl)-urea, 1-[5-(4-chloro-3-methanesulfonyl-phenyl)-4-methyl-thiazol-2-yl]-3-cyclopropyl-urea, 1-[5-(4-chloro-3-methanesulfonyl-phenyl)-4-methyl-thiazol-2-yl]-3-ethyl-urea and 3-[5-(4-chloro-3-methane-sulfonyl-phenyl)-4-methyl-thiazol-2-yl]-1,1-dimethyl-urea respectively, are prepared by the same procedure as Example 88 replacing 2-aminoethanol (part 88b) in this example with the appropriate amine and by replacing dioxane with dimethyl formamide.

Example 90

N-[5-(3,4-Bis-methanesulfonyl-phenyl)-4-methyl-thiazol-2-yl]-acetamide

This is isolated as a minor by product in the synthesis of N-[5-(3-Fluoro-4-methanesulfonyl-phenyl)-4-methyl-thiazol-2-yl]-acetamide (Example 64) when excess methane sulfinic acid sodium salt is added in the first step of the synthesis (64a). The resulting aldehyde is converted into the title compound by the procedure described in parts 64b-d.

Example 95

N-[5-(3,5-Difluoro-4-methanesulfonyl-phenyl)-4-methyl-thiazol-2-yl]-acetamide

The title compound is made via an analogous procedure to N-[5-(3-Fluoro-4-methanesulfonyl-phenyl)-4-methyl-thiazol-2-yl]-acetamide (Example 64) by replacing 3,4-difluorobenzaldehyde in part 64a of the procedure with 3,4,5-trifluorobenzaldehyde.

Example 98

3-[2-(3-Ethyl-ureido)-4-methyl-thiazol-5-yl]-N-(2-hydroxy-ethyl)-benzenesulfonamide

98a) 1-Bromo-1-(3-nitro-phenyl)-propan-2-one

A stirred solution of 3-nitrophenylacetone (2.5 g, 14.0 mmol) in dry THF (50 ml) at room temperature is treated with polymer supported pyridine hydrobromide perbromide (7.0 g, 14.0 mmol) and left to stir overnight. The reaction mixture is then filtered and the solvent removed in vacuo. The residue is purified by chromatography on silica eluting with 1:4 ethyl acetate—hexane to give the titled compound.

98b) 4-Methyl-5-(3-nitro-phenyl)-thiazol-2-ylamine

A stirred solution of 1-Bromo-1-(3-nitro-phenyl)-propan-2-one (98a) (2.4 g, 9.3 mmol) in ethanol (20 ml) at room temperature is treated with thiourea (0.71 g, 9.3 mmol). The reaction mixture is heated to 70° C. for 10 minutes. The resulting precipitate is removed by filtration and dried under vacuum to give the titled compound.

98c) 1-Ethyl-3-[4-methyl-5-(3-nitro-phenyl)-thiazol-2-yl]-urea

The title compound is made via an analogous procedure to Example 88 by, first of all, replacing 5-(3-Fluoro-4-methanesulfonyl-phenyl)-4-methyl-thiazol-2-ylamine (part 88a) with 4-Methyl-5-(3-nitro-phenyl)-thiazol-2-ylamine and secondly, by replacing 2-aminoethanol with ethylamine (part 88b).

98d) 1-[5-(3-amino-phenyl)-4-methyl-thiazol-2-yl]-3-ethyl-urea

A stirred solution of 1-Ethyl-3-[4-methyl-5-(3-nitro-phenyl)-thiazol-2-yl]-urea (98c) (0.55 g, 1.8 mmol) in THF (25 ml) and EtOAc (50 ml) under Argon is treated with 10% palladium on carbon (1.0 g). The reaction mixture was placed under an atmosphere of hydrogen for 2 hours. The mixture was then filtered through Celite™ filter material and the solvent removed in vacuo to yield the titled compound.

98e) 3-[2-(3-Ethyl-ureido)-4-methyl-thiazol-5-yl]-N-(2-hydroxy-ethyl)-benzenesulfonamide The titled compound is made via an analogous procedure to N-[4-methyl-5-(4-sulfamoyl-phenyl)-thiazol-2-yl]-acetamide (Example 3) by replacing N-[5-(4-amino-phenyl)-4-methyl-thiazol-2-yl]-acetamide with 1-[5-(3-amino-phenyl)-4-methyl-thiazol-2-yl]-3-ethyl-urea (part 3a) and by replacing ammonia with ethanolamine (part 3b).

Example 102

N-[5-(3,5-Dichloro-phenyl)-4-methyl-thiazol-2-yl]-acetamide

The title compound is made via an analogous procedure to N-[5-(3-Fluoro-4-methanesulfonyl-phenyl)-4-methyl-thiazol-2-yl]-acetamide (Example 64d) by replacing 1-(3-Fluoro-4-methanesulfonyl-phenyl)-propan-2-one with 1-(3,5-Dichloro-phenyl)-propan-2-one.

Example 148

5-(3-Imidazol-1-yl-4-methanesulfonyl-phenyl)-4-methyl-thiazol-2-ylamine

A stirred solution of N-[5-(3-imidazol-1-yl-4-methanesulfonyl-phenyl)-4-methyl-thiazol-2-yl]-acetamide (Example 80) (0.80 g, 2.13 mmol) in ethanol (15 ml) and 7M aqueous HCl (20 ml) is heated at 90° C. for 2 hours. The solution is allowed to cool, brought to pH 10 by addition of aqueous NaOH and extracted with n-butanol. The organic extract is dried (MgSO$_4$), the solvent is removed and the residue is triturated with ethanol to give the titled compound as a yellow solid.

Ex. 149

5-[4-Methanesulfonyl-3-(2-propyl-imidazol-1-yl)-phenyl]-4-methyl-thiazol-2-ylamine This is prepared by an analogous procedure to Ex. 148, replacing N-[5-(3-imidazol-1-yl-4-methanesulfonyl-phenyl)-4-methyl-thiazol-2-yl]-acetamide (example 4) with N-{5-[4-methane-sulfonyl-3-(2-propyl-imidazol-1-yl)-phenyl]-4-methyl-thiazol-2-yl}-acetamide (Ex. 103).

Example 150

1-(2-Cyano-ethyl)-3-[5-(3-imidazol-1-yl-4-methanesulfonyl-phenyl)-4-methyl-thiazol-2-yl]-urea

150a) Imidazole-1-carboxylic acid [5-(3-imidazol-1-yl-4-methanesulfonyl-phenyl)-4-methyl-thiazol-2-yl]-amide Sodium hydride (60% dispersion in oil, 0.137 g, 3.42 mmol) is added to a stirred suspension of 5-(3-Imidazol-1-yl-4-methanesulfonyl-phenyl)-4-methyl-thiazol-2-ylamine (148) (1.04 g, 3.1 mmol) in dry dimethylformamide (10 ml) at room temperature under argon. 1,1'-Carbonyl diimidazole (0.757 g, 4.67 mmol) is added and the stirred suspension is heated to 40° C. for 1 h. The reaction mixture is cooled and the resulting solid filtered and washed with DCM and ether to afford the title compound.

150b) 1-(2-Cyano-ethyl)-3-[5-(3-imidazol-1-yl-4-methanesulfonyl-phenyl)-4-methyl-thiazol-2-yl]-urea The titled compound is prepared by the same procedure as example 88, replacing 2-aminoethanol (part 88b) in this example with 3-aminopropionitrile and replacing 5-(3-fluoro-4-methanesulfonyl-phenyl)-2-isocyanato-4-methyl-thiazole (88a) with Imidazole-1-carboxylic acid [5-(3-imidazol-1-yl-4-methanesulfonyl-phenyl)-4-methyl-thiazol-2-yl]-amide (150a)

Examples 151 to 155

These compounds, namely 1-(3-hydroxy-propyl)-3-[5-(3-imidazol-1-yl-4-methanesulfonyl-phenyl)-4-methyl-thiazol-2-yl]-urea, 1-(4-hydroxy-butyl)-3-[5-(3-imidazol-1-yl-4-methane-sulfonyl-phenyl)-4-methyl-thiazol-2-yl]-urea, 1-cyano-3-[5-(3-imidazol-1-yl-4-methanesulfonyl-phenyl)-4-methyl-thiazol-2-yl]-urea, 1-(2-cyano-ethyl)-3-[5-(3-imidazol-1-yl-4-methane-sulfonyl-phenyl)-4-methyl-thiazol-2-yl]-1-methyl-urea and 1-(2-cyano-ethyl)-1-ethyl-3-[5-(3-imidazol-1-yl-4-methanesulfonyl-phenyl)-4-methyl-thiazol-2-yl]-urea respectively are prepared by the same procedure as Example 150 by replacing 3-aminopropionitrile (part 150b) in that Example with the appropriate amine.

Example 156

N-{5-[4-Chloro-3-(2-hydroxy-ethylsulfamoyl)-phenyl]-4-methyl-thiazol-2-yl}-acetamide The title compound is made via an analogous procedure to N-[5-(4-Methoxy-3-sulfamoyl-phenyl)-4-methyl-thiazol-2-yl]-acetamide (Example 30) by replacing 4-methoxyphenyl acetone (in example 30a) with 4-chlorophenyl acetone; and ammonia with 2-amino ethanol.

Agents of the invention also include compounds of formula XIX where $R^a$, $R^b$, $R^c$ and $R^1$ are as shown in the Table 3 below, the method of preparation being described thereafter. The table also shows mass spectrometry (MH+) data. The examples are in free form.

TABLE 3

Compounds of the invention

| Ex. | $R^a$ | $R^b$ | $R^c$ | $R^1$ | m/s MH+ |
|---|---|---|---|---|---|
| 157 | S(O)₂CH₃ | N-methylimidazole | H | C(O)CH₂Cl | 411 |
| 158 | S(O)₂CH₃ | —CF₃ | H | C(O)CH₂OCH₃ | 409 |
| 159 | S(O)₂CH₃ | F | H | C(O)CH₂CH₃ | 343.1 |
| 160 | S(O)₂CH₃ | N-methylimidazole | H | C(O)CH₂CH₃ | 391.2 |
| 161 | F | —OCH₃ | H | C(O)CH₃ | 281 |
| 162 | Cl | S(O)₂CH₃ | H | C(O)-azetidine-OH | 402.2 |
| 163 | Cl | S(O)₂CH₃ | —H | C(O)NH-pyridyl-morpholine | 508.3 |
| 164 | S(O)₂CH₃ | F | H | C(O)NH(CH₂)₃C(O)OCH₂CH₃ | 444 |
| 165 | S(O)₂CH₃ | F | H | C(O)NHCH₂CH(CH₃)OC(O)CH₃ | 430 |

TABLE 3-continued

Compounds of the invention

| Ex. | R$^a$ | R$^b$ | R$^c$ | R$^1$ | m/s MH+ |
|---|---|---|---|---|---|
| 166 | methylsulfonyl (S(=O)$_2$CH$_3$) | —CF$_3$ | H | acetamido-CH$_2$CH(CH$_3$)-C(=O)O-ethyl | 480 |
| 167 | methylsulfonyl | —CF$_3$ | H | acetamido-(CH$_2$)$_3$-C(=O)O-ethyl | 494 |
| 168 | methylsulfonyl | N-methylimidazole | H | acetamido-CH$_2$CH(CH$_3$)-C(=O)O-ethyl | 478 |
| 169 | methylsulfonyl | N-methylimidazole | H | acetamido-(CH$_2$)$_3$-C(=O)O-ethyl | 492 |
| 170 | Cl | methylsulfonyl | H | acetamido-CH$_2$CH(CH$_3$)-C(=O)O-ethyl | 446.2 |
| 171 | isopropylsulfonyl | Cl | Cl | acetamido-CH$_2$CH(CH$_3$)-C(=O)O-ethyl | 509.2 |
| 172 | methylsulfonyl | F | H | acetamido-(CH$_2$)$_3$-C(=O)O-ethyl | 415.2 |
| 173 | isopropylsulfonyl | H | H | acetamido-CH$_2$CH$_2$-C(=O)OH | 413.2 |

TABLE 3-continued

Compounds of the invention

| Ex. | $R^a$ | $R^b$ | $R^c$ | $R^1$ | m/s MH+ |
|---|---|---|---|---|---|
| 174 | Cl | 4-methyl-piperazin-1-yl sulfonyl | H | acetamido-ethyl | 458.3 |
| 175 | methylsulfonyl | —CN | H | acetyl (CH₃C(O)—) | 336.1 |
| 176 | H | methylsulfonyl | H | N-(3-ethoxy-3-oxopropyl)acetamido | 412.1 |
| 177 | methylsulfonyl | F | H | carbamoylmethyl-carbonyl (acetamido-NH₂) | 330 |
| 178 | methylsulfonyl | F | H | N-(2-(5-ethyloxazol-2-yl)ethyl)acetamido | 453 |
| 179 | methylsulfonyl | F | H | N-(2-(4-ethyloxazol-2-yl)ethyl)acetamido | 453.3 |
| 180 | methylsulfonyl | F | H | N-(2-(5-methyloxazol-2-yl)ethyl)acetamido | 439.03 |
| 181 | methylsulfonyl | F | H | N-(2-(4-methyloxazol-2-yl)ethyl)acetamido | 439.07 |

Preparation of Specific Examples

Example 157

2-Chloro-N-[5-(3-imidazol-1-yl-4-methanesulfonyl-phenyl)-4-methyl-thiazol-2-yl]-acetamide 5-(3-Imidazol-1-yl-4-methanesulfonyl-phenyl)-4-methyl-thiazol-2-ylamine (Example 148) (0.537 g, 1.60 mmol) and chloroacetyl chloride (5 ml) are heated together for 2 hours. The reaction mixture is allowed to cool to room temperature and the solid filtered and washed with saturated sodium bicarbonate solution (3×100 ml) and water (2×50 ml) to yield the titled compound.

Example 158

N-[5-(4-Methanesulfonyl-3-trifluoromethyl-phenyl)-4-methyl-thiazol-2-yl]-2-methoxy-acetamide 158a) 5-(4-Methanesulfonyl-3-trifluoromethyl-phenyl)-4-methyl-thiazol-2-ylamine The title compound is prepared by an analogous procedure to N-[5-(3-fluoro-4-methane-sulfonyl-phenyl)-4-methyl-thiazol-2-yl]-acetamide (Example 64) by replacing 3,4-difluorobenz-aldehyde with 3-fluoro-4-trifluoromethylbenzaldehyde (part 64a) and by replacing N-acetal-thiourea with thiourea (part 64d).

158b) N-[5-(4-Methanesulfonyl-3-trifluoromethyl-phenyl)-4-methyl-thiazol-2-yl]-2-methoxy-acetamide 5-(4-Methanesulfonyl-3-trifluoromethyl-phenyl)-4-methyl-thiazol-2-ylamine (158a) (0.1 g, 0.3 mmol) is added to a solution of HATU (0.226 g, 0.6 mmol), methoxyacetic acid (0.046 ml, 0.6 mmol) and DIPEA (0.1 ml, 0.6 mmol) in DMF (7.5 ml). The reaction mixture was left to stir for 3 days at room temperature. The reaction mixture is filtered through basic alumina. The solvent is removed in vacuo and the product is purified by chromatography on silica eluting with ethyl acetate-hexane (3:1) to give the titled compound.

Example 159

N-[5-(3-Fluoro-4-methanesulfonyl-phenyl)-4-methyl-thiazol-2-yl]-propionamide 5-(3-Fluoro-4-methanesulfonyl-phenyl)-4-methyl-thiazol-2-ylamine (Example 72) (1 g, 3.39 mmol) is suspended in propionic anhydride (12.5 ml) and heated to 70° C. for 1 hour. The reaction mixture is cooled to room temperature and the solvent removed in vacuo. The solid is triturated with ether to yield the titled compound.

Example 160

N-[5-(3-Imidazol-1-yl-4-methanesulfonyl-phenyl)-4-methyl-thiazol-2-yl]-propionamide The title compound is prepared via an analogous procedure to N-[5-(3-imidazol-1-yl-4-methanesulfonyl-phenyl)-4-methyl-thiazol-2-yl]-acetamide (Example 80) by replacing N-[5-(3-fluoro-4-methanesulfonyl-phenyl)-4-methyl-thiazol-2-yl]-acetamide in this example with N-[5-(3-Fluoro-4-methanesulfonyl-phenyl)-4-methyl-thiazol-2-yl]-propionamide (159).

Example 161

N-[5-(4-Fluoro-3-methoxy-phenyl)-4-methyl-thiazol-2-yl]-acetamide 161a) 1-(4-Fluoro-3-methoxy-phenyl)-propan-2-one The title compound is prepared via an analogous procedure to 1-((3-fluoro-4-methanesulfonyl-phenyl)-propan-2-one (64c) (steps 64b-64c) by replacing 3-fluoro-4-methanesulfonyl-benzaldehyde in step 64b with 4-fluoro-3-methoxy-benzaldehyde.

161b) 1-bromo-1-(4-fluoro-3-methoxy-phenyl)-propan-2-one

A stirred solution of 1-(4-fluoro-3-methoxy-phenyl)-propan-2-one (161a) (0.5 g, 2.74 mmol) in dry THF (5 ml) is treated dropwise with a solution of 2-carboxyethyltriphenylphosphonium perbromide (1.66 g, 2.88 mmol) in THF. The reaction mixture is allowed to stir at room temperature for 1.5 hours and then filtered. The filtrate is concentrated in vacuo to yield the titled compound.

161c) N-[5-(4-Fluoro-3-methoxy-phenyl)-4-methyl-thiazol-2-yl]-acetamide

1-Bromo-1-(4-fluoro-3-methoxy-phenyl)-propan-2-one (161b) (0.72 g, 2.74 mmol) is dissolved in ethanol (20 ml) and N-acetylthiourea (0.324 g, 2.72 mmol) is added in one portion. The mixture is stirred at 80° C. overnight then allowed to cool whereupon the product crystallised. Filtration affords the title compound as a white solid.

Example 162

3-Hydroxy-azetidine-1-carboxylic acid [5-(4-chloro-3-methanesulfonyl-phenyl)-4-methyl-thiazol-2-yl]-amide 162a) 1-Benzhydryl-3-(tert-butyl-diphenyl-silanyloxy)-azetidine A stirred solution of 1-Benzhydrylazetan-3-ol (2.0 g, 8.4 mmol) in DMF (20 ml) at 0° C. is treated with imidazole (0.57 g, 8.4 mmol) and t-butylchlorodiphenyl silane (2.31 g, 8.4 mmol). The reaction mixture is allowed to warm up to room temperature and stirred overnight. The mixture is poured into water (250 ml) and extracted with EtOAc (3×100 ml). The combined organic extracts are washed with water (2×100 ml), brine (100 ml) and dried over $MgSO_4$. The solvent is removed in vacuo to yield the titled compound.

162b) 3-(tert-Butyl-diphenyl-silanyloxy)-azetidine

A stirred solution of 1-benzhydryl-3-(tert-butyl-diphenyl-silanyloxy)-azetidine (162a) (4.0 g, 8.4 mmol) in DCE (60 ml) at room temperature is treated with 1-chloroethylchloroformate (1.2 ml, 10.9 mmol) and the reaction mixture is heated to 80° C. After 2 hours, the solvent is removed in vacuo and the residue is dissolved in methanol (60 ml) and heated to reflux. After 1 h the reaction mixture is poured into water (250 ml), acidified with hydrochloric acid (1M solution) and washed with EtOAc (3×75 ml). The aqueous solution is basified with saturated sodium bicarbonate solution and extracted with EtOAc (3×75 ml). The combined organic lay-

162c) 3-(tert-Butyl-diphenyl-silanyloxy)-azetidine-1-carboxylic acid [5-(4-chloro-3-methanesulfonyl-phenyl)-4-methyl-thiazole-2-yl]amide A stirred solution of 5-(4-chloro-3-methanesulfonyl-phenyl)-2-isocyanato-4-methyl-thiazole [prepared by the same procedure as example 88a replacing 5-(3-fluoro-4-methanesulfonyl-phenyl)-4-methyl-thiazol-2-ylamine (Example 72) in this example with 5-(4-chloro-3-methanesulfonyl-phenyl)-4-methyl-thiazol-2-ylamine (Example 83)] (0.2 g, 0.61 mmol) in DMF is treated with 3-(tert-butyl-diphenyl-silanyloxy)-azetidine (162b) (0.25 g, 0.8 mmol) and the reaction mixture is heated to 120° C. After 30 minutes, the reaction is complete. The product is purified by chromatography on silica eluting with ethyl acetate-hexane (1:2) to give the titled compound.

162d) 3-Hydroxy-azetidine-1-carboxylic acid [5-(4-chloro-3-methanesulfonyl-phenyl)-4-methyl-thiazol-2-yl]-amide A stirred solution of 3-(tert-butyl-diphenyl-silanyloxy)-azetidine-1-carboxylic acid [5-(4-chloro-3-methanesulfonyl-phenyl)-4-methyl-thiazole-2-yl]amide (162c) (0.15 g, 0.23 mmol) in THF (2 ml) at room temperature is treated with tetrabutylammonium fluoride (1.0 M in THF, 0.23 ml, 0.23 mmol). After 30 minutes, the reaction was complete. Purification by preparative LC-MS affords the titled compound.

Example 163

1-[5-(4-Chloro-3-methanesulfonyl-phenyl)-4-methyl-thiazol-2-yl]-3-(6-morpholin-4-yl-pyridin-3-yl)-urea The title compound is prepared by the same procedure as 1-[5-(3-fluoro-4-methanesulfonyl-phenyl)-4-methyl-thiazol-2-yl]-3-(2-hydroxy-ethyl)-urea (Example 88) replacing 5-(3-fluoro-4-methanesulfonyl-phenyl)-4-methyl-thiazol-2-ylamine (Example 72) with 5-(4-chloro-3-methanesulfonyl-phenyl)-4-methyl-thiazol-2-ylamine (Example 83) and by replacing 2-aminoethanol (part 88b) with 6-morpholinopyridin-3-amine.

Example 164

4-{3-[5-(3-Fluoro-4-methanesulfonyl-phenyl)-4-methyl-thiazol-2-yl]-ureido}-butyric acid ethyl ester 5-(3-Fluoro-4-methanesulfonyl-phenyl)-4-methyl-thiazol-2-ylamine (Example 72), (0.1 g, 0.31 mmol) DIPEA (0.039 ml, 0.34 mmol), ethyl-4-isocyanatobutyrate (0.046 ml, 0.31 mmol) in DCM (2 ml) are heated together at reflux overnight. The reaction mixture is diluted with DCM (20 ml) and washed with 1M hydrochloric acid (15 ml), water (2×15 ml), brine (15 ml), dried over MgSO$_4$, filtered and concentrated in vacuo to yield the titled compound as an off white solid.

Example 165

3-{3-[5-(3-Fluoro-4-methanesulfonyl-phenyl)-4-methyl-thiazol-2-yl]-ureido}-propionic acid ethyl ester The title compound is prepared by the same procedure as 4-{3-[5-(3-Fluoro-4-methanesulfonyl-phenyl)-4-methyl-thiazol-2-yl]-ureido}-butyric acid ethyl ester (Example 164) by replacing ethyl-4-isocyanatobutyrate with 3-isocyanato-propionic acid ethyl ester.

Example 166

3-{3-[5-(4-Methanesulfonyl-3-trifluoromethyl-phenyl)-4-methyl-thiazol-2-yl]-ureido}-propionic acid ethyl ester The title compound is prepared by the same procedure as 4-{3-[5-(3-fluoro-4-methanesulfonyl-phenyl)-4-methyl-thiazol-2-yl]-ureido}-butyric acid ethyl ester (Example 164) by replacing 5-(3-fluoro-4-methanesulfonyl-phenyl)-4-methyl-thiazol-2-ylamine (Example 72) with 5-(4-methanesulfonyl-3-trifluoromethyl-phenyl)-4-methyl-thiazol-2-ylamine (158a) and replacing ethyl-4-isocyanatobutyrate with 3-isocyanato-propionic acid ethyl ester.

Example 167

4-{3-[5-(4-Methanesulfonyl-3-trifluoromethyl-phenyl)-4-methyl-thiazol-2-yl]-ureido}-butyric acid ethyl ester The title compound is prepared by the same procedure as 4-{3-[5-(3-fluoro-4-methanesulfonyl-phenyl)-4-methyl-thiazol-2-yl]-ureido}-butyric acid ethyl ester (Example 164) by replacing 5-(3-fluoro-4-methanesulfonyl-phenyl)-4-methyl-thiazol-2-ylamine (Example 72) with 5-(4-methanesulfonyl-3-trifluoromethyl-phenyl)-4-methyl-thiazol-2-ylamine (158a).

Example 168

3-{3-[5-(3-Imidazol-1-yl-4-methanesulfonyl-phenyl)-4-methyl-thiazol-2-yl]-ureido}-propionic acid ethyl ester The title compound is prepared by the same procedure as 4-{3-[5-(3-fluoro-4-methanesulfonyl-phenyl)-4-methyl-thiazol-2-yl]-ureido}-butyric acid ethyl ester (Example 164) by replacing 5-(3-fluoro-4-methanesulfonyl-phenyl)-4-methyl-thiazol-2-ylamine (Example 72) with 5-(3-imidazol-1-yl-4-methanesulfonyl-phenyl)-4-methyl-thiazol-2-ylamine (Example 148) and replacing ethyl-4-isocyanatobutyrate with 3-isocyanato-propionic acid ethyl ester.

Example 169

4-{3-[5-(3-Imidazol-1-yl-4-methanesulfonyl-phenyl)-4-methyl-thiazol-2-yl]-ureido}-butyric acid ethyl ester The title compound is prepared by the same procedure as 4-{3-[5-(3-fluoro-4-methanesulfonyl-phenyl)-4-methyl-thiazol-2-yl]-ureido}-butyric acid ethyl ester (Example 164) by replacing 5-(3-fluoro-4-methanesulfonyl-phenyl)-4-me-

Example 170

3-{3-[5-(4-Chloro-3-methanesulfonyl-phenyl)-4-methyl-thiazol-2-yl]-ureido}-propionic acid ethyl ester The title compound is prepared by the same procedure as 4-{3-[5-(3-fluoro-4-methanesulfonyl-phenyl)-4-methyl-thiazol-2-yl]-ureido}-butyric acid ethyl ester (Example 164) by replacing 5-(3-fluoro-4-methanesulfonyl-phenyl)-4-methyl-thiazol-2-ylamine (Example 72) with 5-(4-chloro-3-methanesulfonyl-phenyl)-4-methyl-thiazol-2-ylamine (Example 83) and replacing ethyl-4-isocyanatobutyrate with 3-isocyanato-propionic acid ethyl ester.

Example 171

3-{3-[5-(3,5-Dichloro-4-dimethylsulfamoyl-phenyl)-4-methyl-thiazol-2-yl]-ureido}-propionic acid ethyl ester 171a) N-[5-(3,5-Dichloro-4-dimethylsulfamoyl-phenyl)-4-methyl-thiazol-2-yl]-acetamide The title compound is prepared by an analagous procedure to N-[5-(3,5-dichloro-4-sulfamoyl-phenyl)-4-methyl-thiazol-2-yl]-acetamide (Example 6) by replacing ammonia with dimethylamine.

171b) 4-(2-Amino-4-methyl-thiazol-5-yl)-2,6-dichloro-N,N-dimethyl-benzenesulfonamide The title compound is prepared by the same procedure as 4-(2-amino-4-methyl-thiazol-5-yl)-2,6-dichloro-benzenesulfonamide (Example 26) by replacing N-[5-(3,5-dichloro-4-sulfamoyl-phenyl)-4-methyl-thiazol-2-yl]-acetamide (Example 6) with N-[5-(3,5-dichloro-4-dimethylsulfamoyl-phenyl)-4-methyl-thiazol-2-yl]-acetamide (171a).

171c) 3-{3-[5-(3,5-Dichloro-4-dimethylsulfamoyl-phenyl)-4-methyl-thiazol-2-yl]-ureido)}-propionic acid ethyl ester The title compound is prepared by the same procedure as 4-{3-[5-(3-Fluoro-4-methanesulfonyl-phenyl)-4-methyl-thiazol-2-yl]-ureido}-butyric acid ethyl ester (Example 164) by replacing 5-(3-fluoro-4-methanesulfonyl-phenyl)-4-methyl-thiazol-2-ylamine (Example 72) with 4-(2-amino-4-methyl-thiazol-5-yl)-2,6-dichloro-N,N-dimethyl-benzenesulfonamide (171b) and replacing ethyl-4-isocyanatobutyrate with 3-isocyanato-propionic acid ethyl ester.

Example 172

4-[5-(3-Fluoro-4-methanesulfonyl-phenyl)-4-methyl-thiazol-2-ylcarbamoyl]-butyric acid methyl ester Methyl-4-(chloroformyl) butyrate (4.0 mmol) is added to a stirred solution of 5-(3-fluoro-4-methanesulfonyl-phenyl)-4-methyl-thiazol-2-ylamine (Example 72) (0.77 g, 2.69 mmol) and heated to 60° C. for 1.5 hours. The reaction mixture is allowed to cool to room temperature and the solvent removed in vacuo. The residue is washed with saturated sodium bicarbonate solution (2×50 ml) and water (1×50 ml). The product is extracted with ethyl acetate (2×50 ml) and the combined organic extracts dried (MgSO$_4$). Removal of the solvent followed by recrystallisation from ethyl acetate affords the tided compound.

Example 173

3-{3-[5-(4-Dimethylsulfamoyl-phenyl)-4-methyl-thiazol-2-yl]-ureido}-propionic acid To a stirred solution of 3-{3-[5-(4-dimethylsulfamoyl-phenyl)-4-methyl-thiazol-2-yl]-ureido}-propionic acid ethyl ester (Example 24) in methanol (5 ml) is added dropwise sodium hydroxide (2M, 3 ml) over 2 minutes. The reaction mixture is heated at reflux overnight and then allowed to cool to room temperature. The mixture is neutralised with hydrochloric acid (2M, 3 ml) and the resulting precipitate is filtered, washed with water (20 ml) and dried in vacuo to yield the titled compound.

Example 174

1-{5-[4-Chloro-3-(4-methyl-2-piperazine-1-sulfonyl)-phenyl]-4-methyl-thiazol-2-yl}-3-ethyl-urea 174a) 2-Chloro-5-(2-oxopropyl)-benzenesulphonyl chloride To chlorosulfonic acid (25 ml, excess) cooled at −10° C. is added dropwise 4-chlorophenyl acetone (1.0 g, 5.93 mmol). The temperature is kept below 0° C. throughout the addition. The reaction mixture is then left to warm up to room temperature overnight. The reaction mixture is poured carefully onto ice (1500 ml). Once the ice is melted, the aqueous layer is extracted with dichloromethane (3×250 ml). The combined organic layers are dried over MgSO$_4$, filtered and concentrated to afford the titled compound as an off-white solid.

174b) 1-[4-Chloro-3-(4-methyl-piperazine-1-sulfonyl)-phenyl]-propan-2-one

2-Chloro-5-(2-oxopropyl)-benzenesulphonyl chloride (174a) (2.0 g, 7.5 mmol) is dissolved in dioxan (50 ml) with stirring. Sodium carbonate (7.5 ml, 2M solution, 2 eq.) is added followed by 1-methyl piperazine (0.75 g, 7.5 mmol). After 30 min the reaction mixture is poured onto water (250 ml) and extracted with ethyl acetate (3×100 ml). The combined organic extracts are washed with water (2×100 ml) followed by brine (100 ml) and dried (MgSO$_4$). After filtration the solvent is removed and the product is purified by chromatography on silica, eluting with ethyl acetate/hexane (1:2) to afford the titled compound.

174c) 1-Bromo-1-[4-chloro-3-(4-methyl-piperazine-1-sulfonyl)-phenyl]-propan-2-one A stirred solution of 1-[4-chloro-3-(4-methyl-piperazine-1-sulfonyl)-phenyl]-propan-2-one (174b) (0.5 g, 1.22 mmol) in dry THF (5 ml) is treated dropwise with a solution of 2-carboxyethyltriphenylphosphonium perbromide (0.84 g, 1.44 mmol) in THF. The reaction mixture is allowed to stir at room temperature for 1.5 hours and then filtered. The filtrate is concentrated in vacuo to yield the titled compound.

174d) 5-[4-Chloro-3-(4-methyl-piperazine-1-sulfonyl)-phenyl]-4-methyl-thiazol-2-ylamine The title compound is prepared as an HBr salt by the same procedure as N-[5-(4-fluoro-3-methoxy-phenyl)-4-methyl-thiazol-2-yl]-acetamide (161c) by replacing 1-bromo-1-(4-fluoro-3-methoxy-phenyl)-propan-2-one (161b) with 1-bromo-1-[4-chloro-3-(4-methyl-piperazine-1-sulfonyl)-phenyl]-propan-2-one (171c) and N-acetylthiourea with thiourea.

174e) 1-{5-[4-Chloro-3-(4-methyl-piperazine-1-sulfonyl)-phenyl]-4-methyl-thiazol-2-yl}-3-ethyl-urea A stirred solution of 5-[4-Chloro-3-(4-methyl-piperazine-1-sulfonyl)-phenyl]-4-methyl-thiazol-2-ylamine hydrobromide (174d) (0.1 g, 0.26 mmol) in DMF (1 ml) at room temperature is treated with DIPEA (0.07 g, 0.52 mmol) and ethyl isocyanate (0.025 ml, 0.33 mmol). The reaction mixture is heated to 120° C. for 1 hour and then allowed to cool to room temperature. Purification by preparative LC-MS affords the titled compound.

Example 175

N-[5-(3-Cyano-4-methanesulfonyl-phenyl)-4-methyl-thiazol-2-yl]-acetamide

The titled compound was prepared by an identical procedure to N-[5-(3-fluoro-4-methanesulfonyl-phenyl)-4-methyl-thiazol-2-yl]-acetamide (Example 64) replacing 3,4-difluorobenzaldehyde in this procedure with 2-fluoro-5-formylbenzonitrile.

Examples 176

3-{3-[5-(3-Methanesulfonyl-phenyl)-4-methyl-thiazol-2-yl]-ureido}-propionic acid ethyl ester

176a) 1-(4-Chloro-3-methanesulphonyl-phenyl)-propan-2-one

A stirred solution of 2-Chloro-5-(2-oxo-propyl)-benzenesulphonyl chloride (prepared as described in Example 174a) (20.0 g, 74.9 mmol) in dioxane (300 ml) at room temperature is treated with a solution of sodium sulphite (18.9 g, 150 mmol) and sodium hydrogen carbonate (12.6 g, 150 mmol) in water (200 ml). The reaction mixture is heated to 75° C. for 10 minutes and then allowed to cool to room temperature. The solvent is removed in vacuo and the residue dissolved in DMF (200 ml). The solution is stirred at room temperature and treated with iodomethane (21.2 g, 150 mmol). After stirring for 20 minutes, the reaction mixture is diluted with water (1000 ml) and extracted with ethyl acetate (3×250 ml). The combined organic layers are washed with water (2×200 ml), brine (100 ml), dried over MgSO$_4$ and concentrated in vacuo to yield the titled compound.

176b) 1-(3-Methanesulphonyl-phenyl)-propan-2-one

A solution of 1-(4-chloro-3-methanesulphonyl-phenyl)-propan-2-one (5.49 g, 22.28 mmol) in methanol (250 ml) is stirred under hydrogen in the presence of 10% Pd on carbon (3 g) for 2 hours. The reaction mixture is filtered and concentrated in vacuo to yield a yellow oil of the titled compound.

176c) 1-Bromo-1-(3-methanesulphonyl-phenyl)-propanone

A stirred solution of 1-(3-methanesulphonyl-phenyl)-propan-2-one (176b) (0.25 g, 1.18 mmol) in dioxane (10 ml) at 5° C. is treated with bromine (0.131 g, 0.82 mmol) added in two portions. The reaction is stirred and allowed to warm up to room temperature. The solvent is removed in vacuo to yield an orange oil of the titled compound.

176d) 5-(3-Methanesulphonyl-phenyl)-4-methyl-thiazol-2-ylamine hydrobromide A stirred solution of 1-bromo-1-(3-methanesulphonyl-phenyl)-propanone (176c) (0.32 g, 1.01 mmol) is treated with thiourea (0.067 g, 0.88 mmol) added in one portion. The reaction mixture is allowed to stir at room temperature over two days. The product precipitates out and is filtered to yield the title compound as while solid.

176e) 3-{3-[5-(3-Methanesulfonyl-phenyl)-4-methyl-thiazol-2-yl]-ureido}-propionic acid ethyl ester A stirred suspension of 5-(3-methanesulphonyl-phenyl)-4-methyl-thiazol-2-ylamine hydrobromide (176d) (0.172 g, 0.64 mmol) in DCM (15 ml) is treated with Hunigs base (0.45 ml, 2.36 mmol) followed by ethyl-3-isocyanatopropionate (0.092 g, 0.64 mmol). The reaction mixture is stirred and heated to 60° C. for 10 hours and then the solvent in removed in vacuo. The product is purified by chromatography on silica to give the titled compound

Examples 177

[5-(3-Fluoro-4-methanesulfonyl-phenyl)-4-methyl-thiazol-2-yl]-urea

177a) Imidazole-1-carboxylic acid [5-(3-fluoro-4-methanesulfonyl-phenyl)-4-methyl-thiazol-2-yl]-amide The title compound is prepared by the same procedure as imidazole-1-carboxylic acid [5-(3-imidazol-1-yl-4-methanesulfonyl-phenyl)-4-methyl-thiazol-2-yl]-amide (Example 150a) by replacing 5-(3-imidazol-1-yl-4-methanesulfonyl-phenyl)-4-methyl-thiazol-2-ylamine (Example 148) with 5-(3-fluoro-4-methanesulfonyl-phenyl)-4-methyl-thiazol-2-ylamine (Example 72)

177b) [5-(3-Fluoro-4-methanesulfonyl-phenyl)-4-methyl-thiazol-2-yl]-urea

The title compound is prepared by the same procedure as 1-[5-(3-fluoro-4-methanesulfonyl-phenyl)-4-methyl-thiazol-2-yl]-3-(2-hydroxy-ethyl)-urea (Example 88) by replacing 2-aminoethanol (part 88b) in this example with ammonia.

Examples 178

1-[2-(5-Ethyl-oxazol-2-yl)-ethyl]-3-[5-(3-fluoro-4-methanesulfonyl-phenyl)-4-methyl-thiazol-2-yl]-urea The title compound is prepared by the same procedure as -[5-(3-fluoro-4-methanesulfonyl-phenyl)-4-methyl-thiazol-2-yl]-urea (Example 177) by replacing ammonia (part 177b) with the hydrochloride salt of 2-(5-Ethyl-oxazol-2-yl)-ethylamine (details of preparation procedure follows below), by replacing dioxane with DMF and by using triethylamine as a base.

2-(5-Ethyl-oxazol-2-yl)-ethylamine)

Step 1) [2-(2-Hydroxy-butylcarbamoyl)-ethyl]-carbamic acid benzyl ester

A mixture comprising Z-Beta-Ala-OH (9.0 g, 40.3 mmol), EDCI.HCl (10.0 g, 52.4 mmol), hyrdoxybenzotriazole (5.45 g, 40.3 mmol), triethylamine (7.3 ml, 52.4 mmol) in DCM (150 ml) is stirred at 0° C. for 30 minutes. 1-Amino-2-butanol (4.2 ml, 44.3 mmol) is added in one portion and stirring is continued for 1 hour. The reaction mixture is diluted with water (150 ml) and extracted with dichloromethane (2×150 ml) The organic layers are combined, dried over MgSO₄, filtered and concentrated in vacuo to yield a crude white solid. The product is purified by chromatography on silica eluting with ethanol-ethyl acetate (1:10) to give the titled compound.

Step 2) [2-(2-Oxo-butylcarbamoyl)-ethyl]-carbamic acid benzyl ester

To a stirred solution of oxalyl chloride (2 M in DCM) (13.35 ml, 26.5 mmol) in dry DCM at −78° C. is added dropwise DMSO (2.5 ml, 35.4 mmol). After stirring for 15 minutes, the reaction mixture is treated with a solution of [2-(2-hydroxy-butylcarbamoyl)-ethyl]-carbamic acid benzyl ester (step 1) (6.5 g, 22.1 mol) in dry DCM (40 ml). Triethylamine (13 ml) is added after 1 hour and after stirring at −78° C. for 90 minutes, the reaction mixture is allowed to warm to room temperature. The reaction is diluted with DCM (100 ml) and washed with HCl (1M, 200 ml), saturated sodium bicarbonate solution (200 ml), water (200 ml) and brine (200 ml). The organic portion is dried over MgSO₄, filtered and concentrated in vacuo to yield the titled compound as a white solid.

Step 3) [2-(5-Ethyl-oxazol-2-yl)-ethyl]-carbamic acid benzyl ester

To a stirred suspension of polymer supported triphenylphosphene (19.6 g, 58.9 mmol) in DCM (250 ml) is added iodine (14.95 g, 58.9 mmol). After stirring at room temperature for 10 minutes, the mixture is treated with triethylamine (16.4 ml, 117.5 mmol) followed by a solution of [2-(2-oxo-butylcarbamoyl)-ethyl]-carbamic acid benzyl ester (step 2) (6.88 g, 23.5 mmol) in DCM (50 ml). The reaction mixture is stirred overnight and then filtered through celite, washed through with DCM (500 ml) and the solvent removed in vacuo to yield the titled compound as a brown solid.

Step 4) 2-(5-Ethyl-oxazol-2-yl)-ethylamine (hydrochloride salt)

A solution of [2-(5-ethyl-oxazol-2-yl)-ethyl]-carbamic acid benzyl ester (step 3) (0.41 g, 1.49 mmol), 2M HCl (0.75 ml) in ethanol (40 ml) is stirred under hydrogen in the presence of 10% Pd on carbon (0.041 g) for 5 hours. The reaction mixture is filtered and concentrated in vacuo to yield the titled compound.

Examples 179

1-[2-(4-Ethyl-oxazol-2-yl)-ethyl]-3-[5-(3-fluoro-4-methanesulfonyl-phenyl)-4-methyl-thiazol-2-yl]-urea The title compound is prepared by the same procedure as 1-[2-(5-ethyl-oxazol-2-yl)-ethyl]-3-[5-(3-fluoro-4-methanesulfonyl-phenyl)-4-methyl-thiazol-2-yl]-urea (Example 178) by replacing 2-(5-ethyl-oxazol-2-yl)-ethylamine hydrochloride (step 4) with the hydrochloride salt of 2-(4-ethyl-oxazol-2-yl)-ethylamine. This is prepared by the same procedure as 2-(5-ethyl-oxazol-2-yl)-ethylamine hydrochloride (step 4) by replacing 1-amino-2-butanol (step 1) with 2-amino-1-butanol.

Example 180

1-[5-(3-Fluoro-4-methanesulfonyl-phenyl)-4-methyl-thiazol-2-yl]-3-[2-(5-methyl-oxazol-2-yl)-ethyl]-urea The title compound is prepared by the same procedure as 1-[2-(5-ethyl-oxazol-2-yl)-ethyl]-3-[5-(3-fluoro-4-methanesulfonyl-phenyl)-4-methyl-thiazol-2-yl]-urea (Example 178) by replacing 2-(5-ethyl-oxazol-2-yl)-ethylamine hydrochloride (step 4) with the hydrochloride salt of 2-(5-methyl-oxazol-2-yl)ethylamine. This is prepared by the same procedure as 2-(5-ethyl-oxazol-2-yl)ethylamine hydrochloride (step 4) by replacing 1-amino-2-butanol (step 1) with 1-amino-2-propanol.

Example 181

1-[5-(3-Fluoro-4-methanesulfonyl-phenyl)-4-methyl-thiazol-2-yl]-3-[2-(4-methyl-oxazol-2-yl)-ethyl]-urea The title compound is prepared by the same procedure as 1-[2-(5-ethyl-oxazol-2-yl)-ethyl]-3-[5-(3-fluoro-4-methanesulfonyl-phenyl)-4-methyl-thiazol-2-yl]-urea (Example 178) by replacing 2-(5-ethyl-oxazol-2-yl)-ethylamine hydrochloride (step 4) with the hydrochloride salt of 2-(4-methyl-oxazol-2-yl)ethylamine. This is prepared by the same procedure as 2-(5-ethyl-oxazol-2-yl)-ethylamine hydrochloride (step 4) by replacing 1-amino-2-butanol (step 1) with 2-amino-1-propanol.

The invention claimed is:
1. A compound of formula I

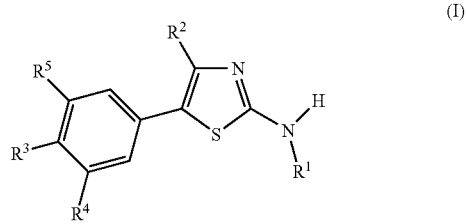

in free or salt form, wherein
$R^1$ is $C_1$-$C_8$-alkylcarbonyl optionally substituted by the group consisting of, hydroxy, $C_1$-$C_8$-alkylamino, carboxy, $C_1$-$C_8$-alkoxycarbonyl, nitrile, phenyl, $C_1$-$C_8$-haloalkyl, $C_1$-$C_8$-alkyl optionally substituted by hydroxy, $C_3$-$C_8$-cycloalkyl optionally substituted by hydroxy, $C_1$-$C_8$-alkoxy optionally substituted by hydroxy, phenyl substituted by hydroxy or $C_1$-$C_8$-alkyl and, 5- or 6-membered unsaturated heterocyclic ring having one or more ring hetero atoms selected from the group consisting of oxygen, nitrogen and sulphur, that heterocyclic ring being optionally substituted by hydroxy, $C_1$-$C_8$-alkyl or $C_1$-$C_8$-alkoxy, $R^2$ is $C_1$-$C_3$-alkyl or halogen;

$R^5$ is hydrogen or halogen;

$R^3$ is hydrogen, hydroxy, amino, —$SOR^8$, —$SO_2R^8$, —$SO_2NH_2$, —$SO_2NR^9R^{10}$, —$COR^8$, —$CONHR^8$, —$NHSO_2R^8$, nitrile, carboxy, —$OR^8$ or $C_1$-$C_8$-haloalkyl;

$R^4$ is —$NR^{12}R^{13}$;

$R^8$ is $C_1$-$C_8$-alkyl or $C_3$-$C_8$-cycloalkyl, optionally substituted by halogen, hydroxy, $C_1$-$C_8$-alkoxy, nitrile, amino, $C_1$-$C_8$-alkylamino or di($C_1$-$C_8$-alkyl)amino;

$R^9$ is $C_1$-$C_8$-alkyl or $C_3$-$C_8$-cycloalkyl, optionally substituted by hydroxy, $C_1$-$C_8$-alkoxy, nitrile, amino, $C_1$-$C_8$-alkylamino, di($C_1$-$C_8$-alkyl)amino or a 5- or 6-membered heterocyclic ring having one or more ring hetero atoms selected from the group consisting of oxygen, nitrogen and sulphur, that ring being optionally substituted by $C_1$-$C_8$-alkyl;

$R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl; and $R^{12}$ and $R^{13}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl.

2. A compound according to claim 1 wherein $R^1$ is $C_1$-$C_8$-alkylcarbonyl optionally substituted by the group consisting of hydroxy, carboxy, $C_1$-$C_8$-alkoxycarbonyl, nitrile, phenyl, $C_1$-$C_8$-haloalkyl, $C_1$-$C_8$-alkyl optionally substituted by hydroxy, $C_1$-$C_8$-alkoxy optionally substituted by hydroxy, and a 5- or 6-membered unsaturated heterocyclic ring having one or more ring hetero atoms selected from the group consisting of oxygen, nitrogen and sulphur, that ring being optionally substituted by $C_1$-$C_8$-alkyl, $R^2$ is $C_1$-$C_3$-alkyl;

$R^5$ is hydrogen or halogen;

$R^3$ is hydrogen, hydroxy, amino, —$SO_2R^8$, —$SO_2NH_2$, —$SO_2NR^9R^{10}$, —$NHSO_2R^8$, cyano, carboxy, —$OR^8$ or $C_1$-$C_4$-haloalkyl;

$R^4$ is —$NR^{12}R^{13}$;

$R^8$ is $C_1$-$C_8$-alkyl;

$R^9$ is $C_1$-$C_8$-alkyl optionally substituted by hydroxy, $C_3$-$C_8$-cycloalkyl optionally substituted by hydroxy, $C_1$-$C_8$-alkoxy, nitrile, di($C_1$-$C_8$-alkyl)amino or a 5- or 6-membered heterocyclic ring having one or more hetero atoms selected from the group consisting of oxygen and nitrogen, that ring being optionally substituted by $C_1$-$C_8$-alkyl;

$R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl; and $R^{12}$ and $R^{13}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl.

3. A compound according to claim 2, in free or salt form, wherein $R^1$ is $C_1$-$C_4$-alkylcarbonyl optionally substituted by the group consisting of hydroxy, carboxy, $C_1$-$C_4$-alkoxycarbonyl, nitrile, phenyl, $C_1$-$C_4$-haloalkyl, $C_1$-$C_4$-alkyl optionally substituted by hydroxy, $C_1$-$C_4$-alkoxy optionally substituted by hydroxy, and a 5- or 6-membered unsaturated heterocyclic ring having one or more ring hetero atoms selected from the group consisting of oxygen, nitrogen and sulphur, that heterocyclic ring being optionally substituted by $C_1$-$C_4$-alkyl, $R^2$ is $C_1$-$C_3$-alkyl;

$R^5$ is hydrogen or halogen;

$R^3$ is hydrogen, hydroxy, amino, $SO_2R^8$, $SO_2NH_2$, $SO_2NR^9R^{10}$, $NHSO_2R^8$, cyano, carboxy, $OR^8$ or $C_1$-$C_4$-haloalkyl;

$R^4$ is —$NR^{12}R^{13}$;

$R^8$ is $C_1$-$C_4$-alkyl;

$R^9$ is $C_1$-$C_4$-alkyl optionally substituted by hydroxy, $C_3$-$C_5$-cycloalkyl optionally substituted by hydroxy, $C_1$-$C_4$-alkoxy, nitrile, di($C_1$-$C_4$-alkyl)amino or a 5- or 6-membered heterocyclic ring having one or more ring hetero atoms selected from the group consisting of oxygen and nitrogen, that ring being optionally substituted by $C_1$-$C_4$-alkyl;

$R^{10}$ is hydrogen or $C_1$-$C_4$-alkyl; or $R^9$ and $R^{10}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_4$-alkyl; and $R^{12}$ and $R^{13}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_4$-alkyl.

4. A compound of formula I according to claim 1 in free or salt form, wherein $R^1$ is $C_1$-$C_8$-alkylcarbonyl optionally substituted by the group consisting of hydroxy, $C_1$-$C_8$-alkylamino, carboxy, $C_1$-$C_8$-alkyl optionally substituted by the group consisting of hydroxy, $C_3$-$C_8$-cycloalkyl optionally substituted by hydroxy, $C_1$-$C_8$-alkoxy optionally substituted by hydroxy, $C_1$-$C_8$-alkoxycarbonyl, nitrile, or phenyl optionally substituted by hydroxy or $C_1$-$C_8$-alkyl, and a 5- or 6-membered unsaturated heterocyclic ring having one or more ring hetero atoms selected from the group consisting of oxygen, nitrogen and sulphur, that heterocyclic ring being optionally substituted by hydroxy, $C_1$-$C_8$-alkyl or $C_1$-$C_8$-alkoxy, $R^2$ is $C_1$-$C_3$-alkyl or halogen;

$R^5$ is hydrogen or halogen;

$R^3$ is hydrogen, hydroxy, amino, —$SOR^8$, —$SO_2R^8$, —$SO_2NH_2$, —$SO_2NR^9R^{10}$, —$COR^8$, —$CONHR^8$, $NHSO_2R^8$, nitrile, carboxy, —$OR^8$ or $C_1$-$C_8$-haloalkyl;

$R^4$ is —$NR^{12}R^{13}$;

$R^8$ is $C_1$-$C_8$-alkyl or $C_3$-$C_8$-cycloalkyl, optionally substituted by halogen, hydroxy, $C_1$-$C_8$-alkoxy, nitrile, amino, $C_1$-$C_8$-alkylamino or di($C_1$-$C_8$-alkyl)amino;

$R^9$ is $C_1$-$C_8$-alkyl or $C_3$-$C_8$-cycloalkyl, optionally substituted by hydroxy, $C_1$-$C_8$-alkoxy, nitrile, amino, $C_1$-$C_8$-alkylamino, di($C_1$-$C_8$-alkyl)amino or a 5- or 6-membered heterocyclic ring having one or more ring hetero atoms selected from the group consisting of oxygen, nitrogen and sulphur, that ring being optionally substituted by $C_1$-$C_8$-alkyl;

$R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl; and $R^{12}$ and $R^{13}$ together with the nitrogen atom to which they are attached form a 5- or 6-membered heterocyclic ring that contains one or more further hetero atoms selected from the group consisting of oxygen, nitrogen and sulphur, that ring being optionally substituted by $C_1$-$C_8$-alkyl.

5. A compound according to claim 4 wherein $R^1$ is $C_1$-$C_8$-alkylcarbonyl optionally substituted by the group consisting of hydroxy, carboxy, $C_1$-$C_8$-alkyl optionally substituted by hydroxy, $C_3$-$C_8$-cycloalkyl optionally substituted by hydroxy, $C_1$-$C_8$-alkoxy optionally substituted by hydroxy, $C_1$-$C_8$-alkoxycarbonyl, nitrile, and phenyl optionally substituted by hydroxy or $C_1$-$C_8$-alkyl;

$R^2$ is $C_1$-$C_3$-alkyl;

$R^5$ is hydrogen or halogen;

$R^3$ is hydrogen, hydroxy, amino, $-SO_2R^8$, $-SO_2NH_2$, $-SO_2NR^9R^{10}$, $-NHSO_2R^8$, cyano, carboxy, $-OR^8$ or $C_1$-$C_4$-haloalkyl;

$R^8$ is $C_1$-$C_8$-alkyl;

$R^9$ is $C_1$-$C_8$-alkyl optionally substituted by hydroxy, $C_3$-$C_8$-cycloalkyl optionally substituted by hydroxy, $C_1$-$C_8$-alkoxy, nitrile, di($C_1$-$C_8$-alkyl)amino or a 5- or 6-membered heterocyclic ring having one or more ring hetero atoms selected from the group consisting of oxygen and nitrogen, that ring being optionally substituted by $C_1$-$C_8$-alkyl;

$R^{10}$ is hydrogen or $C_1$-$C_8$-alkyl; or $R^9$ and $R^{10}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl; and $R^{12}$ and $R^{13}$ together with the nitrogen atom to which they are attached form a 5- or 6-membered heterocyclic ring that contains one or more further hetero atoms selected from the group consisting of oxygen and nitrogen, that ring being optionally substituted by $C_1$-$C_8$-alkyl.

6. A compound of formula I according to claim 1, in free or salt form, wherein $R^1$ is $C_1$-$C_8$-alkylcarbonyl optionally substituted by the group consisting of carboxy, $C_1$-$C_3$-alkoxy, $C_1$-$C_8$-alkoxycarbonyl, or nitrile;

$R^2$ is $C_1$-$C_3$-alkyl or halogen;

$R^5$ is hydrogen or halogen;

$R^3$ is hydrogen, hydroxy, amino, $SOR^8$, $SO_2R^8$, $SO_2NH_2$, $SO_2NR^9R^{10}$, $COR^8$, $CONHR^8$, $NHSO_2R^8$, nitrile, carboxy, $OR^8$ or $C_1$-$C_8$-haloalkyl;

$R^4$ is $NR^{12}R^{13}$;

$R^8$ is $C_1$-$C_8$-alkyl or $C_3$-$C_8$-cycloalkyl, optionally substituted by halogen, hydroxy, $C_1$-$C_8$-alkoxy, nitrile, amino, $C_1$-$C_8$-alkylamino or di($C_1$-$C_8$-alkyl)amino;

$R^9$ is $C_1$-$C_8$-alkyl or $C_3$-$C_8$-cycloalkyl, optionally substituted by hydroxy, $C_1$-$C_8$-alkoxy, nitrile, amino, $C_1$-$C_8$-alkylamino, di($C_1$-$C_8$-alkyl)amino or a 5 or 6-membered heterocyclic ring having one or more ring hetero atoms selected from the group consisting of oxygen, nitrogen and sulphur, that ring being optionally substituted by $C_1$-$C_8$-alkyl;

$R^{10}$ is hydrogen or $C_1$-$C_8$-alkyl; or $R^9$ and $R^{10}$ together with the nitrogen atom to which they are attached form a 5 or 6-membered heterocyclic ring that contains one or more further hetero atoms selected from the group consisting of oxygen, nitrogen and sulphur, that ring being optionally substituted by $C_1$-$C_8$-alkyl; and $R^{12}$ and $R^{13}$ together with the nitrogen atom to which they are attached form a 5 or 6-membered heterocyclic ring that contains one or more further hetero atoms selected from the group consisting of oxygen, nitrogen and sulphur, that ring being optionally substituted by $C_1$-$C_8$-alkyl.

7. A compound according to claim 6 wherein $R^1$ is $C_1$-$C_8$-alkylcarbonyl optionally substituted by carboxy or $C_1$-$C_8$-alkoxycarbonyl;

$R^2$ is $C_1$-$C_3$-alkyl;

$R^5$ is hydrogen or halogen;

$R^3$ is hydrogen, hydroxy, amino, $SO_2R^8$, $SO_2NH_2$, $SO_2NR^9R^{10}$, $NHSO_2R^8$, cyano, carboxy, $OR^8$ or $C_1$-$C_4$-haloalkyl;

$R^4$ is $NR^{12}R^{13}$;

$R^8$ is $C_1$-$C_8$-alkyl;

$R^9$ is $C_1$-$C_8$-alkyl or $C_3$-$C_8$-cycloalkyl, optionally substituted by hydroxy, $C_1$-$C_8$-alkoxy, nitrile, di($C_1$-$C_8$-alkyl)amino or a 5 or 6-membered heterocyclic ring having one or more ring hetero atoms selected from the group consisting of oxygen and nitrogen, that ring being optionally substituted by $C_1$-$C_8$-alkyl;

$R^{10}$ is hydrogen or $C_1$-$C_8$-alkyl; or $R^9$ and $R^{10}$ together with the nitrogen atom to which they are attached form a 5 or 6-membered heterocyclic ring that contains one or more further hetero atoms selected from the group consisting of oxygen and nitrogen, that ring being optionally substituted by $C_1$-$C_5$-alkyl; and $R^{12}$ and $R^{13}$ together with the nitrogen atom to which they are attached form a 5 or 6-membered heterocyclic ring that contains one or more further hetero atoms selected from the group consisting of oxygen and nitrogen, that ring being optionally substituted by $C_1$-$C_8$-alkyl.

8. A compound of claim 1, that is also a compound of formula XIX

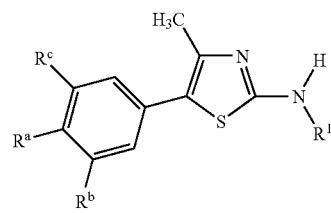

in free or salt form, wherein $R^a$, $R^b$, $R^c$ and $R^1$ are as shown in the following table:

| $R^a$ | $R^b$ | $R^c$ | $R^1$ |
|---|---|---|---|
| methylsulfonyl | 1-imidazolyl | H | acetyl |
| methylsulfonyl | 1-(1,2,4-triazolyl) | H | acetyl |
| methylsulfonyl | 4-methyl-1-imidazolyl | H | acetyl |
| methylsulfonyl | 2-methyl-1-imidazolyl | H | acetyl |
| methylsulfonyl | 2-ethyl-1-imidazolyl | H | acetyl |
| methylsulfonyl | 4-methyl-1-pyrazolyl | H | acetyl |
| methylsulfonyl | 2-propyl-1-imidazolyl | H | acetyl |
| methylsulfonyl | 2-isopropyl-1-imidazolyl | H | acetyl |

9. A compound of claim 1, that is also a compound of formula XIX

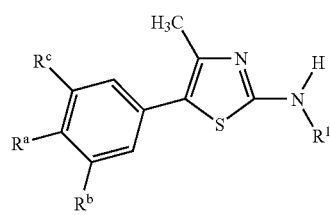

in free or salt form, wherein $R^a$, $R^b$, $R^c$ and $R^1$ are as shown in the following table:

| $R^a$ | $R^b$ | $R^c$ | $R^1$ |
|---|---|---|---|
| methylsulfonyl | 1-imidazolyl | H | chloroacetyl |
| methylsulfonyl | 1-imidazolyl | H | propionyl |

10. A pharmaceutical composition comprising a compound according to claim 1 in combination with at least one drug substance which is an anti-inflammatory, a bronchodilator or an antihistamine drug substance.

11. A pharmaceutical composition comprising as active ingredient a compound according to claim 1, optionally together with a pharmaceutically acceptable diluent or carrier.

12. A pharmaceutical composition comprising as active ingredient a compound according to claim 8, optionally together with a pharmaceutically acceptable diluent or carrier.

13. A pharmaceutical composition comprising as active ingredient a compound according to claim 9, optionally together with a pharmaceutically acceptable diluent or carrier.

14. A compound of claim 1, which compound has the formula:

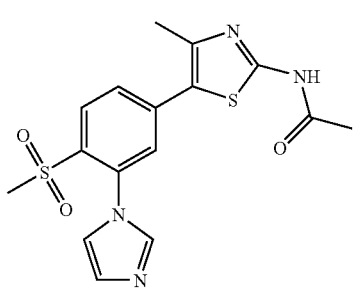

in free or salt form.

* * * * *